United States Patent
Shi et al.

(10) Patent No.: US 9,625,448 B2
(45) Date of Patent: Apr. 18, 2017

(54) DOUBLE CAGED GABA COMPOUNDS, BIS-CNB-GABA

(71) Applicant: The Trustees of Princeton University, Princeton, NJ (US)

(72) Inventors: Diana Shi, Morgantown, WV (US); Samuel Wang, Princeton, NJ (US); Martin Semmelhack, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 228 days.

(21) Appl. No.: 14/664,445

(22) Filed: Mar. 20, 2015

(65) Prior Publication Data
US 2015/0266809 A1    Sep. 24, 2015

Related U.S. Application Data

(60) Provisional application No. 61/993,092, filed on May 14, 2014, provisional application No. 61/968,018, filed on Mar. 20, 2014.

(51) Int. Cl.
| | |
|---|---|
| C07C 229/14 | (2006.01) |
| G01N 33/50 | (2006.01) |
| C07C 227/18 | (2006.01) |
| G01N 33/94 | (2006.01) |
| C07C 269/06 | (2006.01) |

(52) U.S. Cl.
CPC ....... *G01N 33/5058* (2013.01); *C07C 227/18* (2013.01); *G01N 33/9426* (2013.01); *C07C 269/06* (2013.01); *G01N 2500/04* (2013.01)

(58) Field of Classification Search
None
See application file for complete search history.

(56) References Cited

PUBLICATIONS

Shi et al., J. Am. Chem. Soc. 2014, 136, 1976-1981.*
Molnar, et al., "γ-Aminobutyrate, α-carboxy-2-nitrobenzyl ester selectively blocks inhibitory synaptic transmission in rat dentate gyrus", European Journal of Pharmacology 391 (2000), pp. 255-262.
Katz and Dalva, "Scanning laser photostimulation: a new approach for analyzing brain circuits", Journal of Neuroscience Methods 54 (1994), pp. 205-218.
Shoham, et al., "Rapid neurotransmitter uncaging in spatially defined patterns", Nature Methods vol. 2 No. 11, (Nov. 2005).
Farrant and Nusser, "Variations on an inhibitory theme: phasic and tonic activation of GABAA receptors", Nature Reviews—Neuroscience Vo. 6, (Mar. 2005).
Trigo et al., "Laser photolysis of DPNI-GABA, a tool for investigating the properties and distribution of GABA receptors and for silencing neurons in situ", Journal of Neuroscience Methods 181 (2009), pp. 159-169.
Perrais and Ropert, "Effect of zolpidem on miniature IPSCs and occupancy of postsynaptic GABAA receptors in central synapses", The Journal of Neuroscience vol. 19 No. 2 (Jan. 15, 1999), pp. 578-588.

(Continued)

*Primary Examiner* — Karl J Puttlitz
(74) *Attorney, Agent, or Firm* — Volpe and Koenig, P.C.

(57) ABSTRACT

Double caged GABA compounds and compositions including the same are described. Methods of synthesizing and using double caged GABA compounds are provided.

34 Claims, 44 Drawing Sheets

(56) References Cited

PUBLICATIONS

Matsuzaki et al., "Two-photon uncaging of γ-Aminobutyric acid in intact brain tissue", Nature Chem. Biology, Published Online Feb. 21, 2010-DOI:10.1038/NCHEMBIO.321.

Fino et al., "RuBi-Glutamate: two-photon and visible-light photoactivation of neurons and dendritic spines", Frontiers in Neural Circuits, (May 27, 2009).

Verde et al., "Photorelease of GABA with visible light using an inorganic caging group", Frontiers in Neural Circuits, vol. 2 Article 2, (Aug. 2008), www.frontiersin.org.

* cited by examiner

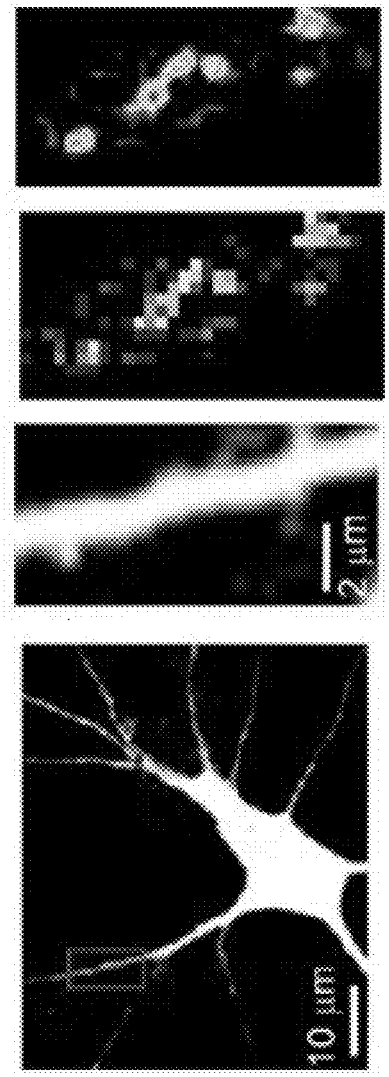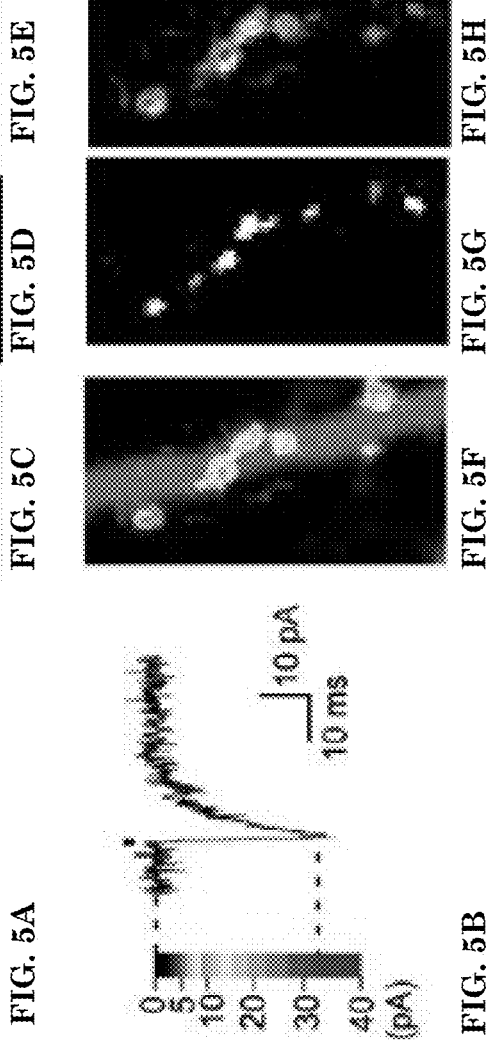

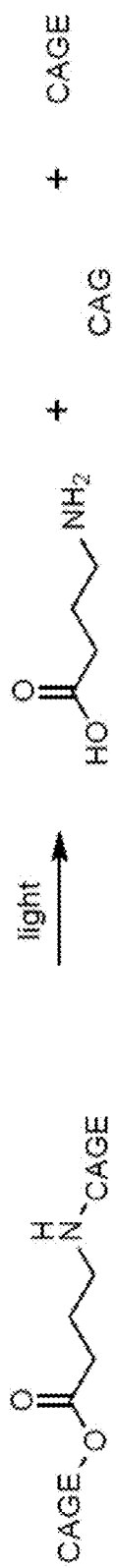
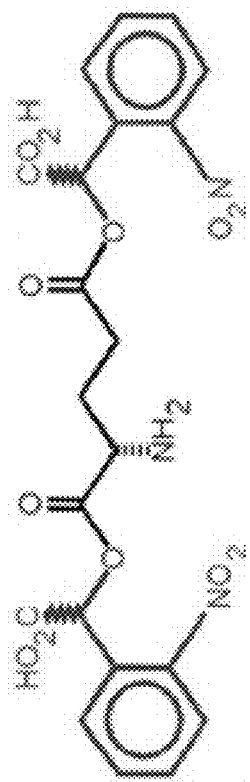
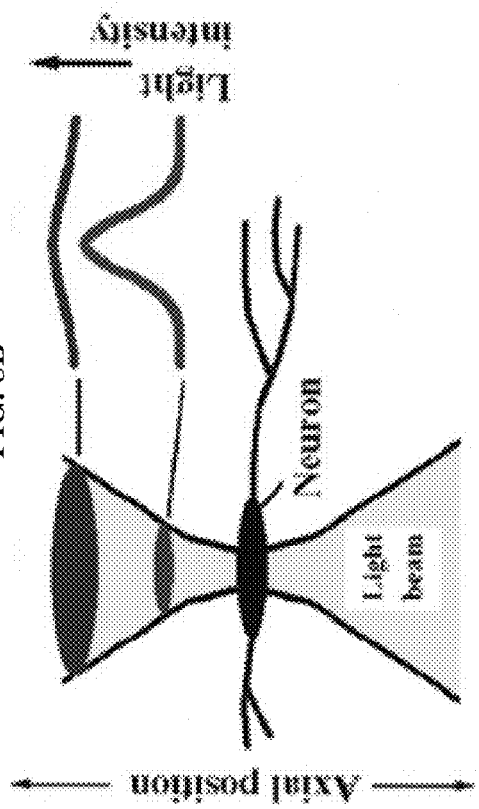
FIG. 8A
FIG. 8B
FIG. 8C

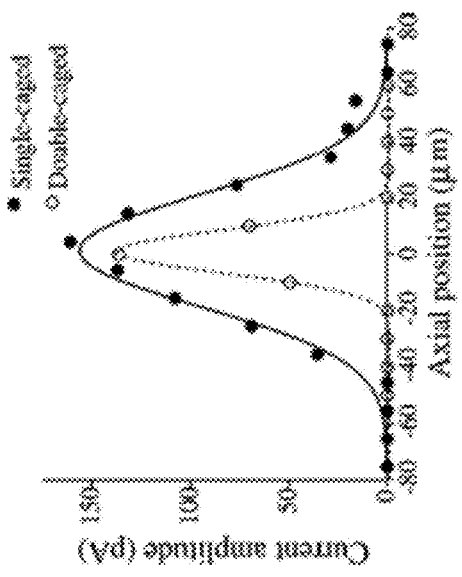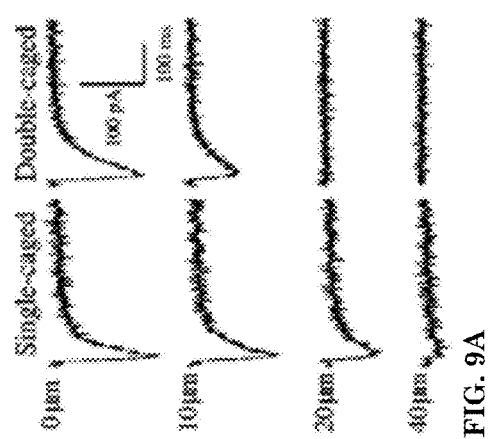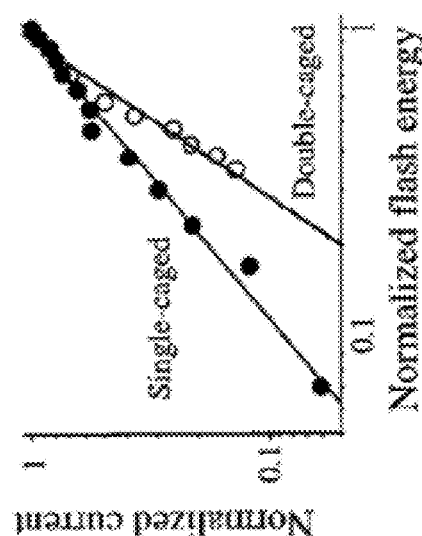
FIG. 9B
FIG. 9C
FIG. 9A

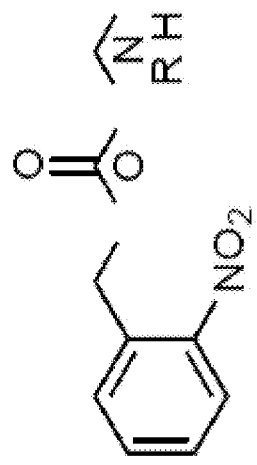
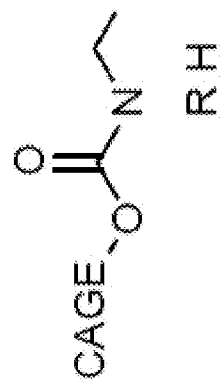
FIG. 13A
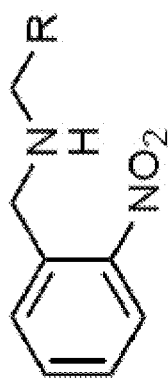
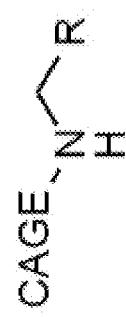
FIG. 13B

| Caged compound | Substrate | $\phi_{dis}$ | $\phi_{sep}{}^a$ | Solvent |
|---|---|---|---|---|
| | ATP | 0.37 | 0.30 | Tris Buffer |
| | Phosphate | 0.38 | n.d. | Aq. CH₃CN |
| | Ala–Ala | 0.267 | 0.253 | D₂O |
| | GABA | 0.35 | n.d. | Buffer |
| | Glutamate | 0.12 | 0.08 | Buffer |
| | Bradykinin | 0.205 | 0.219 | D₂O |

$^a$ n.d. = not determined.

FIG. 16

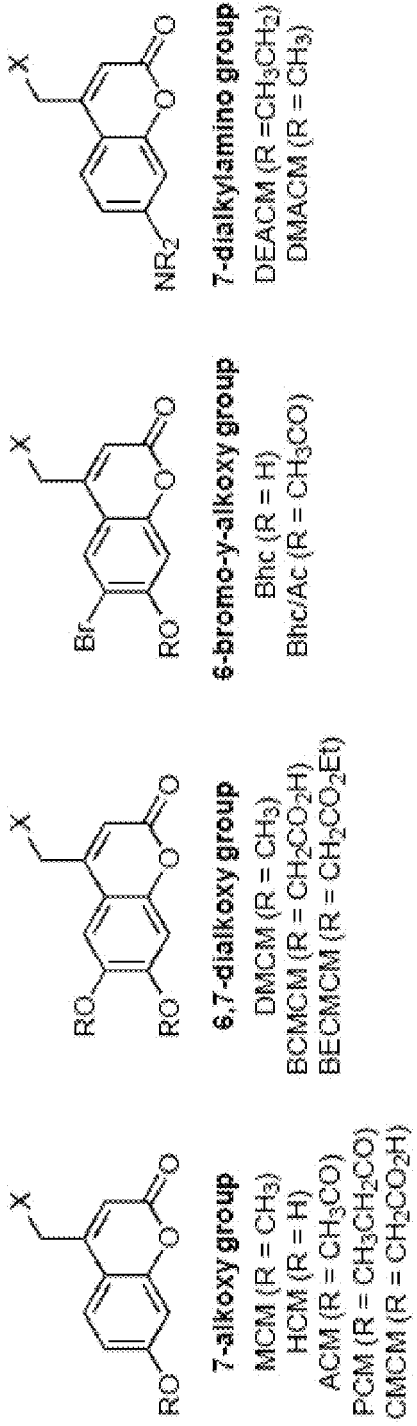
FIG. 21
+
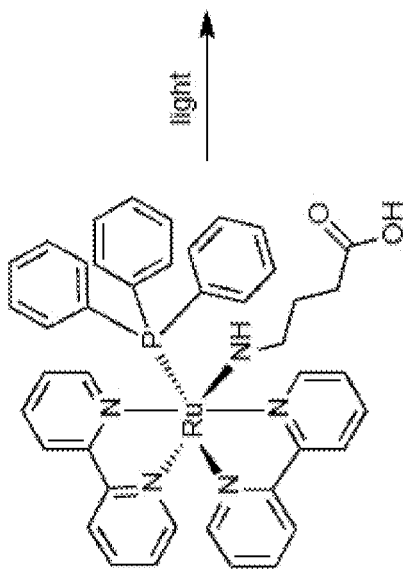
↑ light
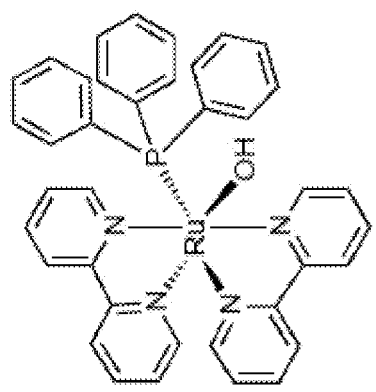
FIG. 22

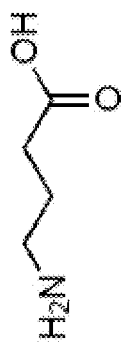
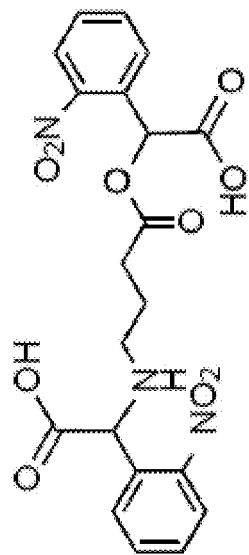
FIG. 23
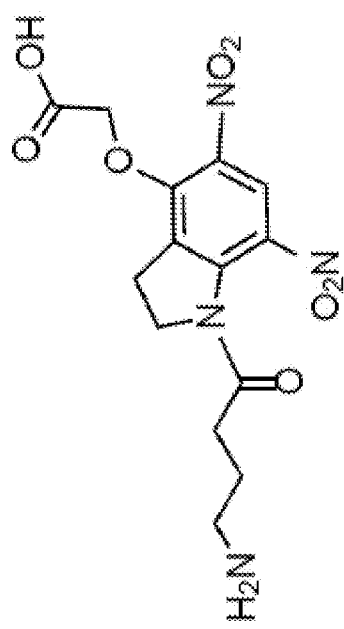
FIG. 24

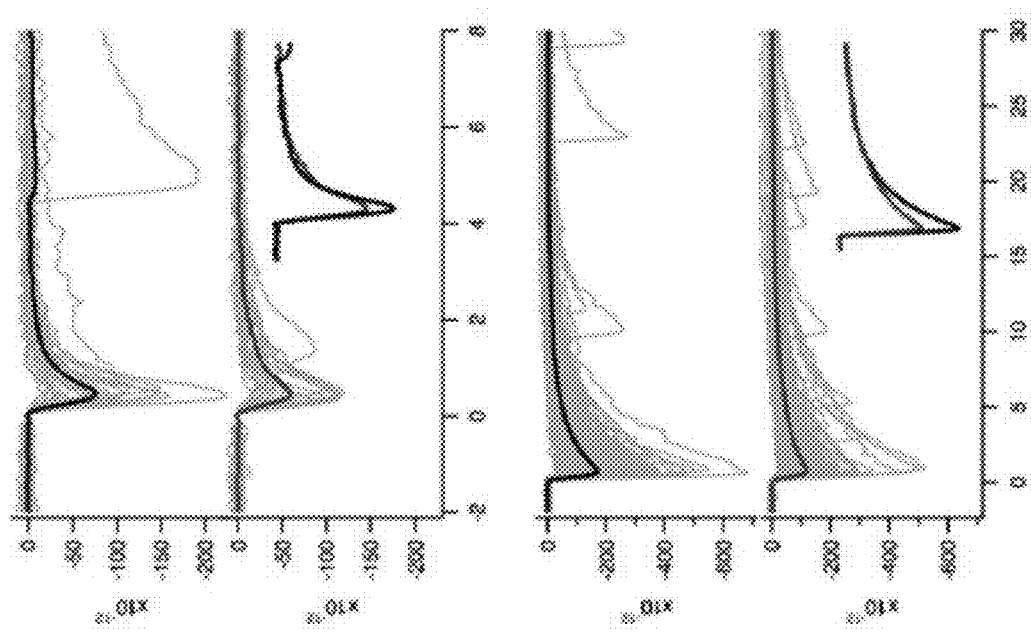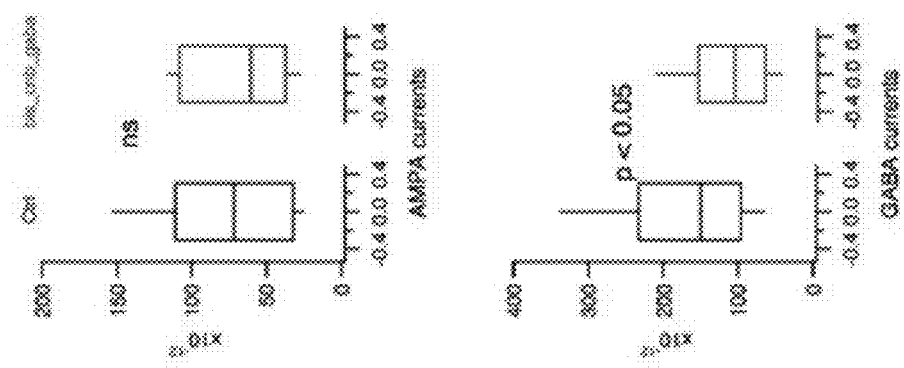
FIG. 39

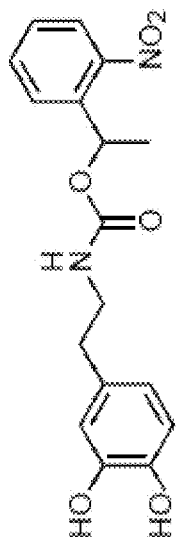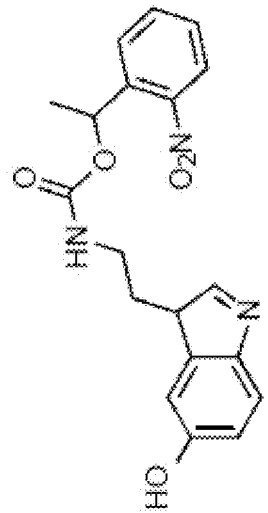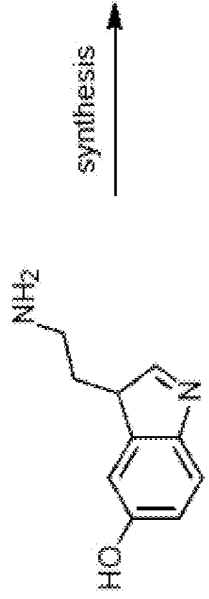
FIG. 40A
FIG. 40B

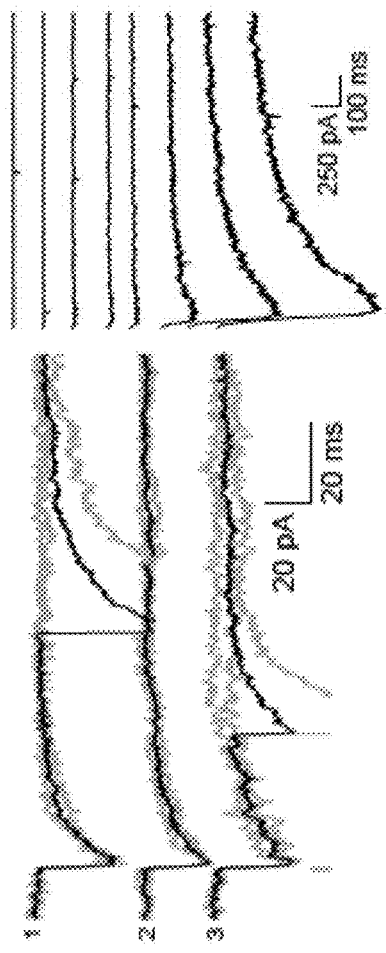
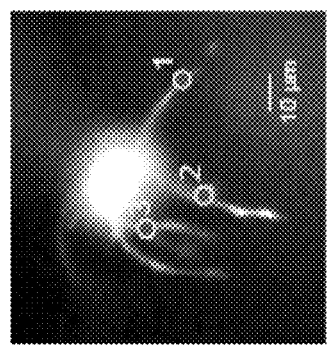
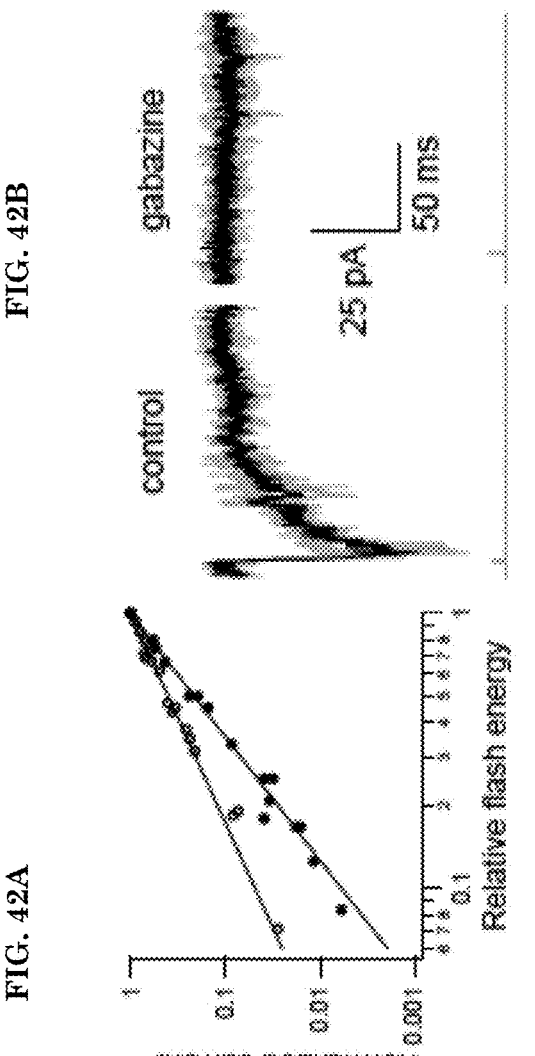
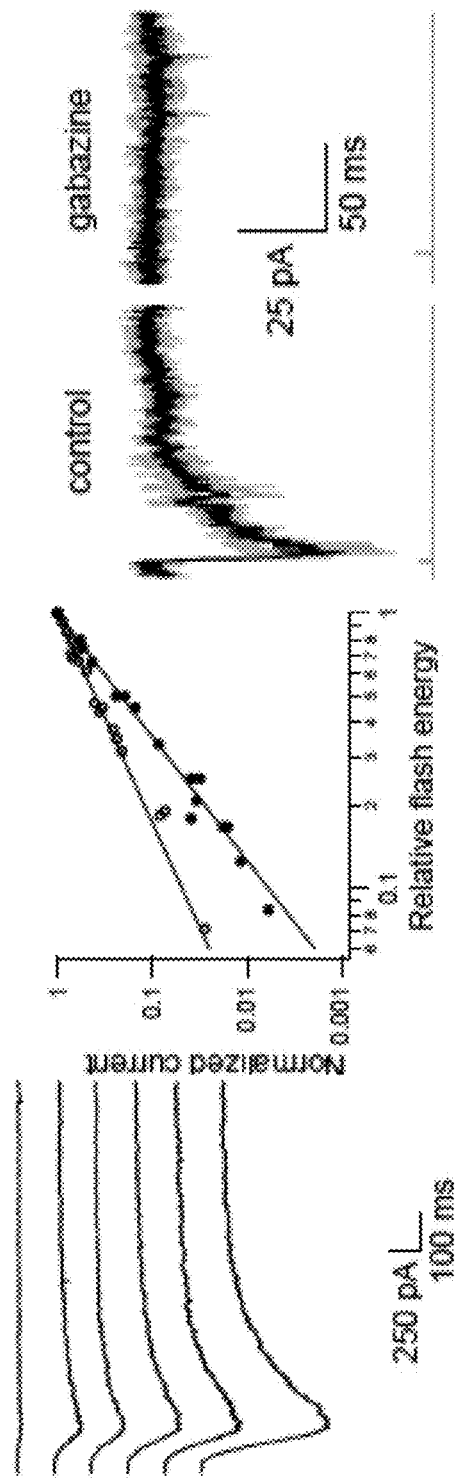
FIG. 42A
FIG. 42B
FIG. 42C
FIG. 42D
FIG. 42E

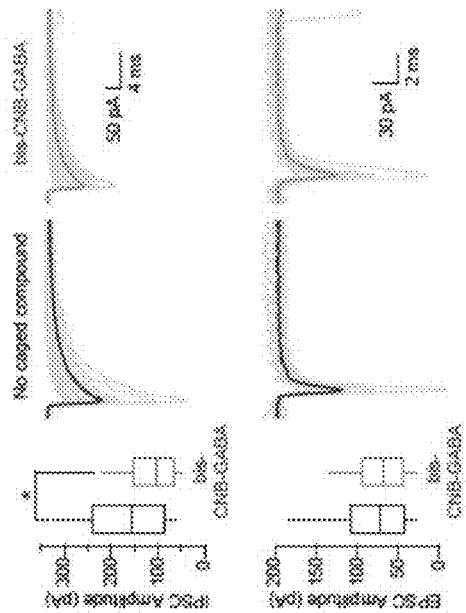
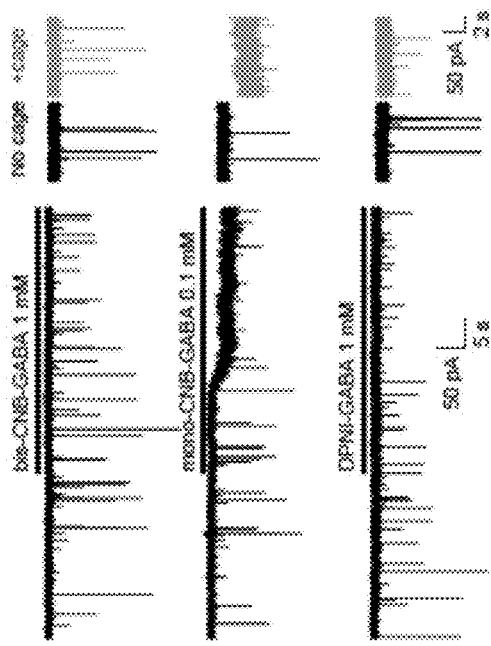
FIG. 43A
FIG. 43B
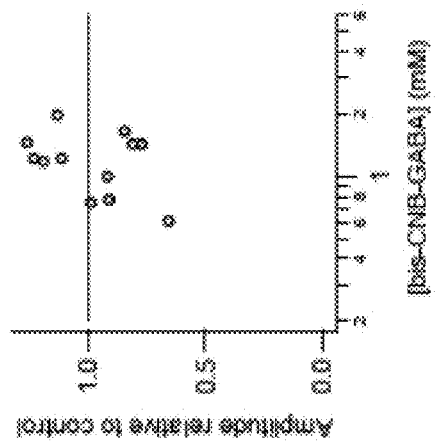
FIG. 43C
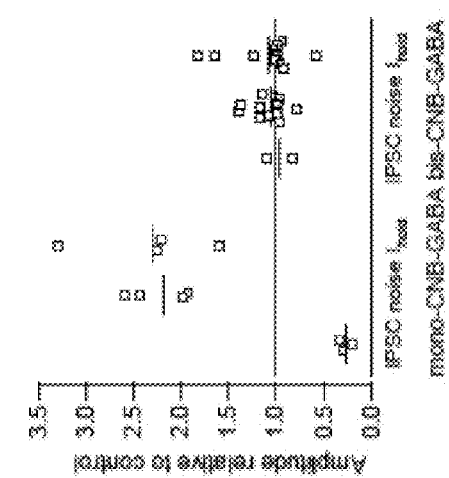
FIG. 43D
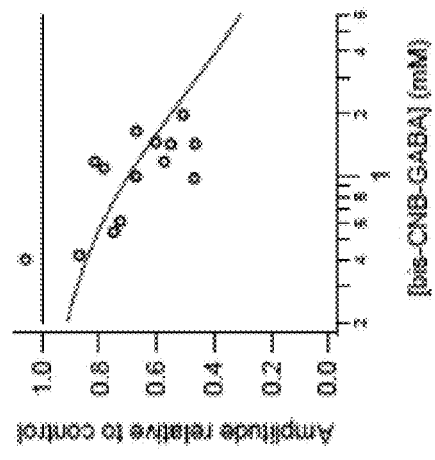
FIG. 43E

DOUBLE CAGED GABA COMPOUNDS, BIS-CNB-GABA

This application claims the benefit of U.S. Provisional Application No. 61/968,018, filed Mar. 20, 2014, and U.S. Provisional Application No. 61/993,092, filed May 14, 2014, both of which are incorporated herein by reference as if fully set forth.

This invention was made with government support under Grant No. N5045193 awarded by the National Institutes of Health, NINDS. The government has certain rights in the invention.

FIELD

The disclosure relates to double caged GABA compounds, methods of synthesis and methods of use thereof.

BACKGROUND

Caged neurotransmitters have emerged as a useful tool for the high-resolution, electrode-free chemical stimulation of single neurons or neural circuits. These probe compounds are prepared via covalent appendage of a light-sensitive protecting group—the cage—to a signaling molecule. FIG. 1 (top drawing) illustrates a single cage approach for uncaging the caged GABA compound. With the cage in place, the signaling molecule is intended to be unable to activate its receptor. Upon delivery of a pulse of light, the cage is rapidly cleaved to reveal the active signaling molecule. When introduced into sliced or intact living brain tissue, caged neurotransmitters may activate neurotransmitter pathways at defined locations with micron and millisecond precision. Because they act one level upstream from intracellular voltage and second messenger signaling, caged neurotransmitters were hoped to allow for a remarkable degree of specificity in chemical modulation of neural activity. It is possible to use patterned photostimulation techniques to achieve stimulation at many arbitrary locations in parallel; microelectrode-based methods are not amenable to this type of task (Katz, L. C.; Dalva, M. B. *J. Neurosci. Meth.* 1994, 54, 205-218; Shoham, S. et al., 3589601-1 *Nat. Methods.* 2005, 2, 837-843, which are incorporated herein by reference as if fully set forth). Moreover, neurotransmitter uncaging offers a useful alternative to optogenetic approaches because uncaging does not require gene delivery, is neurotransmitter-specific, and uses different wavelengths of light than those employed in optogenetics (Packer, A. M. et al., *Nat. Neurosci.* 2013, 16, 805-815, which is incorporated herein by reference as if fully set forth).

GABA (γ-amino butyric acid or gamma-amino butyric acid), is the chief vertebrate inhibitory neurotransmitter in mammals. It is an amino acid that contains an amino group and a carboxylic acid but due to the gamma-position of the amino group, GABA is not incorporated into proteins. GABA may be produced in inhibitory neurons from glutamate via glutamic acid decarboxylase (GAD), and may function as a neural inhibitor. GABA may agonize the GABA receptors, which act through these G-proteins to cause efflux of K+ and cause hyperpolarization of the cell (Purves et al., 2008 (Eds.). (2008). *Neuroscience* (4th ed.). Sunderland, Mass.: Sinauer Associates, Inc., which is incorporated herein by reference as if fully set forth). GABA may agonize GABA receptors that are not located only postsynaptically, but presynaptically as well. Presynaptic $GABA_B$ receptors are metabotropic receptors that suppress calcium influx, resulting in less neurotransmitter release and an overall inhibitory effect (Wang & Lambert, 1999 *Journal of Neurophysiology* 83, 1073-1078, which is incorporated herein by reference as if fully set forth).

A number of caged GABA—based compounds have been developed that satisfy many of these criteria: α-carboxy-2-nitrobenzyl (CNB)-, 4-carboxymethoxy-5,7-dinitroindolinyl (CDNI)-, 1,3-bis(dihydroxyphosphoryloxy)propan-2-yloxy]-7-nitroindoline (DPNI)-, 4-methoxy-5,7-dinitroindolinyl (MDNI)-, and ruthenium-bipyridine-triphenylphosphine-(RuBi-GABA) (Lester, H. A.; Nerbonne, J. M. *Ann. Rev. Biophys. Bioeng.* 1982, 11, 151-175; Adams, S. R.; Tsien, R. Y. *Ann. Rev. Phys.* 1993, 55, 755-784, which are incorporated herein as if fully set forth). These caged GABA compounds are chemically stable in aqueous solution on time scales of weeks or longer (Molnár, P.; Nadler, J. V. *Eur. J. Pharmacol.* 2000, 391, 255-262; Trigo, F. F. et al., *J. Neurosci. Meth.,* 2009, 181, 159-169; Matsuzaki, M. et al., *Nat. Chem. Biol.* 2010, 6, 255-257, which are incorporated by reference as if fully set forth). However, they are not inactive at GABA receptors in their caged form. CNB-, CDNI-, DPNI-, and MDNI-caged GABA compounds are antagonists of $GABA_A$ receptors, as are RuBi-GABA, the related compound RuBi-glutamate, and 4-methoxy-7-nitroindolinyl (MNI)-glutamate (Molnár, P.; Nadler, J. V. *Eur. J. Pharmacol.* 2000, 391, 255-262; Trigo, F. F. et al., *J. Neurosci. Meth.,* 2009, 181, 159-169; Matsuzaki, M. et al., *Nat. Chem. Biol.* 2010, 6, 255-257; Rial Verde, E. M. et al., *Front. Neural Circuits.* 2008, 2, 1-8; Fino, E. et al., *Front. Neural Circuits,* 2009, 3, 1-9, which are incorporated by reference as if fully set forth).

The practical limit at which these compounds can be used without interfering with neural circuit function is so low (<200 µM) that they cannot be used to attain the near-millimolar concentrations that occur locally during synaptic transmission (Perrais, D.; Ropert, N. *J. Neurosci,* 1999, 19, 578-588; Farrant, M.; Nusser, Z. *Nat. Rev. Neurosci.* 2005, 6, 215-229, both of which are incorporated by reference as if fully set forth).

SUMMARY

In an aspect, the invention relates to a composition that includes a double-caged GABA compound. The double-caged GABA compound includes a gamma-amino butyric acid covalently linked to a first photosensitive protecting group and a second photosensitive protecting group. The double-caged GABA compound is biologically inert before exposure to light. The first photosensitive protecting group and the second photosensitive protecting group cleave from the gamma-amino butyric acid by photolysis upon exposure of the double-caged GABA compound to light.

In an aspect, the invention relates to a method of synthesizing a double-caged GABA compound. The method includes conjugating a first photosensitive protecting group and a second photosensitive protecting group to a gamma-amino butyric acid.

In an aspect, the invention relates to a method of chemical stimulation of a biological sample. The method includes adding a double-caged GABA compound to the biological sample. The double-caged GABA compound includes a gamma-amino butyric acid covalently linked to a first photosensitive protecting group and a second photosensitive protecting group. The double-caged GABA compound is biologically inert before exposure to light. The first photosensitive protecting group and the second photosensitive protecting group cleave from the gamma-amino butyric acid by photolysis upon exposure of the double-caged GABA compound to light. The method also includes exposing the double-caged GABA compound in the biological sample to light.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIGS. 5A-5H illustrate functional mapping of glutamate sensitivities in hippocampal neurons. FIG. 5A illustrates fluorescence image of a neuron in culture.

FIG. 5B illustrates pseudocolor coding of the amplitude of a 2pEPSC. FIG. 5C illustrates a region of interest of the neuron shown in FIG. 5A for functional mapping. FIG. 5D illustrates a pseudocolor map of peak amplitudes of 2pEPSCs (glutamate sensitivity map). FIG. 5E illustrates a smoothed glutamate sensitivity map by linear interpolation. FIG. 5F illustrates overlay of FIG. 5C and FIG. E. FIG. 5G illustrates a FM143 fluorescence image. FIG. 5H illustrates an overlay of FIG. 5E and FIG. 5G.

FIG. 7A illustrates layer 2/3 pyramidal cell filled with Alexa 594 dye. FIG. 7B illustrates uncaging spots (white) along the selected dendrite. FIG. 7C illustrates average individual uncaging responses at the soma. FIG. 7D illustrates somatic responses to IN and OUT directions at 2.3 mm/ms. FIG. 7E illustrates plot comparing peak amplitudes for IN and OUT sequences at the optimal velocity for direction selectivity. FIG. 7F illustrates direction-selective responses at different velocities. FIG. 7H illustrates relation between peak voltage and input velocity (values normalized to the maximum response in the IN direction for each cell (n=15).

FIGS. 8A-8E illustrate theoretical improvements in spatial resolution of chemical two-photon uncaging. FIG. 8A illustrates a scheme of chemical two-photon uncaging using GABA as the neurotransmitter substrate. FIG. 8B illustrates structure of bis-CNB-glutamate. FIG. 8C illustrates focal shape and light intensity of laser. FIG. 8D illustrates expected release of glutamate in single-caged and double-caged glutamate. FIG. 8E illustrates predicted improvements in axial resolution in single-caged and double-caged glutamate.

FIGS. 9A-9C illustrate experimental improvements in spatial resolution of chemical two-photon uncaging. FIG. 9A illustrates current traces evoked by single- and double-caged glutamate (5 ms flashes at 10 s intervals) obtained while varying the distance between the neuronal cell body and the focal plane of the UV light beam. FIG. 9B illustrates a relationship between light energy and peak amplitude of currents evoked in individual pyramidal neurons by single-caged (closed circles) or double-caged (open circles) glutamate. FIG. 9C illustrates a relationship between axial position and the peak currents shown in top left.

FIG. 11A illustrates typical responses to uncaging in spiny dendrites of 100 mM double-caged (dc) $IP_3$. FIG. 11B illustrates 100 mM single-caged (sc) $IP_3$. FIG. 11C illustrates 300 mM single-caged $IP_3$, FIG. 11D illustrates 100 mM caged gPIP.

FIGS. 13A-13B illustrate caged amines. FIG. 13A illustrates a scheme of caging via a carbamate linker (left) and structure of nitrobenzyl-caged amine with a carba-mate. FIG. 13B illustrates a scheme of direct caging on amine (left) and structure of nitrobenzylcaged amine via direct caging.

FIG. 16 illustrates quantum yields of release of p-hydroxyphenacyl (pHP) cages, highlighting the range of quantum yields depending on the substrate caged.

FIG. 21 illustrates cage groups derived from coumarin.

FIG. 22 illustrates uncaging scheme of RuBi-GABA.

FIG. 23 illustrates a scheme of bis-CNB-GABA.

FIG. 24 illustrates structure of CDNI-GABA.

FIG. 25A illustrates that increasing the concentration of CNB-GABA progressively reduced the peak amplitude of the response recorded at a holding potential of 0 mV. FIG. 25B illustrates a cumulative concentration-response curve.

FIGS. 38A-38C illustrate uncaging with 405 nm laser at three different locations. FIG. 38D illustrates uncaging with 365 nm LED laser.

FIG. 39 illustrates that bis-CNB-GABA has no significant effect on spontaneously-evoked AMPA currents (raw traces: top right, summary: top left) and exhibits ~33% reduction of GABA currents (raw traces: bottom right, summary: bottom left).

FIG. 40A-40B illustrate caged dopamine and serotonin. FIG. 40A illustrates dopamine (left) caged with NPE (right). FIG. 40B illustrates serotonin (left) caged with NPE (right).

FIGS. 42A-42E illustrate physiological responses to photolysis of bis-CNB-GABA.

FIG. 42A illustrates a cerebellar molecular layer interneuron visualized using Alexa 488 in the patch recording electrode solution. FIG. 42B illustrates bis-CNB-GABA (1.4 mM) was photolyzed with a 3650 nm LED at progressively higher flash energies (0.25-1.1 mW, 5-50 ms, 1.25-55 µJ). FIG. 42C illustrates the same experiment as shown in FIG. 42B with Responses to mono-CNB-GABA (50 µM). FIG. 42D illustrates normalized current as a function of relative LED flash energies plotted on a log-log scale. FIG. 42E illustrates laser-evoked whole-cell current recorded in the absence and presence of 3 µM gabazine, a GABAA receptor antagonist.

FIGS. 43A-43E illustrate quantification of unwanted effects of caged GABA. FIG. 43A illustrates voltage-clamp recordings from cerebellar interneurons exposed to caged GABA. FIG. 43B illustrates effects of caged GABA on spontaneous IPSCs and excitatory postsynaptic currents (EPSCs). FIG. 43C illustrates dependence of spontaneous IPSC amplitude on bis-CNB-GABA concentration. FIG. 43D illustrates comparison of effects of mono-O-CNB-GABA (0.1 mM) and bis-CNB-GABA (1.0 mM, except for 0.4 mM for IPSCs) on spontaneous IPSC amplitude, standard deviation of holding current (noise), and holding current ($I_{hold}$). FIG. 43E illustrates spontaneous EPSC size was unaffected by bis-CNB-GABA at all concentrations tested.

FIG. 44A illustrates $^1$H NMR data used to quantify GABA accumulation. FIG. 44B illustrates that in aqueous solutions in the light, accumulation of photoproducts from bis-CNB-GABA (black) and GABA from mono-CNB-GABA (gray). Error bars indicate SD.

DETAILED DESCRIPTION OF THE PREFERRED EMBODIMENTS

Figure 1:
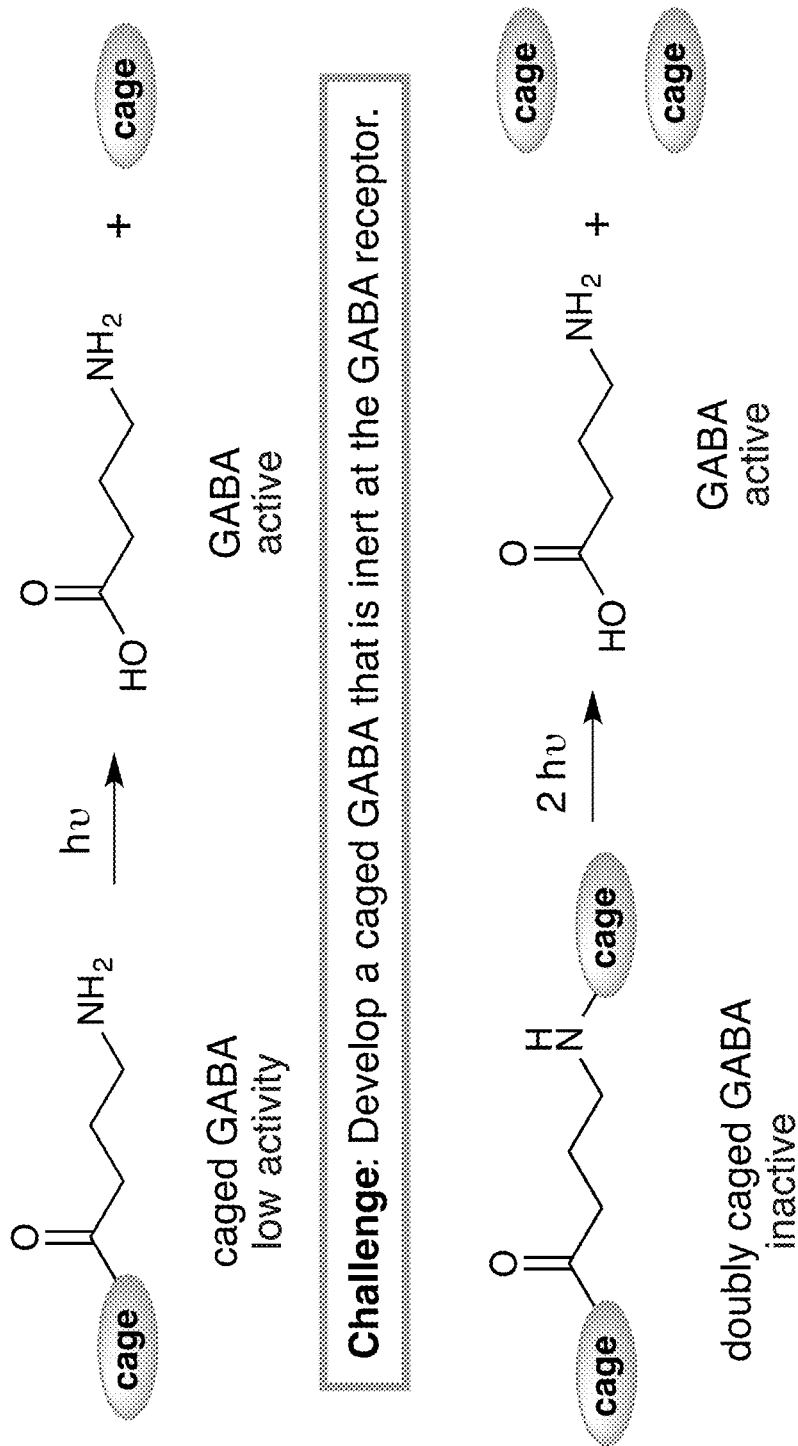
FIG. 1 illustrates uncaging schemes for single-caged GABA (top), and chemical two-photon uncaging of double-caged GABA (bottom).

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

An embodiment provides a double-caged GABA compound that includes a gamma-amino butyric acid covalently linked to a first photosensitive protecting group and a second photosensitive protecting group. A photosensitive protecting group is also referred to herein as a cage. The double-caged GABA may be biologically inert before exposure to light. The first photosensitive protecting group and the second photosensitive protecting group may cleave from the gamma-amino butyric acid by photolysis upon exposure of the double-caged GABA compound to light.

In an embodiment, the first photosensitive protecting group may be linked to the carboxyl of the gamma-amino butyric acid. The second photosensitive protecting group may be linked to the amine of the gamma-amino butyric acid. As used herein, the first photosensitive protecting group or the second photosensitive protecting group is also referred to as a "cage," or "caging group." A compound modified with a photosensitive protecting group may be referred to as a "caged compound."

The first photosensitive protecting group may be but is not limited to a nitrobenzyl, nitroindoline, carboxymethoxydinitroindoline, coumarin, or ruthenium group, or any photosensitive derivative thereof. The photosensitive derivative of nitrobenzyl may be but is not limited to nitrophenyl ethyl (NPE), α-carboxy-2-nitrobenzyl (CNB), 4,5-dimetoxy-2-nitrobenzyl (DMNB), or 4,5-dimethoxy-2-nitrophenyl)ethyl (DMNPE). The photosensitive derivative of nitroindoline may be but is not limited to 4-methoxy-7-nitroindoline (MNI) or 4-carboxymethoxy-5,7-dinitroindolinyl (CDNI). The photosensitive derivative of coumarin may be but is not limited to 6-bromo-7-hydroxycoumarin-4-ylmethoxycarbonyl (Bhc). The photosensitive derivative of ruthenium may be but is not limited to ruthenium-bipyridine-triphenylphosphine (RuBi). The first photosensitive protecting group may be but is not limited to nitrobenzyl (NB), nitrophenyl ethyl (NPE), α-carboxy-2-nitrobenzyl (CNB), 4,5-dimetoxy-2-nitrobenzyl (DMNB), 4,5-dimethoxy-2-nitrophenyl)ethyl (DMNPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), or carboxynitrobenzyl. The second photosensitive protecting group may be but is not limited to a nitrobenzyl, nitroindoline, carboxymethoxydinitroindoline, coumarin, or ruthenium group, or any photosensitive derivative thereof. The second photosensitive protecting group may be but is not limited to nitrobenzyl (NB), nitrophenyl ethyl (NPE), α-carboxy-2-nitrobenzyl (CNB), 4,5-dimetoxy-2-nitrobenzyl (DMNB), 4,5-dimethoxy-2-nitrophenyl)ethyl (DMNPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), or carboxynitrobenzyl. The nitrobenzyl, nitroindolinyl, carboxymethoxy-dinitroindolinyl, coumarin, nitrobenzyl, coumarin or ruthenium group or any derivative thereof may be capable to cleave from the caged compound.

The group selected as the first photosensitive protecting group may be the same type or a different type than the group as selected the second photosensitive protecting group.

In an embodiment, the first photosensitive protecting group or the second photosensitive protecting group may be any group that satisfies the properties for ideal photosensitive protecting groups. The ideal caged GABA neurotransmitter may exhibit the properties of: (1) inertness at the receptor; (2) high combined extinction coefficient and quantum yield; (3) ability to undergo rapid cleavage to unveil the active neurotransmitter with few side products; and (4) chemical stability in aqueous solution.

The first photosensitive protecting group or the second photosensitive protecting group may be chosen such that the substrate undergoes two-photon excitation. The substrate may be gamma-amino butyric acid.

The first photosensitive protecting group or the second photosensitive protecting group may be any group that satisfies a requirement for temporal efficiency. The group that satisfies the requirement for temporal efficiency may be used for linking to a neurotnsmitter. The doubled-caged GABA may be added to the brain tissues. The double-caged GABA may be exposed to light. As used herein, the term "temporal efficiency" refers to rapid cleavage of the caged neurotransmitter in a specific location of the brain tissue upon exposure to light. The first photosensitive protecting group or the second photosensitive protecting group of the double-caged GABA may be capable of rapid photocleavage upon exposure to light and release of the gamma-amino butyric acid. The gamma-amino butyric acid may be released from the double-caged GABA compound at a rapid release rate of $10^4$ and $10^{13}$ gamma-amino butyric acid moieties released per millisecond. If the light is generated by the laser, the double-caged GABA may undergo photolysis only at the area targeted by the laser. The rapid release rate of the gamma-aminobutyric acid may lead to high spatial resolution of the double-caged GABA in a specific location of the brain. The uncaged neurotransmitter may diffuse little or not at all to surrounding areas of the tissue and may cause nor larger or little larger an area of stimulation than originally intended. Uncaging, or release, of the first photosensitive protecting group or the second photosensitive protecting group from the double-caged GABA may occur fast enough so that diffusion would not significantly affect the area of substrate release.

In an embodiment, the first photosensitive protecting group or the second photosensitive protecting group may be any group that is accessible to the bond formation between the cage and the substrate.

In an embodiment, the first photosensitive protecting group or the second photosensitive protecting group may be any group that satisfies useful properties for solubility for caged neurotransmitters. Useful caged neurotransmitters have high solubility in the solution used to bathe the brain slice. The solution may be the artificial cerebrospinal fluid (ACSF) or other aqueous solutions. Uncaging using two-photon excitation may require high concentrations of a caged compound, typically in the mM range. Therefore, any double-caged GABA compound described herein may be soluble in an aqueous solution. The aqueous solution may be water. The aqueous solution may be ACSF. The aqueous solution may be a buffer. The buffer may be HEPES, bicarbonate buffer, or any other suitable pH buffer. The first photosensitive protecting group or the second photosensitive protecting group may be any group designed to satisfy the high solubility property. The first photosensitive protecting group or the second photosensitive protecting group may have additional functional groups that help increase solubility. Non-limiting examples of groups that increase solubility include the carboxylate groups on nitrobenzyl derivatives and CDNI.

The first caging group or the second caging group may be any group that satisfies the property of being inert before photolysis. A caged compound depends on rapid introduction of the substrate through photorelease and a cage's substrate release has to be controlled by the experimenter. Therefore, the first caging group or the second caging group of the caged compound may release its substrate only upon light exposure, and no sooner. The first caging group or the second caging group of the caged compound may be chosen such that the caged compound does not agonize, or agonizes its substrate's receptors. This would allow the experimenter to control stimulation with temporal or spatial specificity.

The first photosensitive protecting group or any byproduct thereof and the second photosensitive protecting group or any byproduct thereof may be biologically inert after exposure to light and cleavage from the double-caged GABA compound. Inertness of photosensitive protecting groups or byproducts after uncaging may be equally important as inertness before uncaging. Photolysis may result in release of the substrate (GABA), and also of the cage groups. The cage groups may be chosen such that they or their cleavage byproducts do not contribute to any unwanted side activity following uncaging of the caged substrate.

The first photosensitive caging group or the second first photosensitive group may be any group that satisfies the property of having a high extinction coefficient. Because light activation initiates photolysis, the caging group may be any group that absorbs light efficiently. As used herein, the term "extinction coefficient" refers to the coefficient ($\epsilon$) that quantifies how well a compound absorbs light at a specific wavelength and is derived from the Beer-Lambert Law:

$$A = c\epsilon l,$$

where A represents absorbance, c is the concentration of the caged compounds, and l is the distance the light travels through the solution of compound. Extinction coefficient is expressed in $M^{-1}$ $cm^{-1}$. In an embodiment of double-caged GABA compound herein, at least one of the first photosensitive protecting group or the second photosensitive protecting group has an extinction coefficient greater than 1,000 $M^{-1}$ $cm^{-1}$. At least one of the first photosensitive protecting group or the second photosensitive protecting group may have an extinction coefficient from 1,000 $M^{-1}$ $cm^{-1}$ to 60,000 $M^{-1}$ $cm^{-1}$. The foregoing extinction coefficient range may be subdivided. The extinction coefficient of the first photosensitive protecting group or the second photosensitive protecting may be a value in a sub-range between any two values chosen from 1,000 $M^{-1}$ $cm^{-1}$ increments within the above-described ranges (endpoints inclusive).

In an embodiment, the first photosensitive caging group or the second first photosensitive group may be any group that satisfies the property of having a wavelength of maximal absorption ($\lambda_{max}$) in a useful range. Light with wavelengths shorter than the UV range can often cause photodamage to neural tissue. At least one of the first photosensitive caging group or the second first photosensitive group may be any group that is highly efficient at absorbing light. The light may be of low enough energy such that is not be damaging to neural tissue. The first photosensitive caging group or the second first photosensitive group may have a lower limit of light absorption of 250 nm in order to be in a useful range. At least one of the first photosensitive caging group or the second first photosensitive group may have $\lambda_{max}$ values upwards of 350 nm. At least one of the first photosensitive caging group or the second first photosensitive group may have a wavelength of maximal absorption from to 250 nm to 500 nm. The wavelength of maximal absorption ($\lambda_{max}$) of the first photosensitive protecting group or the second photosensitive protecting may be a value in a subrange between any two values chosen from 10 increments within the above-described ranges (endpoints inclusive). Because extinction coefficient is reflective of the ability of the cage itself (as opposed to the substrate) to absorb light, its value may be independent of the substrate being caged. The first photosensitive caging group or the second first photosensitive group may incorporate chromophores that are effective at absorbing light. The chromophores may be substituted aryl rings. The first photosensitive caging group or the second first photosensitive group that incorporate chromophores may also be optimized for aqueous solubility.

The first photosensitive protecting group or the second photosensitive protecting group may be any group that satisfies the property of having a high quantum yield. As used herein, the term "quantum yield" ($\phi$) characterizes the ability for a caged compound to release its substrate upon successful absorption of a photon. Quantum yield is equal to the proportion of molecules that undergo successful photolysis to release the substrate after photon absorption. Quantum yield is unitless and theoretically ranges from 0 to 1, with 1 representing perfect efficiency of photolysis upon light absorption. At least one of the first photosensitive protecting group or the second photosensitive protecting group may have a quantum yield from 0.005 to 1.0 or 0.005 to 0.7. Each of the foregoing quantum yield ranges may be subdivided. The quantum yield of the first photosensitive protecting group or the second photosensitive protecting may be a value in a subrange between any two values chosen from 0.005 increments within the above-described ranges (endpoints inclusive). The quantum yield may be the number of successful cleavages of the respective photosensitive protecting group from the gamma-amino butyric acid per photon absorbed. The first photosensitive protecting group or the second photosensitive protecting group may be any one of the commonly used photosensitive protecting groups that have quantum yield in a range of 0.005 (DMNB) to 0.7 (NDBF). The commonly used photosensitive protecting group may have quantum yield in the 0.05 to 0.3 range.

In an embodiment, at least one of the first photoprotective group or the second photoprotective groups may be any group that has a high extinction coefficient and a high quantum yield. The former quantifies how well a compound absorbs light, while the latter characterizes how efficiently the cage will cleave after absorption of that light. Both may be important for adequate substrate release. The product of extinction coefficient and quantum yield may exceed 300 $M^{-1}$ $cm^{-1}$. A cage may be optimized to absorb light with a subsequently high extinction coefficient. However, if the quantum yield of this compound is too low, then even maximal amounts of light absorbance will only result in minimal amounts of successful photocleavage. Similarly, it may possible for a cage to cleave with perfect efficiency ($\phi$=1), meaning that every photon absorbed will result in successful photocleavage. However, if the compound does not absorb enough light (low $\epsilon$), little substrate will be released despite the perfect quantum yield. Therefore, the photosensitive protective groups may be optimized to have a balanced extinction coefficient and quantum yield.

In an embodiment, at least one of the first photosensitive protecting group or the second photosensitive protecting group may have an extinction coefficient greater than 1,000 $M^{-1}$ $cm^{-1}$, and at least one of the first photosensitive protecting group or the second photosensitive protecting group may have a quantum yield from 0.005 to 1.0. A product of the extinction coefficient and the quantum yield for the first photosensitive protecting group may exceed 300 $M^{-1}$ $cm^{-1}$, and a product of the extinction coefficient and the quantum yield for the second photosensitive protecting group may exceed 300 $M^{-1}$ $cm^{-1}$. At least one of the first photosensitive protecting group or the second photosensitive protecting group may have an extinction coefficient from 1,000 $M^{-1}$ $cm^{-1}$ to 60,000 $M^{-1}$ $cm^{-1}$. At least one of the first photosensitive protecting group or the second photosensitive protecting group may have a quantum yield from 0.005 to 0.7. Each of the foregoing extinction coefficient and quantum yield ranges may be subdivided. The extinction coefficient of the first photosensitive protecting group or the second photosensitive protecting may be a value in a subrange between any two values chosen from 1,000 $M^{-1}$ $cm^{-1}$ increments within the above-described ranges (endpoints inclusive). The quantum yield of the first photosensitive protecting group or the second photosensitive protecting may be subdivided between any two values chosen from 0.005 increments within the described ranges (endpoints inclusive).

In an embodiment, at least one of the first photosensitive protecting group or the second photosensitive protecting group may be any group that has a high solubility in an aqueous solution, high quantum yield, and successful photocleavage from a wide range of functional groups.

In an embodiment, at least one of the first photosensitive protecting group or the second photosensitive protecting group may be a nitrobenzyl cage. The nitrobenzyl cage may be the 2-nitrobenzyl cage (NB). The nitrobenzyl cages herein may be used to cage a range of functional groups, including alcohols, phosphates, carboxylates, and amines. The nitrobenzyl cages may be adequately soluble for physiological use. The nitrobenzyl cages may undergo rapid cleavage in the microsecond timescale when caging a carboxylate, making them suitable for a range of physiological usage.

Figure 17:
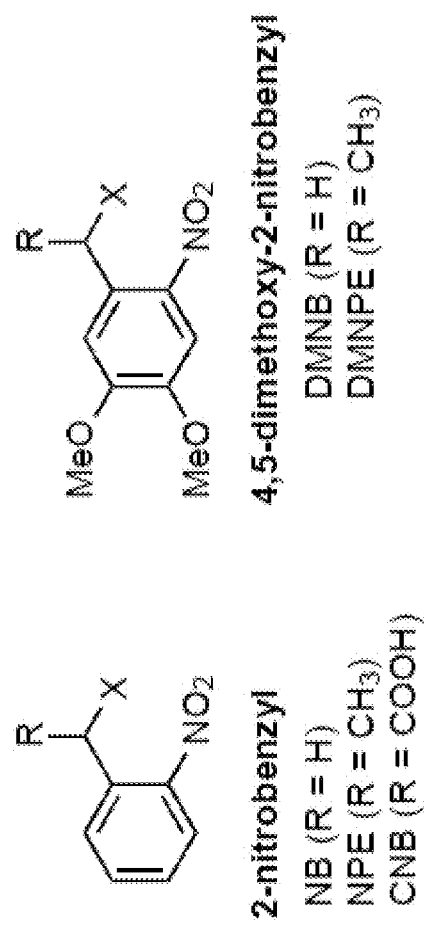
FIG. 17 illustrates cages based on 2-nitrobenzyl.
Figure 20:
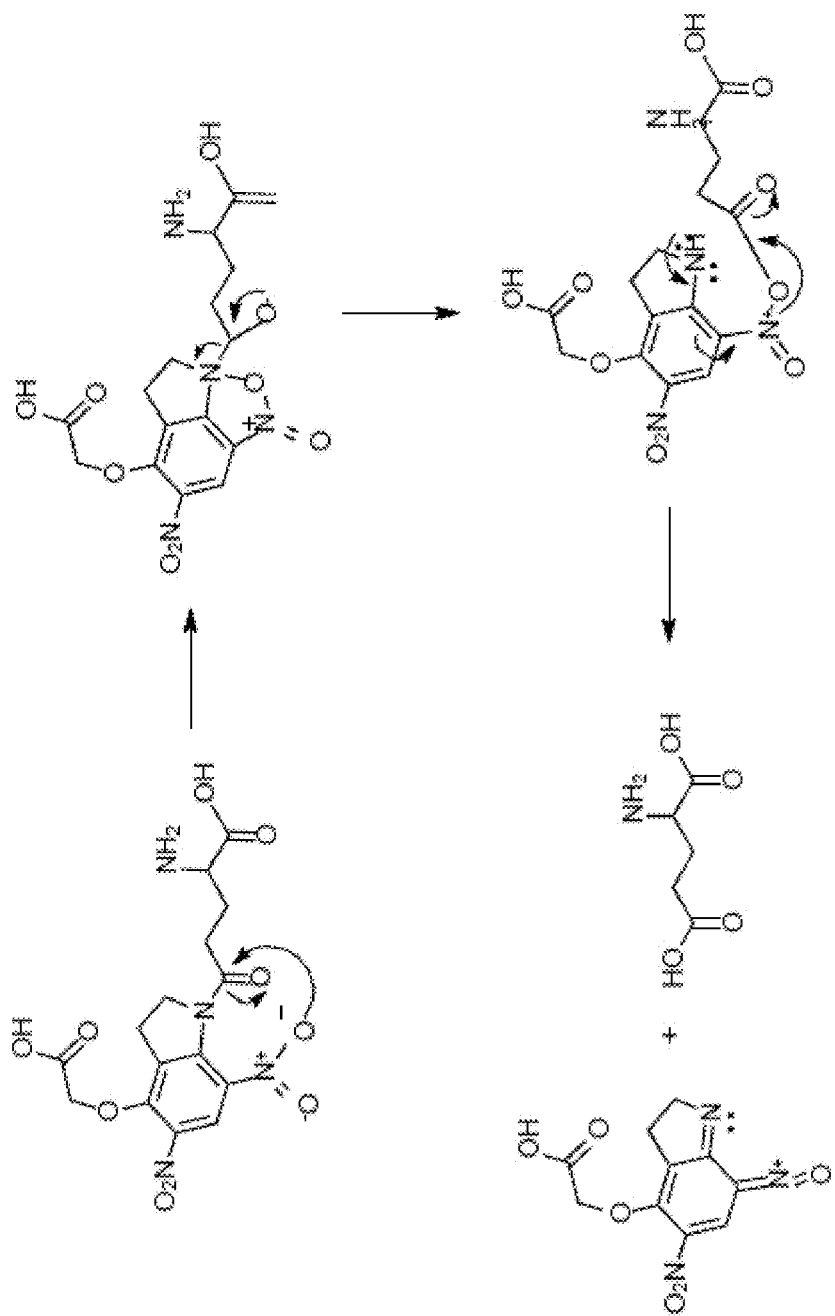
FIG. 20 illustrates a photolysis mechanism of nitroindoline cages, illustrated with CDNI-glutamate.

At least one of the first photosensitive protecting group or the second protecting group may be a nitrobenzyl group derivatized to generate several different types of nitrobenzyl cages. FIG. 17 illustrates derivatized nitrobenzyl groups that may be a cage herein. Referring to FIG. 17, R included in 1-nitrobenzyl may be hydrogen (H) (nitrobenzyl, NB), methyl ($CH_3$) (nitrophenyl ethyl, NPE) or carboxyl (COOH) ($\alpha$-carboxy-2-nitrobenzyl, CNB). Still referring to FIG. 17, R included in 4,5-dimetoxy-2-nitrobenzyl may be hydrogen (H) (DMNB), or methyl ($CH_3$)(4,5-dimethoxy-2-nitrophenyl)ethyl, DMNPE). FIG. 20 illustrates the uncaging mechanism for the derivatized nitrobenzyl photosensititive protecting groups. Referring to FIG. 20, an uncaging mechanism for these groups that may proceed through a cyclized intermediate and may depend on solvent and pH.

At least one of the first photosensitive protecting group or the second photosensitive protecting group may be the α-carboxy-2-nitrobenzyl (CNB). CNB ($\epsilon$ 5,100 $M^{-1}$ $cm^{-1}$ at 262 nm) exhibits a high quantum yield when used to cage glutamate at the carboxylate ($\phi$=0.16). The CNB may be capable of caging a range of functional groups. The CNB may be stable in aqueous solutions and may lack of toxic byproducts.

In an embodiment, at least one of the first photosensitive protecting group or the second photosensitive protecting group may be the nitroindoline cage. The nitroindoline cage may be useful for achieving high-resolution photostimulation because this type of cages exhibit two-photon sensitivity and can be used in the two-photon excitation system.

Figure 19:
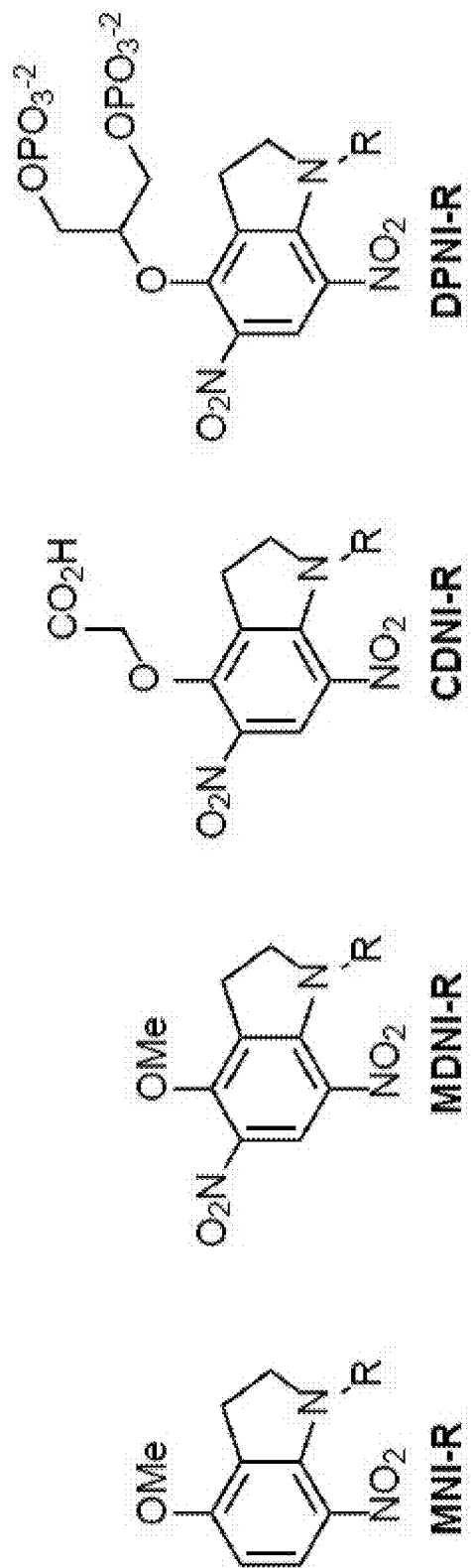
FIG. 19 illustrates cage groups derived from nitroindoline.

The nitroindoline cages may have two-photon sensitivity, rapid kinetics, and aqueous solubility. The nitroindoline cages may be used to cage carboxylate functional groups. When synthetically accessible, the nitroindoline cages may exhibit sufficient two-photon sensitivity and may be used to achieve non-linear spatial resolution. FIG. 19 illustrates photosensitive protecting groups, or cages, derived from nitroindoline. Referring to FIG. 19, the nitroindoline cage may be 4-methoxy-7-nitroindoline (MNI). The nitroindoline cage may be 4-carboxymethoxy-5,7-dinitroindolinyl (CDNI). CDNI may improve quantum yield and may also undergo successful two-photon uncaging. The first photosensitive protecting group or the second or the second photosensitive group may be a coumarin cage. The coumarin cage may be a cage group with two-photon sensitivity. The coumarin cage may be any cage illustrated in FIG. 21. Referring to FIG. 21, the coumarin groups may be used to cage a range of functional groups, including carboxylates, diols, sulfates, ketones and aldehydes, alcohols, thiols, and amines. Coumarin-based cages may be used for caging phosphate, such as caged cAMP, RNA, and DNA. The ability to cage on carboxylates and amines may be useful for neuroscientists.

Figure 14:
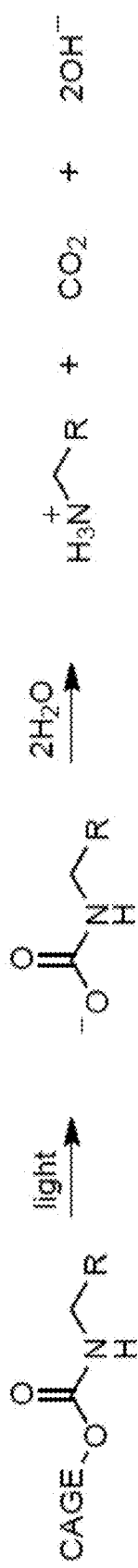
FIG. 14 illustrates photolysis of carbamate-caged amines.

The coumarin cage may be 6-bromo-7-hydroxycoumarin-4-ylmethoxycarbonyl (Bhc). The Bhc cage may be used to photoprotect gamma-amino butyric acid at both the carboxylate and the amine through a carbamate linker. Bhc-glutamate exhibits very efficient absorption ($\epsilon=19,550$ $M^{-1}$ $cm^{-1}$ at 369 nm) but modest quantum yield ($\phi=0.019$, $\phi\times=371$ $M^{-1}$ $cm^{-1}$). When caged on the amine, the photochemical properties may remain quite similar ($\epsilon=17,470$ $M^{-1}$ $cm^{-1}$ at 368 nm, $\phi=0.019$, $\phi\times\epsilon=331$ $M^{-1}$ $cm^{-1}$). In addition, Bhc may be stable to aqueous hydrolysis and may also exhibit high two-photon cross sections, allowing 2PE to be applied for highly localized photolysis. FIG. 14 illustrates photolysis of carbamate-caged amines. In addition, Bhc may be highly fluorescent, which may allow photolysis of the compound to be easily measured.

At least one of the first photosensitive protecting group or the second photosensitive group may be a ruthenium cage. The ruthenium cage may be ruthenium-bipyridine-triphenyl-phosphine (RuBi). RuBi may be photolyzed at visible light wavelengths.

At least one of the first photosensitive protecting group or the second photosensitive protecting group may be any other cage group satisfying optimization requirements. The optimization requirements may include factors such as synthetic accessibility, activity before photolysis, and the kinetics of the biological events being probed.

In an embodiment, the double-caged GABA compound may be bis-CNB-GABA and may have the structure of Formula I:

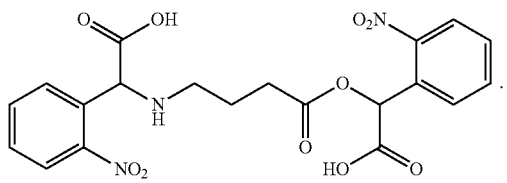

Formula I

The double-caged GABA compound may be a bioactive derivative of bis-CNB-GABA. The double-caged GABA compound may be a salt of bis-CNB-GABA. The salt of bis-CNB-GABA may include any anion. The anion may be Cl or TFA.

In an embodiment a composition that includes a double-caged GABA compound is provided. The composition may include any double-caged GABA compound described herein. The composition may include an artificial cerebrospinal fluid (ACSF). The composition may include a biological aqueous buffer. The buffer may be HEPES. The buffer may be bicarbonate buffer, or any other suitable pH buffer.

In an embodiment, a method of synthesizing a double-caged GABA compound is provided. The method may include conjugating a first photosensitive protecting group and a second photosensitive protecting group to a gamma-amino butyric acid. The first photosensitive protecting group may be conjugated to the carboxyl of the gamma-amino butyric acid. The second photosensitive protecting group may be conjugated to the amine of the gamma-amino butyric acid. The first photosensitive protecting group and the second photosensitive protecting groups may be simultaneously conjugated to the gamma-amino butyric acid at the carboxy position and the amine position, respectively. Prior to conjugating the first photosensitive protecting group and the second photosensitive protecting groups may be included in an intermediate compound. The step of conjugating may include combining the intermediate compound and the gamma-amino butyric acid in a solvent to form a mixture. The step of conjugating may also include providing an inert gas over the mixture. As used herein, an intermediate compound is a compound, which is produced in the course of a chemical synthesis, which is not itself the final product, but is used in further reactions which produce the final product. In an embodiment, the intermediate compound may be benzyl bromide.

Figure 31:
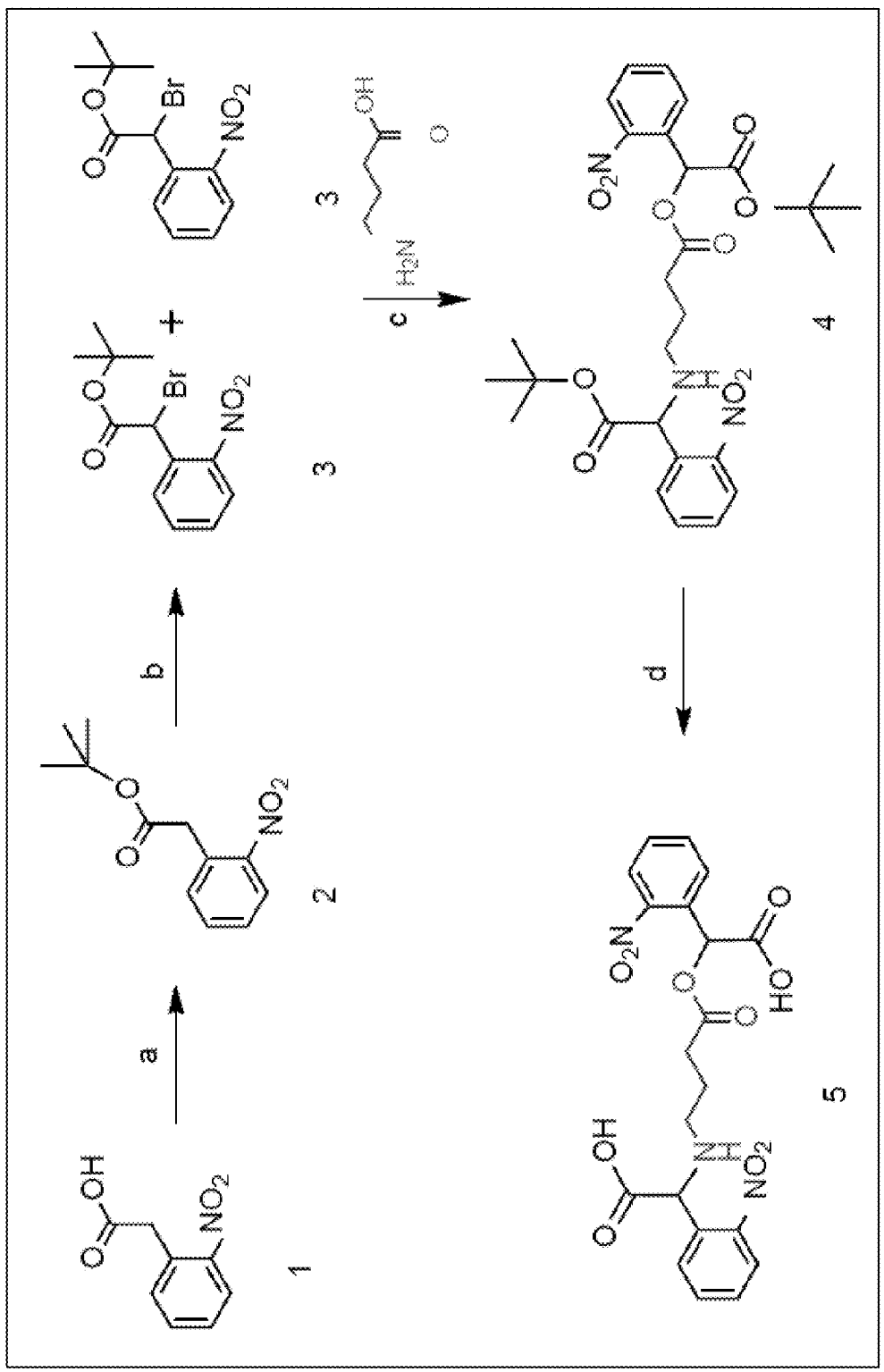
FIG. 31 illustrates a synthesis scheme for bis-(alpha-carboxy-2-nitrobenzyl)-GABA (bis-CNB-GABA) using one-step addition of both cage precursors.

FIG. 31 illustrates a method of synthesizing double-caged GABA. Referring to FIG. 31, in step (a), under nitrogen, nitrophenylacetic acid (1) was combined with tert-butanol to obtain tert-Butyl 2-(2-nitrophenyl)acetate (2); in step (b), under nitrogen, tert-Butyl 2-(2-nitrophenyl)acetate (2) was combined with N-bromo succinimide (NBS), azobisisobutyronitrile (AIBN) and carbon tetrachloride to produce tert-Butyl 2-bromo-2-(2-nitrophenyl)acetate (3); in step (c) tert-Butyl 2-bromo-2-(2-nitrophenyl)acetate (3) was combined with γ-aminobutyric acid in dimethylformamide (DMF) under nitrogen, the potassium carbonate and water were added, and the product was extracted with ethyl acetate (EtOAc), dried with $NaSO_4$ to obtain the bis-CNB-GABA precursor 2-(tert-Butoxy)-1-(2-nitrophenyl)-2-oxoethyl 4-((2-(tert-butoxy)-1-(2-nitrophenyl)-2-oxoethyl)amino)butanoate (4); in step (d) 2-(tert-Butoxy)-1-(2-nitrophenyl)-2-oxoethyl 4-((2-(tert-butoxy)-1-(2-nitrophenyl)-2-oxoethyl) amino) butanoate (4) was combined with trifluoroacetic acid (TFA) in dichloromethane (DCM) under nitrogen to produce 2-((4-(Carboxy(2-nitrophenyl)methoxy)-4-oxobutyl) amino)-2-(2-nitrophenyl)acetic acid, bis-CNB-GABA (5). A non-limiting example follows.

In an example, tert-Butyl 2-(2-nitrophenyl)acetate (2) was produced. Under nitrogen, tert-butanol (100 mL) was added to commercially available nitrophenylacetic acid (4.0 g, 22.1 mmol) and the mixture was stirred until clear. Di-tert-butyl dicarbonate (9.64 g, 44.2 mmol) was added and the mixture was stirred until dissolved. DMAP (0.8 g, 6.5 mmol) was then added, and the reaction mixture was stirred for one h at room temperature. The solvent was evaporated to generate a dark brown oil. The oil was purified by filtration through a plug of silica gel on a fritted glass funnel [$SiO_2$, EtOAc/hexane (1:9)] to generate the product, a yellow oil (4.672 g, 89% yield).

tert-Butyl 2-bromo-2-(2-nitrophenyl)acetate (3) was produced by combining tert-Butyl 2-(2-nitrophenyl)acetate (2) (5.08 g, 21.4 mmol), NBS (4.00 g, 22.5 mmol), and AIBN (0.528 g, 3.21 mmol) under nitrogen with carbon tetrachloride (35 mL) and heated at reflux overnight. The reaction mixture was then cooled, filtered, and concentrated. The residue was purified by column chromatography [$SiO_2$, hexane/toluene (1:4)] to obtain the desired product (3.91 g, 64%).

2-(tert-Butoxy)-1-(2-nitrophenyl)-2-oxoethyl 4-((2-(tert-butoxy)-1-(2-nitrophenyl)-2-oxoethyl)amino)butanoate (4) was produced by combining tert-Butyl 2-bromo-2-(2-nitrophenyl)acetate (3) (1.48 g, 4.68 mmol) with γ-aminobutyric acid (226.4 mg, 2.20 mmol) in DMF (16 mL) under nitrogen. Potassium carbonate (481.9 mg, 3.487 mmol) was then added, and the reaction mixture was stirred at 65° C. for 36 h. Water was added and the product was extracted with EtOAc, dried with $NaSO_4$, and concentrated. The resulting material was purified by column chromatography [$SiO_2$, hexane/EtOAc (6:1)] to give the product (850 mg, 68%). The $^{13}C$ NMR spectrum indicated the presence of diastereomers arising from the two benzylic stereocenters in the bis-CNB-GABA precursor.

2-((4-(Carboxy(2-nitrophenyl)methoxy)-4-oxobutyl)amino)-2-(2-nitrophenyl)acetic acid, bis-CNB-GABA (5) was produced by combining 2-(tert-Butoxy)-1-(2-nitrophenyl)-2-oxoethyl 4-((2-(tert-butoxy)-1-(2-nitrophenyl)-2-oxoethyl)amino) butanoate (4) (436 mg, 0.76 mmol) with TFA (2.94 mL, 38.4 mmol) in DCM (10 mL) under nitrogen. The reaction mixture was stirred for 5 h, and a second portion of TFA was added (2.94 mL, 38.4 mmol). A final portion of TFA (29.4 mL, 38.4 mmol) was added after 22 additional hours of stirring. The reaction mixture was concentrated, and the residue was purified by HPLC. The $^{13}C$ NMR indicated the presence of diastereomers arising from the two benzylic stereocenters in the bis-CNB-GABA.

In an embodiment, the method may include allowing the mixture to react for 1 hour to 25 hours. The reaction may be allowed to proceed from 1 to 5 hours, from 5 hours to 10 hours, from 10 hours to 15 hours, from 15 hours to 20 hours, and from 20 hours to 25 hours. The time period for reaction may be in a range between any two integer value between 1 hour and 25 hours. The reaction may be allowed to proceed for 1 hour.

In an embodiment, the method may further include maintaining the mixture at a temperature of 20° C. to 65° C. The temperature may be in a range between any two integer value temperatures selected from 20° C. to 65° C. The temperature may be in a range between and including 20° C. and 30° C., 30° C. and 40° C., 40° C. and 50° C., 50° C. and 60° C., and 60° C. and 75° C. The temperature may be any one integer value temperature selected from those including and between 20° C. and 65° C. Temperatures between room temperature and 65° C. may be used. The temperature may be any one temperature including and between room temperature and 65° C. Temperatures between 25° C. and 65° C. may be used. The temperature may be any temperature including and between 25° C. and 65° C. The temperature may be 65° C.

In an embodiment, the first photosensitive protecting group and the second photosensitive protecting group may be conjugated to the gamma-amino butyric acid sequentially. The first photosensitive protecting group may be conjugated to carboxyl of the gamma-amino butyric acid to form a mono-caged-gamma-aminobutyric acid. The first photosensitive protecting group may be conjugated to the amine of the mono-caged gamma-amino butyric acid. The first photosensitive protecting group may be any photosensitive protecting group described herein. The second photosensitive protecting group may be any photosensitive protecting group described herein. Methods of synthesis may include adding protecting groups, or removing them at appropriate stages of the synthesis.

In an embodiment a method of chemical stimulation of a biological sample is provided. The method may include adding a double-caged GABA compound, or a composition including at least one type of double-caged GABA compound to the biological sample. The double-caged GABA compounds may include a gamma-amino butyric acid covalently linked to a first photosensitive protecting group and a second photosensitive protecting group. The double-caged GABA compounds may be biologically inert before exposure to light. The first photosensitive protecting group and the second photosensitive protecting group may cleave from the gamma-amino butyric acid by photolysis upon exposure of the double-caged GABA compound to light. The method may include exposing the double-caged GABA compounds in the biological sample to light.

The biological sample may be but is not limited to cells, neurons, a tissue, and a slice of brain tissue. The biological sample may be the slice of brain tissue. The double-caged GABA compounds may be any one of double-caged GABA compounds described herein. The double-caged GABA compounds may be exposed to light. The light may be but is not limited to UV light, pulsed infrared light, or visible light. The light may be in a range from 250 nm to 500 nm wavelength. The light may be 250 nm to 300 nm, 300 nm to 350 nm, 350 nm to 400 nm, 400 nm to 450 nm, and 450 nm to 500 nm. The double-caged GABA compound may be exposed to light for a period from 0.001 ms to 1000 ms. The time period may be subdivided between any two values chosen from 0.001 increments within the described ranges (endpoints inclusive).

In an embodiment, the method may further include measuring the effect of chemical stimulation in a biological sample. The step of measuring may include measuring the effect of chemical stimulation by at least one parameter selected from the group consisting of: whole-cell ionic current, AMPA or GABA receptor density, correlation between AMPA or GABA receptor density and spine location, neuron connectivity, synaptic input, and neuronal output.

The step of measuring may include at least one procedure selected from the group consisting of: measuring an extinction coefficient, determining quantum yield, whole-cell patch clamp recording, imaging intracellular second messengers, and measuring intensity of illumination.

EMBODIMENTS

The following list includes particular embodiments of the present invention. The list, however, is not limiting and does not exclude alternate embodiments, as would be appreciated by one of ordinary skill in the art.

1. A double-caged GABA compound comprising a gamma-amino butyric acid covalently linked to a first photosensitive protecting group and a second photosensitive protecting group, wherein the double-caged GABA compound is biologically inert before exposure to light, and the first photosensitive protecting group and the second photosensitive protecting group cleave from the gamma-amino butyric acid by photolysis upon exposure of the double-caged GABA compound to light.

2. The double-caged GABA compound of embodiment 1, wherein the first photosensitive protecting group is linked to the carboxyl of the gamma-amino butyric acid.

3. The double-caged GABA compound of any one or more of the preceding embodiments, wherein the second photosensitive protecting group is linked to the amine of the gamma-amino butyric acid.

4. The double-caged GABA compound of any one or more of the preceding embodiments, wherein the first photosensitive protecting group is linked to the carboxyl of the gamma-amino butyric acid, and the second photosensitive protecting group is linked to the amine of the gamma-amino butyric acid.

5. The double-caged GABA compound of any one or more of the preceding embodiments, wherein the first photosensitive protecting group is selected from the group consisting of: nitrobenzyl, nitroindoline, carboxymethoxy-dinitroindoline, coumarin, and ruthenium, or any photosensitive derivative thereof.

6. The double-caged GABA compound of any one or more of the preceding embodiments, wherein the first photosensitive protecting group is selected from the group consisting of: nitrobenzyl (NB), nitrophenyl ethyl (NPE), α-carboxy-2-nitrobenzyl (CNB), 4,5-dimetoxy-2-nitrobenzyl (DMNB), 4,5-dimethoxy-2-nitrophenyl)ethyl (DM-NPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), and carboxynitrobenzyl.

7. The double-caged GABA compound of any one or more of the preceding embodiments, wherein the second photosensitive protecting group is selected from the group consisting of: nitrobenzyl, nitroindoline, carboxymethoxy-dinitroindoline, coumarin, and ruthenium, or any photosensitive derivative thereof.

8. The double-caged GABA compound of any one or more of the preceding embodiments, wherein the second photosensitive protecting group is selected from the group consisting of: nitrobenzyl (NB), nitrophenyl ethyl (NPE), α-carboxy-2-nitrobenzyl (CNB), 4,5-dimetoxy-2-nitrobenzyl (DMNB), 4,5-dimethoxy-2-nitrophenyl)ethyl (DM-NPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), and carboxynitrobenzyl.

9. The double-caged GABA compound of any one or more of the preceding embodiments, wherein the first photosensitive protecting group is selected from the group consisting of: nitrobenzyl, nitroindoline, carboxymethoxy-dinitroindoline, and coumarin, and a derivative thereof, and the second photosensitive protecting group is selected from the group consisting of: nitrobenzyl, coumarin and ruthenium, or any photosensitive derivative thereof.

10. The double-caged GABA compound of any one or more of the preceding embodiments, wherein the group selected as the first photosensitive protecting group is the same group as selected the second photosensitive protecting group.

11. The double-caged GABA compound of any one or more of the preceding embodiments, wherein the group selected as the first photosensitive protecting group is different than the group as selected the second photosensitive protecting group.

12. The double-caged GABA compound of any one or more of the preceding embodiments, wherein the first photosensitive protecting group or any byproduct thereof and the second photosensitive protecting group or any byproduct thereof is biologically inert after exposure to light and cleavage from the double-caged GABA compound.

13. The double-caged GABA compound of any one or more of the preceding embodiments, wherein at least one of the first photosensitive protecting group or the second photosensitive protecting group has an extinction coefficient greater than 1,000 $M^{-1}$ $cm^{-1}$.

14. The double-caged GABA compound of embodiment 13, wherein at least one of the first photosensitive protecting group or the second photosensitive protecting group has an extinction coefficient from 1,000 $M^{-1}$ $cm^{-1}$ to 60,000 $M^{-1}$ $cm^{-1}$.

15. The double-caged GABA compound of any one or more of the preceding embodiments, wherein at least one of the first photosensitive protecting group or the second photosensitive protecting group has a quantum yield from 0.005 to 1.0, wherein the quantum yield is the number of successful cleavages of the respective photosensitive protecting group from the gamma-amino butyric acid per photon absorbed.

16. The double-caged GABA compound of embodiment 15, wherein at least one of the first photosensitive protecting group or the second photosensitive protecting group has a quantum yield from 0.005 to 0.7.

17. The double-caged GABA compound of any one or more of the preceding embodiments, wherein at least one of the first photosensitive protecting group or the second caging group has an extinction coefficient greater than 1,000 $M^{-1}$ $cm^{-1}$; and at least one of the first photosensitive protecting group or the second photosensitive protecting group has a quantum yield from 0.005 to 1.0, wherein the quantum yield is the number of successful cleavages of the respective photosensitive protecting group from the gamma-amino butyric acid per photon absorbed; and a product of the extinction coefficient and the quantum yield for the first photosensitive protecting group exceeds 300 $M^{-1}$ $cm^{-1}$, and a product of the extinction coefficient and the quantum yield for the second photosensitive protecting group exceeds 300 $M^{-1}$ $cm^{-1}$.

18. The double-caged GABA compound of embodiment 17, wherein at least one of the first photosensitive protecting group or the second photosensitive protecting group has an extinction coefficient from 1,000 $M^{-1}$ $cm^{-1}$ to 60,000 $M^{-1}$ $cm^{-1}$ and at least one of the first photosensitive protecting group or the second photosensitive protecting group has a quantum yield from 0.005 to 0.7.

19. The double-caged GABA compound of any one or more of the preceding embodiments, wherein upon exposure to light, the gamma-amino butyric acid is released from the caged GABA compound at a rapid release rate of $10^4$ and $10^{13}$ gamma-amino butyric acid moieties released per millisecond.

20. The double-caged GABA compound of any one or more of the preceding embodiments having the structure of Formula I:

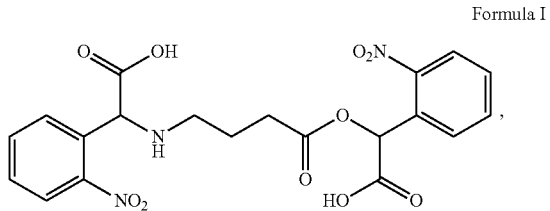 [SMILES: O=C(CCCNC(C(=O)O)c1ccccc1[N+](=O)[O-])OC(C(=O)O)c1ccccc1[N+](=O)[O-]]

Formula I or a derivative or a salt thereof.

21. The double-caged GABA compound of any one or more of the preceding embodiments, wherein the double-caged GABA compound is soluble in an aqueous solution.

22. The double-caged GABA compound of embodiment 21, wherein the aqueous solution is water or biological aqueous buffer.

23. The double-caged GABA compound of embodiment 22, wherein the biological aqueous buffer is one of HEPES or bicarbonate buffer.

24. The double-caged GABA compound of any one or more of the preceding embodiments, wherein light has a wavelength in a range from 250 nm to 500 nm.

25. A composition comprising one or more double-caged GABA compound of any one or more of the preceding embodiments.

26. The composition of embodiment 25 further comprising a biological aqueous buffer.

27. The composition of embodiment 26, wherein the biological aqueous buffer is one of HEPES or bicarbonate buffer.

28. The composition of embodiment 25 or 26 further comprising artificial cerebrospinal fluid.

29. A method of synthesizing a double-caged GABA compound comprising conjugating a first photosensitive protecting group and a second photosensitive protecting group to a gamma-amino butyric acid.

30. The method of embodiment 29, wherein the first photosensitive protecting group is conjugated to the carboxyl of the gamma-amino butyric acid.

31. The method of any one of embodiments 29 or 30, wherein the second photosensitive protecting group is conjugated to the amine of the gamma-amino butyric acid.

32. The method any one or more of embodiments 29-31, wherein the first photosensitive protecting group and the second photosensitive protecting groups are simultaneously conjugated to the gamma-amino butyric acid at the carboxy position and the amine position, respectively.

33. The method of any one or more of embodiments 29-32, wherein prior to conjugating the first photosensitive protecting group and the second photosensitive protecting groups are included in an intermediate compound.

34. The method of any one or more of embodiments 29-33, wherein conjugating includes combining the intermediate compound and the gamma-amino butyric acid in a solvent to form a mixture and providing an inert gas over the mixture.

35. The method of any one or more of embodiments 29-34 further comprising allowing the mixture to react for 1 hour to 25 hours.

36. The method of any one or more of embodiments 29-35 further comprising maintaining the mixture at a temperature of 20° C. to 65° C.

37. The method of any one or more of embodiments 29-36, wherein the intermediate compound is benzyl bromide.

38. The method of claim any one or more of embodiments 29-32, wherein the first photosensitive protecting group and the second photosensitive protecting group are conjugated to the gamma-amino butyric acid sequentially.

39. The method of embodiment 38, wherein the first photosensitive protecting group is conjugated to carboxyl of the gamma-amino butyric acid to form a mono-caged-gamma-aminobutyric acid.

40. The method of any one or more of embodiments 29-31 and 38-39, wherein the first photosensitive protecting group is conjugated to the amine of the mono-caged gamma-amino butyric acid.

41. The method of any one or more of embodiments 29-40, wherein the first photosensitive protecting group is selected from the group consisting of: nitrobenzyl, nitroindoline, carboxymethoxy-dinitroindoline, coumarin, and ruthenium, or any photosensitive derivative thereof.

42. The method of any one or more of embodiments 29-41, wherein the first photosensitive protecting group is selected from the group consisting of: nitrobenzyl (NB), nitrophenyl ethyl (NPE), α-carboxy-2-nitrobenzyl (CNB), 4,5-dimetoxy-2-nitrobenzyl (DMNB), 4,5-dimethoxy-2-nitrophenyl)ethyl (DMNPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), and carboxynitrobenzyl.

43. The method of any one or more of embodiments 29-42, wherein the second photosensitive protecting group is selected from the group consisting of: nitrobenzyl, nitroindoline, carboxymethoxy-dinitroindoline, coumarin, and ruthenium, or any photosensitive derivative thereof 44. The method of any one or more of embodiments 29-43, wherein the second photosensitive protecting group is selected from the group consisting of: nitrobenzyl (NB), nitrophenyl ethyl (NPE), α-carboxy-2-nitrobenzyl (CNB), 4,5-dimetoxy-2-nitrobenzyl (DMNB), 4,5-dimethoxy-2-nitrophenyl)ethyl (DMNPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), and carboxynitrobenzyl.

45. A method of chemical stimulation of a biological sample comprising:
adding at least one double-caged GABA compound selected from any one or more of embodiments 1-24, or a composition of any one or more of embodiments 25-28; and
exposing the double-caged GABA compound in the biological sample to light.

46. The method of embodiment 45, wherein the biological sample is selected from the group consisting of: cells, neurons, a tissue, and a slice of brain tissue.

47. The method of any one or more of embodiments 45 or 46, wherein the biological sample is the slice of brain tissue.

48. The method of any one or more of embodiments 45-47, wherein the double-caged GABA compound is exposed to light selected from the group consisting of: UV light, pulsed infrared light, and visible light.

49. The method of any one or more of embodiments 45-48, wherein the double-caged GABA compound is exposed to light in a range from 250 nm to 500 nm wavelength.

50. The method of any one or more of embodiments 45-49, wherein the double-caged GABA compound is exposed to light for a period from 0.001 ms to 1000 ms.

51. The method of any one or more of embodiments 45-50 further comprising measuring the effect of chemical stimulation in a biological sample.

52. The method of embodiment 51, wherein measuring the effect of chemical stimulation includes at least one parameter selected from the group consisting of: whole-cell ionic current, AMPA or GABA receptor density, correlation between AMPA or GABA receptor density and spine location, neuron connectivity, synaptic input and neuronal output.

53. The method of any one or more of embodiments 51 or 52, wherein measuring includes at least one procedure selected from the group consisting of: measuring an extinction coefficient, determining quantum yield, whole-cell patch clamp recording, imaging intracellular second messengers, and measuring intensity of illumination.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Double-caged GABA compounds may be synthesized by methods exemplified herein.

Example 1

Advantages of Double Caging Neurotransmitters

Although methods of probing neural activity such as microelectrode stimulation have become popular, "caged compounds" have emerged as an improved technique for achieving rapid, high-resolution neural stimulation. Caged compounds are neurotransmitters synthetically modified to contain a photoactive protecting group ("cage"), which undergoes autocleavage upon light exposure. Though caged versions of neurotransmitters such as glutamate have been successfully used in brain slices, previously developed forms of caged GABA have largely been shown to be antagonists for $GABA_A$ receptors, which has greatly limited their application. In order to minimize this antagonistic effect, double-caged GABA was synthesized, which is photoprotected at two functional groups. This bis-caged GABA exhibits significantly less antagonism for $GABA_A$ receptors and also uncages with rapid kinetics. In addition, the double caging results in a square relationship between light exposure and GABA release, conferring the added benefit of improved spatial resolution similar to that of two-photon excitation. Double-caged GABA is therefore a caged compound that significantly improves upon previous forms of caged GABA while also maintaining high spatial resolution.

This compound is a light-activated probe that can be used to achieve high spatial resolution stimulation of neurons with GABA. It can be used to study synaptic connectivity as well as function at the level of the individual neuron. Future applications could extend to focal stimulation in vivo for further probing or even therapeutic purposes.

Previously developed forms of caged GABA show significant antagonistic effects for GABA receptors, which has largely limited their usage (Molnár & Nadler, 2000, which is incorporated herein by reference as if fully set forth).

A "double-caging" strategy was adopted to address the problem of receptor antagonism. FIG. 1 (bottom) illustrates chemical two-photon uncaging of double-caged GABA. Incorporation of two cages at different positions on a neurotransmitter has been shown to offer several advantages Double caging GABA results in only minimal, residual antagonism for $GABA_A$ receptors (a significantly diminished effect compared to other caged GABAs) and no effect on glutamate receptors. In addition, this compound exhibits rapid uncaging despite being caged at the amine (which usually results in slow release of substrate through a carbamate intermediate). bis-CNB-GABA therefore avoids two major side effects plaguing many existing forms of caged GABA.

Any residual antagonism exhibited by double-caged GABA could be considered a limitation, though it does not practically limit the use of double-caged GABA as a probing tool in vitro. The observed antagonism is considerably reduced compared to other caged GABAs, which have seen limited application because of this undesirable antagonism. If it were necessary to completely eliminate any residual antagonism, GABA could be photoprotected with a cage (or combination of cages) that prevents it from binding to GABA receptors. The synthesis and evaluation of a doubly-caged GABA analog, bis-CNB-GABA, is described herein. This compound is a powerful tool for high-resolution control of brain circuits.

The compound was tested in vitro. It was tested for GABA and glutamate receptor antagonism, kinetics of uncaging, as well as photolysis-evoked GABA currents. The results showed no antagonistic effects on glutamate receptors, only very residual antagonism for GABA receptors, and rapid uncaging to generate GABA currents.

Other applications of the compound may include giving greater spatial resolution of receptor activation, owing to the nonlinear light dependence. See for example, Pettit, D. L., Wang, S. S-H., Gee, K. R., & Augustine, G. J. (1997). Chemical two-photon uncaging: a novel approach to mapping glutamate receptors. *Neuron,* 19, 465-471, which is incorporated herein by reference as i fully set forth. See also Canepari, M., Nelson, L., Papgeorgiou, G., Corrie, J. E. T., & Ogden, D. (2001). Photochemical and pharmacological evaluation of 7-nitroindolinyl- and 4-methoxy-7-nitrodindolinyl-amino acids as novel, fast caged neurotransmitters. *Journal of Neuroscience Methods,* 112, 29-42; Molnár, P., & Nadler, J. V. (2000). Gamma-aminobutryate, alpha-2-nitrobenzyl ester selectively blocks inhibitory synaptic transmission in rat dentate gyrus. *European Journal of Pharmacology,* 391, 255-262; Matsuzaki, M., Hayama, T., Kasai, H., & Ellis-Davies, G. C. R. (2010). Two-photon uncaging of gamma-aminobutyric acid in intact brain tissue. *Nature Chemical Biology,* 6, 255-257, all of which are incorporated herein by reference as if fully set forth.

The compound may also be useful for high throughput screening of GABA receptors. GABA receptors may include any GABA receptor including but not limited to GABA_A, GABA_B and GABA_C.

Double caging of GABA has at least two advantages: only residual antagonism of receptors, and non-linear spatial resolution of GABA release. In addition to bis-CNB-GABA, other bis-caged-GABA compounds can be made by an analogous synthetic pathway.

Example 2

Method of Sequential Synthesis of the Double-Caged GABA

Briefly, the amine group on GABA is Boc-protected. A cage group (for example, dimethoxynitrobenzyl, DMNB; or bromohydroxycoumarin, Bhc) is added to the carboxy position of GABA by a pathway that does not disrupt the methoxy side chains of the Boc group. After deprotection of the Boc group, a second caged group is added at the amine, yielding a final product of bis-caged-GABA. The same procedure could be followed for other cage groups.

Example 3

Caged Compounds and Non-Linear Release of Substrate

It should be noted that a cage does not physically encapsulate the substrate. Rather, it is simply a chemical addition to the compound that renders it biologically inert. For neuroscientists, the caged substrate of interest is often a neurotransmitter, such as glutamate. FIG. 1 (top) illustrates a conventional uncaging scheme for GABA. Referring to this figure, upon light exposure, the light-sensitive cage will undergo photolysis, releasing the now-biologically active substrate. In practice, a brain slice is submerged in a solution of the biologically inert caged neurotransmitter, and a laser light source is focused on the desired area of stimulation. This results in photolytic cleavage of the cage and rapid release of the neurotransmitter, which can subsequently go on to activate the neural receptors in its immediate surroundings. The net result is therefore controlled, light-mediated stimulation of neurons (Dore, T. M., & Wilson, H. C. (2011). Chromophores for the delivery of bioactive molecules with two-photon excitation. In J. J. Chambers & R. H. Kramer (Eds.), Photosensitive molecules for controlling biological function (57-90). New York, N.Y.: Springer, which is incorporated herein by reference as if fully set forth).

Figure 2:
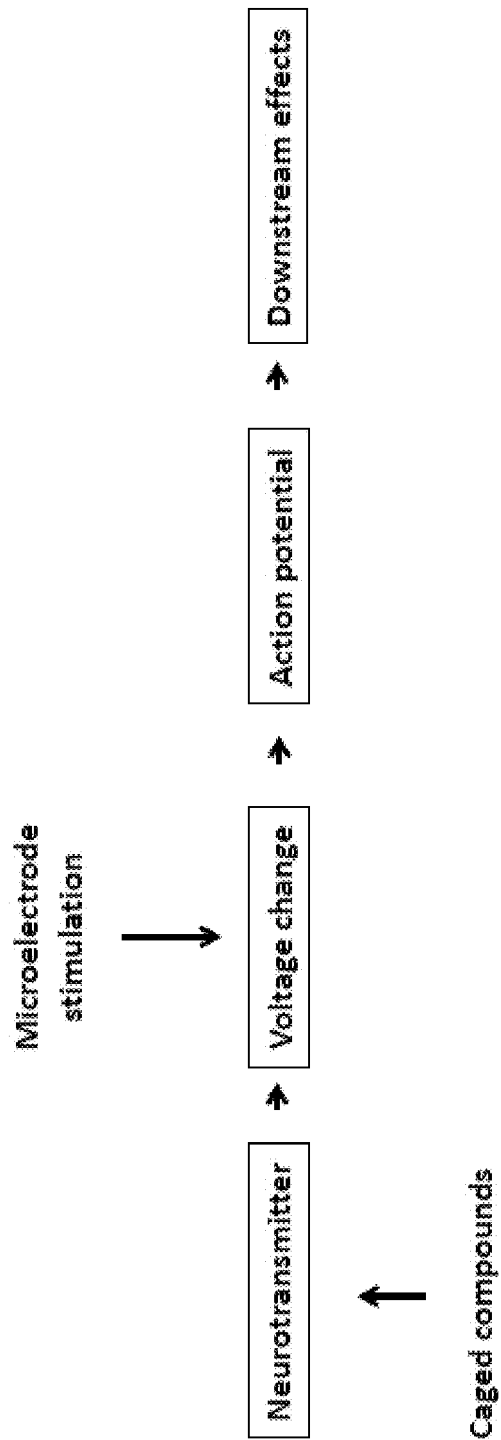
FIG. 2 illustrates a sequence of events for a neuron transmitting its signal.

It should be emphasized that caged compounds stimulate neurons through chemical means at the level of the neurotransmitter, whereas microelectrode stimulation functions through electrical means at the level of the cell's voltage. In order for a neuron to fire, it must first be stimulated by a neurotransmitter. If this voltage reaches a threshold level, the neuron will fire an action potential and propagate its signal. Microelectrodes function by manually injecting current into the cell and ramping the intracellular voltage above threshold level. Contrarily, caged compounds function by introducing neurotransmitter to the neuron's receptors upon light exposure. Microelectrode stimulation therefore only allows for manipulation of cellular voltage and does not allow for chemical control, meaning that neural function in response to different neurotransmitters and receptor activation is unattainable. FIG. 2 illustrates sequence of events of a neuron transmitting its signal. Referring to this figure, microelectrodes control this pathway at the level of the voltage. Still referring to FIG. 2, caged compounds instead operate one level upstream at the neurotransmitter, allowing for chemical modulation of neural activity. Still referring to FIG. 2, by acting one level upstream from the cell's voltage, caged compounds can be used for chemical modulation of the neuron, representing an added dimension of control not possible with microelectrodes.

There are several additional advantages of caged neurotransmitters over electrophysiological methods. First, stimulation through uncaging achieves a much higher level of spatial resolution. When using microelectrodes, resolution is limited by the diameter of the microelectrode. Caged neurotransmitters are limited not by the physical size of a pipette, but instead by the diameter of a laser, which has a much finer focal point than a microelectrode.

Second, stimulation via caged compounds is much easier to execute compared to electrophysiological stimulation. Whereas patching requires the experimenter to make direct contact and form a seal with the specific neuron of interest, caged compounds only require accurate aim of a laser. The technique is therefore not plagued by a high failure rate that often accompanies even the most experienced neuroscientists. In addition, it allows the experimenter to stimulate numerous areas simultaneously, a task that would be nearly impossible for microelectrodes.

Furthermore, caged compounds have significant advantages over other types of optical stimulation such as optogenetics and small molecule photoswitches. Most importantly, caged compounds do not require any genetic alterations to the region of interest. This is practically advantageous compared to optogenetics specifically, given that the conductance of a single ChR2 channel is several orders of magnitude smaller than that of the endogenously expressed voltage-gated channels. A high density of ChR2 channels must therefore be expressed, which requires strong promoters for ChR2 gene expression (Kramer et al., 2009 Current Opinion in Neurobiology, 19, 1-9, which is incorporated herein by reference as if fully set forth). In addition the genetically non-invasive nature of caged compounds allows them to have potential future applications in humans. Whereas application of caged compounds is potentially executable in humans, similar applications of optogenetics and small molecule photoswitches would require expression of the light-activated channel or receptor interest in the human, which is unlikely.

Caged neurotransmitters therefore represent a significant development in neuroscience methodology. Their high-resolution stimulation as well as ease of execution makes them highly useful probing tools. In addition, many substrates of interest to neuroscientists (such as glutamate, GABA, and dopamine) are synthetically accessible as caged compounds, allowing for multiple types of chemical control depending on the neurotransmitter of interest.

Example 4

Non-Linear Release of Substrates

Thus far, the description of caged compound suggests a direct relationship between the area of light exposure and area of released substrate. That is, neurotransmitter release occurs in the localized area that is exposed to light. Though uncaging in this way has had wide application, significant extensions of this framework have since been developed (Walker et al., 1986 Biochemistry, 25, 1799-1805; Milburn et al., 1989 Biochemistry, 28, 49-55, which are incorporated by reference as if fully set forth).

Example 5

Two-Photon Excitation

Figure 3:
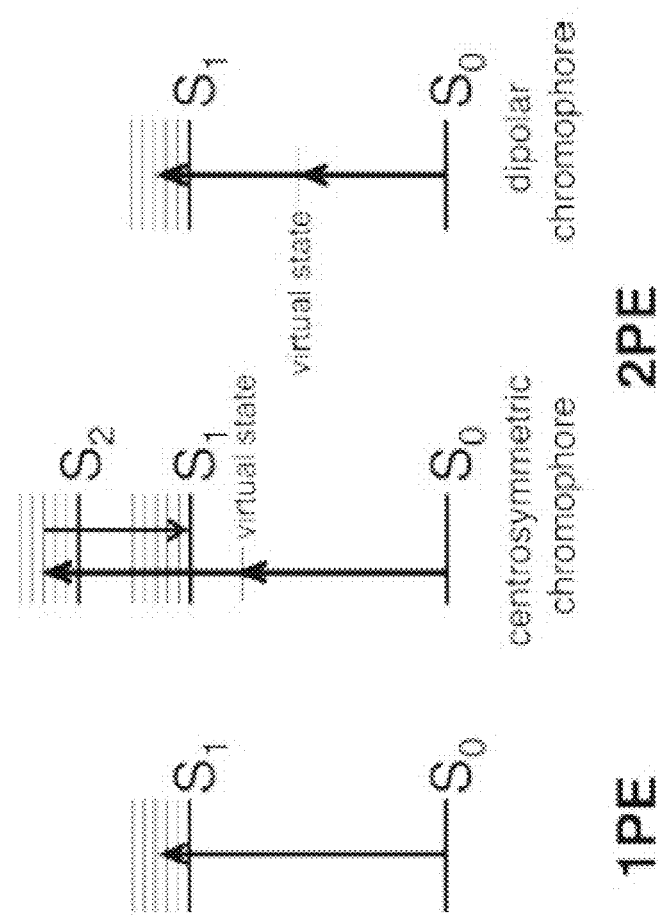
FIG. 3 illustrates allowed electronic states for one-photon excitation (1PE) and two-photon excitation (2PE) of a chromophore.

FIG. 3 illustrates allowed electronic states for one-photon excitation (1PE) and two-photon excitation (2PE) of a chromophore as described by Dore, T. M., & Wilson, H. C. 2011. Referring to FIG. 3 (left), in a traditional, single-photon model of excitation, an electron reaches its excited state after absorbing a quanta of light (left). That is, each individual photon of light that the caged compound is exposed to has enough energy to initiate photocleavage of the cage and release of the substrate. The result is a linear relationship between substrate release and light exposure. Referring to FIG. 3 (right), this single-photon absorption model was complicated by suggestion that an electron could become excited by simultaneous absorption of two photons of light, each at approximately half the energy necessary to reach the excited state. In the context of caged compounds, two-photon excitation (2PE) implies a necessary near-simultaneous absorption of two photons in order to initiate photolysis. Two-photon excitation has significant advantages over its single-photon counterpart. Perhaps most important, 2PE confers even greater spatial resolution than previously possible. Because two photon absorptions are necessary to initiate photolysis, there is a square—as opposed to linear—relationship between light exposure and substrate release. One can imagine that if single-photon uncaging generates a 60% release of substrate at a specific location, that same location would only generate 36% release of substrate if using 2PE.

Figure 4:
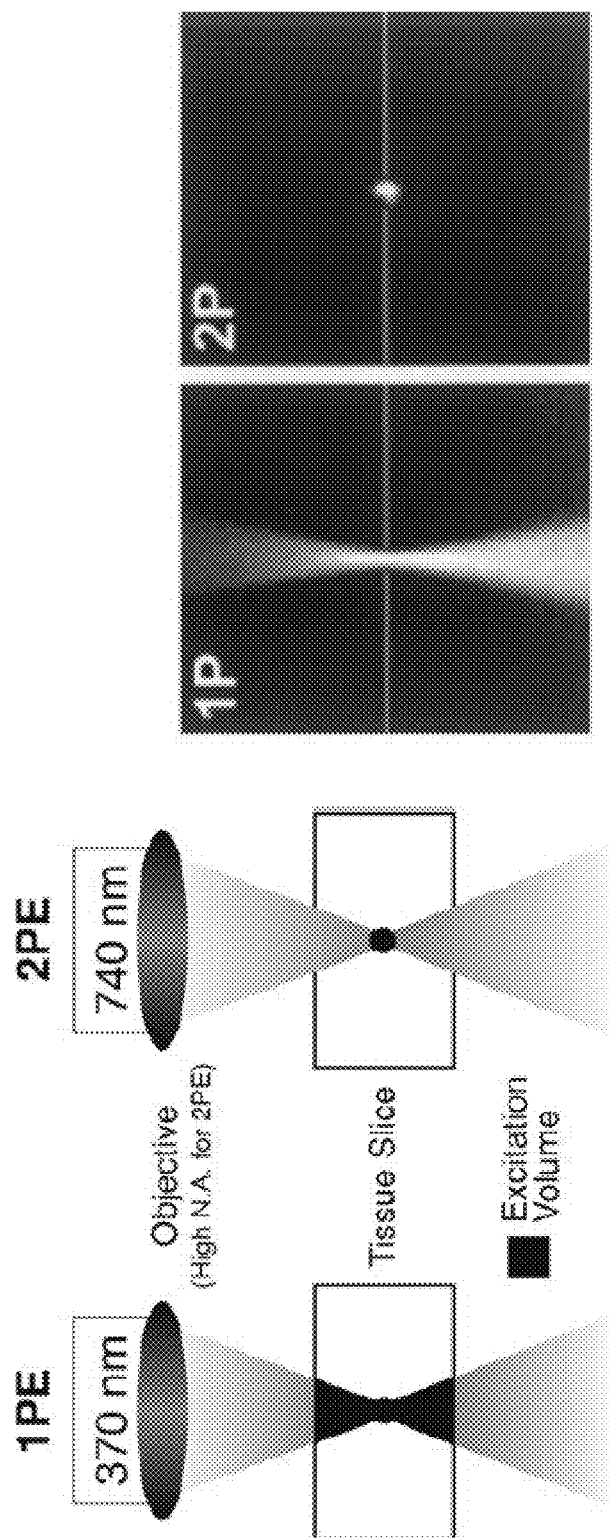
FIG. 4 illustrates theoretical (left) and experimental (right) release of substrate with one-photon and two-photon excitation.

FIG. 4 illustrates theoretical (left) and experimental (right) release of substrate with one-photon and two-photon excitation as per Dore, T. M., & Wilson, H. C., 2011, and Rubart, 2004). The laser has the highest intensity of light at the smallest area of light exposure, the focal point. Intensity decreases as distance from the focal point increases (Dore, T. M., & Wilson, H. C. (2011). Referring to FIG. 4, the net result is more localized uncaging at the area of highest light intensity, with less unwanted uncaging in the surrounding areas. In addition, 2PE requires lower wavelength light, resulting in less photodamage to neural tissue and less scattering of light, meaning that localized substrate release can occur at much deeper areas within tissue. However, it should be noted that though the light source is lower energy, high intensity light is necessary. Exceeding a laser power of roughly 10 mW can result in biological damage at the focal point of the laser (Kiskin et al., 2002 European Biophysics Journal, 30(8), 588-604, which is incorporated by reference as if fully set forth). In addition, the necessary high-intensity light source (typically a pulsed laser) can be somewhat sophisticated and beyond what is available in a typical neuroscience lab. Nevertheless, 2PE confers many advantages for efficient optical probing of neurophysiology and has been a popular variation of traditional single-photon uncaging (Matsuzaki et al., 2001 Nature Neuroscience, 4, 1086-1092; Fino et al., 2009 Frontiers in Neural Circuits, 3, 1-9; Ellis-Davies et al., 2007 The Journal of Neuroscience, 27(25), 6601-6604, all of which are incorporated by reference as if fully set forth).

Example 6

Applications of 2PE

Certain one of the following examples represent only a selection of the expansive literature making use of two-photon sensitive caged compounds. A double-caged compound herein could include one of the cage groups in these examples.

Example 7

Spatial Resolution and Dendritic Spine Geometry

One particular field that has benefited from two-photon uncaging has been dendritic structure and function. This is in part due to the fact that studying presynaptic effects at the level of the dendrite necessitates high spatial and therefore can benefit from caged compounds. A notable application utilized the specificity of caged compounds to map AMPA receptors at the level of individual dendritic spines (Matsuzaki et al., 2001 Nature Neuroscience, 4, 1086-1092, which is incorporated herein by reference as if fully set forth). The authors used two-photon uncaged glutamate photoprotected with 4-methoxy-7-nitroindolinyl (MNI) to determine the density of AMPA receptors at mushroom spines, thin spines, and filopodia of hippocampal CA1 pyramidal neurons. FIG. 19 illustrated MNI structure. This was done by photolyzing caged glutamate and recording the two-photon evoked EPSCs. FIGS. 5A-5H illustrate functional mapping of glutamate sensitivities in hippocampal neurons by Matsuzaki et al., 2001. FIG. 5A illustrates fluorescence image of a neuron in culture. Referring to FIG. 5A, the gray box indicates a region of interest for functional mapping. FIG. 5B illustrates pseudocolor coding of the amplitude of a 2pEPSC. FIG. 5C illustrates region of interest of the neuron shown in FIG. 5A for functional mapping. FIG. 5D illustrates a pseudocolor map of peak amplitudes of 2pEPSCs (glutamate sensitivity map). FIG. 5E illustrates a smoothed glutamate sensitivity map by linear interpolation. FIG. 5F illustrates overlay of FIG. 5C and FIG. E. FIG. 5G illustrates a FM143 fluorescence image. FIG. 5H illustrates an overlay of FIG. 5E and FIG. 5G. Referring to FIGS. 5A-5E, uncaging allowed to observe a positive correlation between AMPA receptor density and spine size, suggesting a clear structure-function relationship. In addition, no correlation was observed between AMPA receptor density and spine location, suggesting that the two function independently. That is, the activity of one spine does not have an effect on directly neighboring spines, implying that each spine independently regulates receptor activity.

These conclusions were made possible through simulation of presynaptic stimulation, accomplished by the use of caged glutamate. The rapid kinetics of the MNI-glutamate photolysis responses mimicked the time scale of presynaptic input to the spines, which allowed the authors to simulate presynaptic input without presynaptic stimulation. In addition, uncaging allowed efficiently stimulate at many different spines—a task that would be significantly more time-intensive if using microstimulation. Most importantly, these results highlight the impressive spatial resolution of uncaging, which allowed the authors to map this AMPA receptor density at the level of each individual spine. Specifically, the spatial resolution of the AMPA receptor mapping was 0.6 µm laterally and 1.4 µm axially, representing a high level of spatial control. These results by Matsuzaki et al. exemplify the spatial specificity of caged compounds and represent a direct application in which caged compounds are utilized to reach conclusions that would otherwise be unattainable with traditional modes of microstimulation.

Example 8

Laser Scanning Photostimulation

Given the ability to efficiently stimulate several areas of interest very rapidly, uncaging has been used to map large networks of connectivity with laser scanning photostimulation (LSPS). This method is essentially large scale uncaging across numerous areas of interest. In practice, a light source is used to uncage at several discrete locations in sequence on a brain slice bathed in caged compound. This allows the experimenter to stimulate thousands of presynaptic neurons very efficiently, making LSPS especially useful for mapping connectivity (Katz, Dalva, 1994 Journal of Neuroscience Methods, 54, 205-218). Specifically, experimenters could stimulate a large number of presynaptic neurons and record from a single neuron of interest. Any observed postsynaptic spiking from the neuron of interest following photolysis implies connectivity between the two, allowing experimenters to scan many neurons very rapidly in order to determine connectivity.

Figure 6:
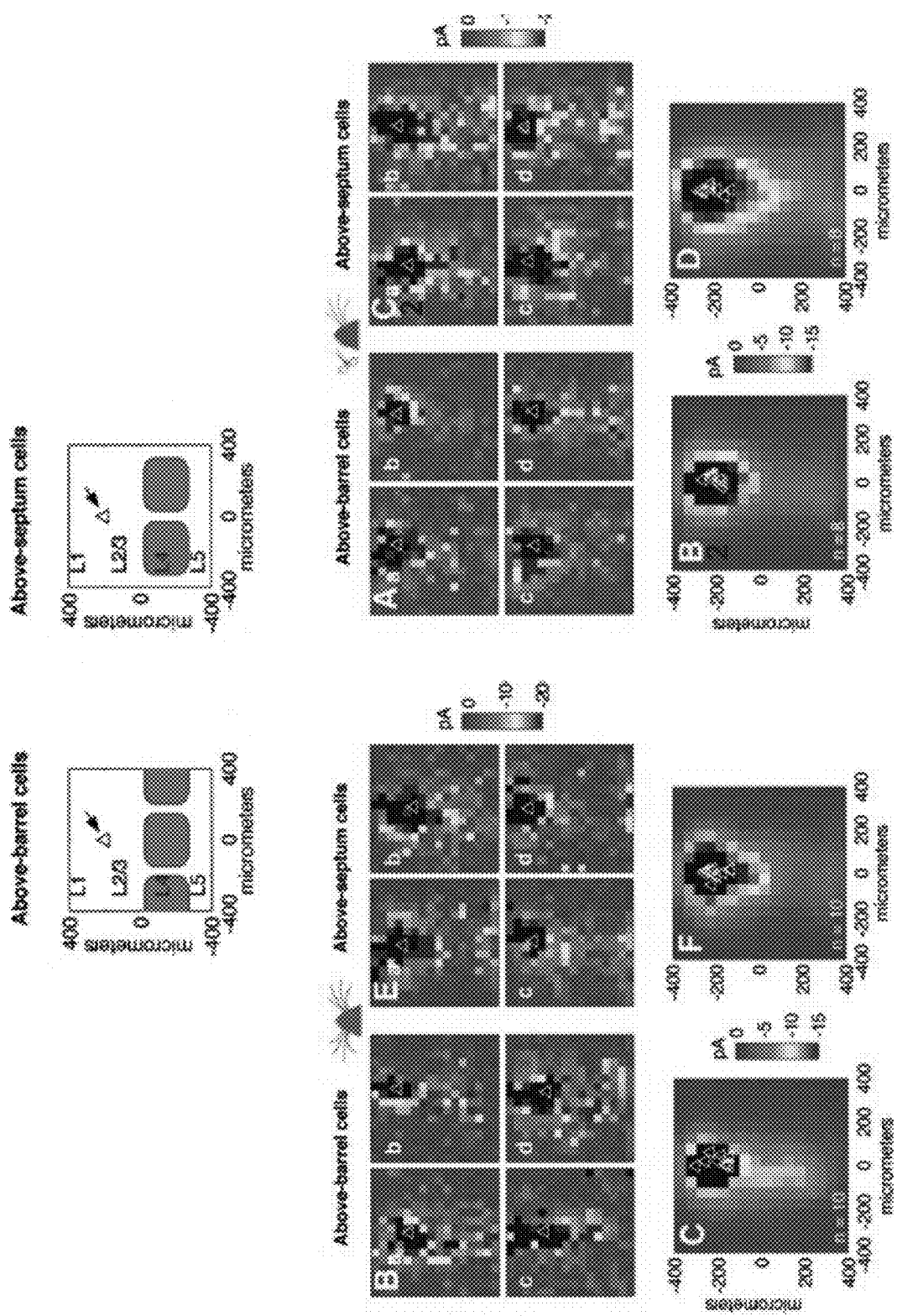
FIG. 6 illustrates cortical layer connectivity before and after whisker deprivation.

The use of LSPS has been reported by Shepherd et al. Nitroindolinyl-caged glutamate was used to determine the connectivity of neurons in the rat barrel cortex before and after whisker sensory deprivation. The LSPS was used with caged glutamate and then recorded cortical layers that had a subsequent excitatory response. An observed photolysis-induced response signifies that the two neurons are synaptically linked, or that they are connected via an interneuron. Specifically, differential connectivity was examined at two regions of the rat cortex: barrels and septa by Shepherd, G. et al., 2003 Neuron, 38, 277-289, which is incorporated by reference herein as if fully set forth. The connectivity first was mapped before whisker deprivation and found that layer 2/3 cortical neurons above barrels receive more synaptic input from layer 4 cortical neurons than those above septa. However, whisker deprivation reversed this pattern and showed greater layer 4 input to layers 2/3 in above-septum cells versus above barrel cells. FIG. 6 illustrates cortical layer connectivity before and after whisker deprivation as per Shepherd et al., 2003. Referring to FIG. 6, glutamate was uncaged at in layer 4 cortex and response was recorded at layers 2/3 (top). Still referring to FIG. 6, quadrants in B and A show individual neurons (a-d) directly above barrels. C and B2 show averages of these responses. Still referring to FIG. 6, quadrants E and C2 depict individual neurons (a-d) directly above septa. Still referring to FIGS. 6, F and D show averages of these responses. Still referring to FIG. 6, above-barrel cells show more connectivity between layers 2/3 and layer 4 in the control condition, compared to above-septum cells (comparison of C and F). However, this is reversed in the whisker-deprived conditions (compare B2 and D) (Shepherd et al., 2003). This provides compelling evidence for a competitive interaction between barrel and septa cells for layer 4 input. Importantly, this evidence was made possible by the efficient scanning of connectivity between these layer 4 and layer 2/3 cortical neurons with caged glutamate. If the same results were attempted with microelectrodes, each neuron would have to be patched individually and stimulated, a very tedious and time-intensive task.

Example 9

Sequential Stimulation at Fixed Rates

Uncaging gives neuroscientists the ability to stimulate areas of interest with specific temporal control as well. The experimenters examined voltage summation at the soma as a result of sequential stimulation in the inward and outward directions of a cortical pyramidal dendrite.

Figure 7A:
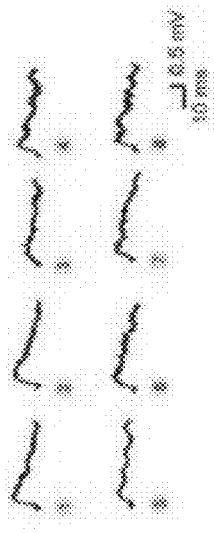
FIGS. 7A-7H illustrate that single dendrites are sensitive to the direction and velocity of synaptic input patterns.
Figure 7B:
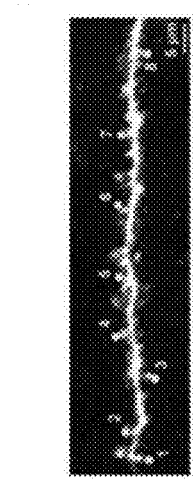
Figure 7C:
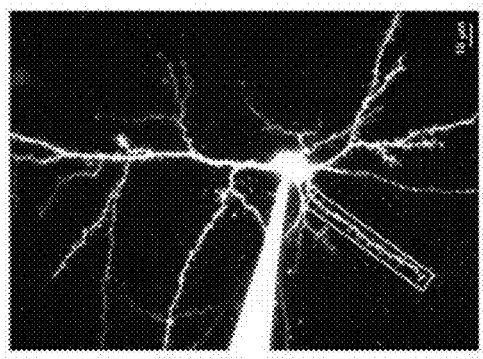
Figure 7D:
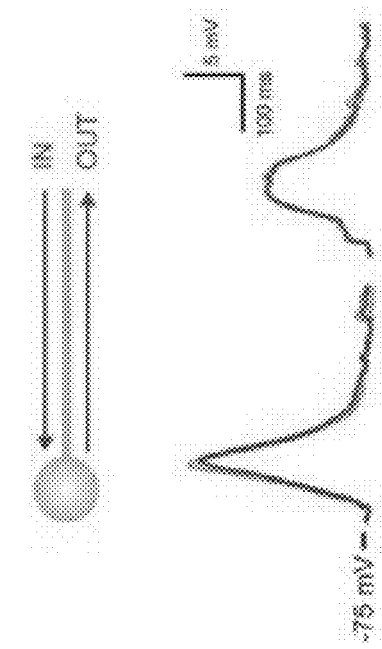
Figure 7E:
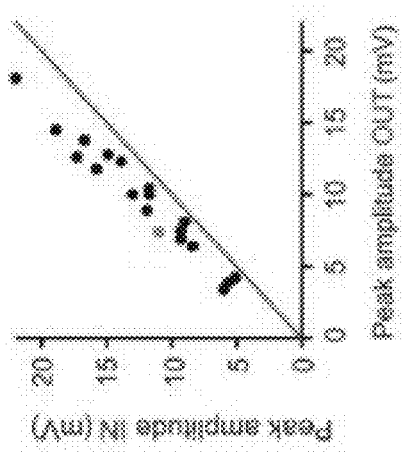
Figure 7F:
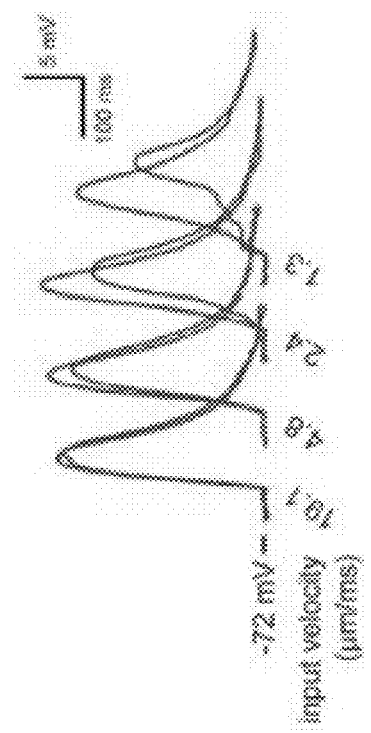
Figure 7G:
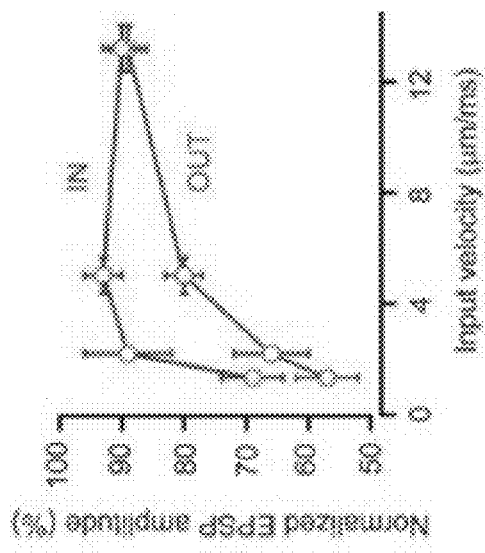
Figure 7H:
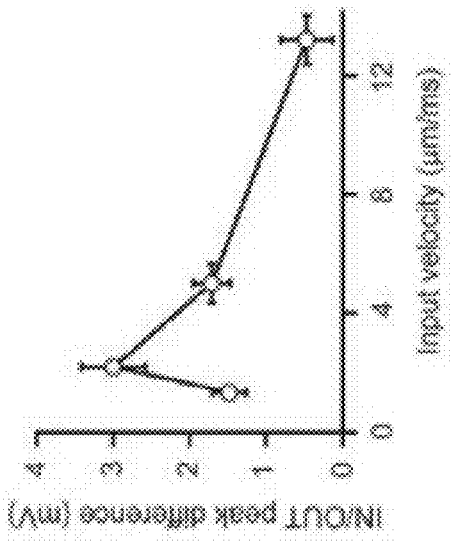

FIGS. 7A-7H illustrate that single dendrites are sensitive to the direction and velocity of synaptic input patterns as reported by Branco et al., 2010. FIG. 7A illustrates layer 2/3 pyramidal cell filled with Alexa 594 dye; white box indicates the selected dendrite. FIG. 7B illustrates uncaging spots (white) along the selected dendrite. FIG. 7C illustrates average individual uncaging responses at the soma. FIG. 7D illustrates somatic responses to IN and OUT directions at 2.3 mm/ms (averages denoted by bold lines). FIG. 7E illustrates plot comparing peak amplitudes for IN and OUT sequences at the optimal velocity for direction selectivity [light gray circle, example shown in FIG. 5D]. FIG. 7F illustrates direction-selective responses at different velocities. FIG. 7H illustrates relation between peak voltage and input velocity (values normalized to the maximum response in the IN direction for each cell, n=15). Error bars indicate SEM. (H) Relation between direction selectivity and input velocity (n=15) (Branco et al., 2010 Science, 329, 1671-1675, which is incorporated herein as if fully set forth). Referring to FIGS. 7A, 7B and 7D), MNI-glutamate was uncaged locally along the dendrite, either in the inward direction (towards the soma) or outward direction (away from the soma). Referring to FIGS. 7C-7E, a linear summation of voltage was observed when stimulating outwards, but a supralinear voltage summation when stimulating inwards. It was hypothesized that dendrites can encode not only synaptic input, but also the temporal sequence of this input. The ability for dendrites to discriminate in temporal sequence introduces the possibility of information coding not only through firing rates, but through temporal sequence as well.

These results depended on the ability to stimulate several portions of the dendrite at a consistent speed. Referring to FIGS. 7F-7H, Branco et al. photolyzed the caged glutamate at several different input velocities. Because dendritic stimulation via uncaging only requires focusing the light source at the area of interest, the experimenters were able to achieve this temporally controlled stimulation. If this same pattern of stimulation at highly specific velocities were attempted with microelectrodes, each section of the dendrite would have to be separately patched, making sequential stimulation at any consistent speed an impossible task. These results therefore highlight a clear temporal advantage conferred by caged compounds.

Example 10

Chemical Two-Photon Excitation

The application of 2PE was extended. A neurotechnique referred to as chemical two-photon uncaging (C2PE) was introduced by Pettit D. et al, 1997 Neuron, 19, 465-471, which is incorporated by reference as if fully set forth.

Figure 8E:
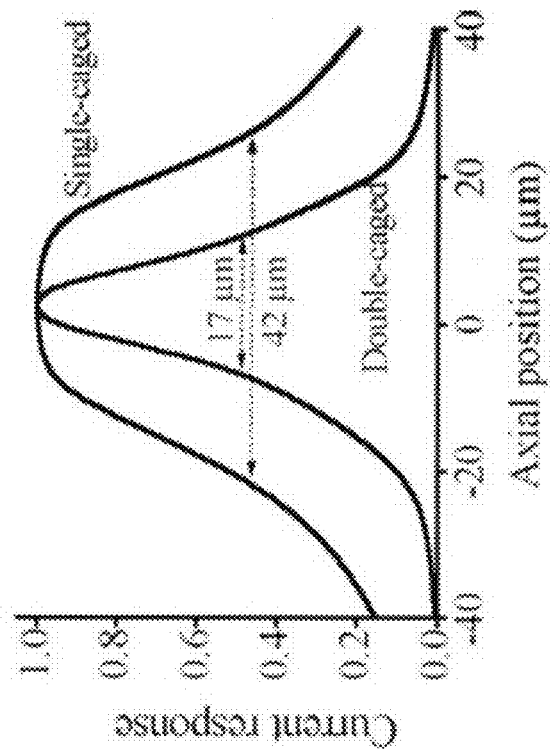
Figure 8D:
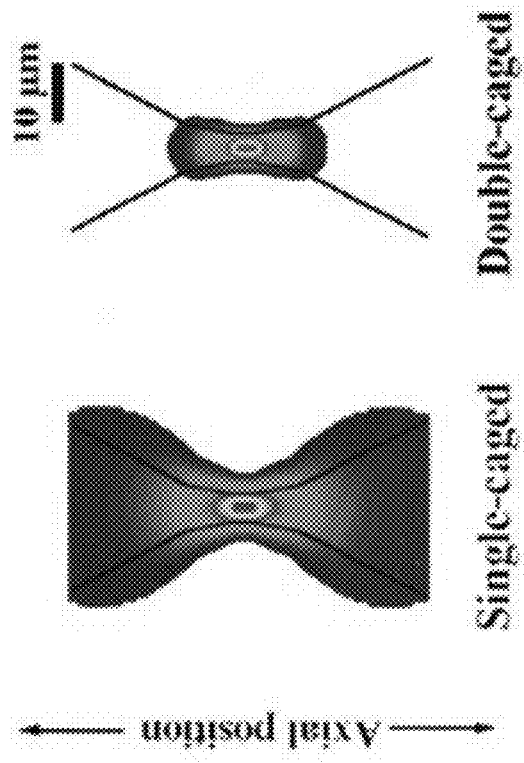

FIGS. 8A-8E illustrate theoretical improvements in spatial resolution of chemical two-photon uncaging. FIG. 8A illustrates a scheme of chemical two-photon uncaging using GABA as the neurotransmitter substrate. FIG. 8B illustrates structure of bis-CNB-glutamate. FIG. 8C illustrates focal shape and light intensity of laser. FIG. 8D illustrates expected release of glutamate in single-caged and double-caged glutamate. FIG. 8E illustrates predicted improvements in axial resolution in single-caged and double-caged glutamate. Referring to FIG. 8A, unlike 2PE uncaging, C2PE uses two cage groups on a single neurotransmitter substrate. Upon light exposure, both cages then undergo photocleavage, liberating the neurotransmitter and both cages' byproducts. Because C2PE requires two successful photocleavages in order for neurotransmitter to be released, this technique confers a similar square relationship between light exposure and neurotransmitter release as 2PE. The term "chemical two-photon uncaging" therefore refers to mimicking the spatial resolution of 2PE through chemical means, as opposed to optical means.

It should also be emphasized that in C2PE, each cage is not required to be two-photon sensitive. As a result, though the advantages of using lower energy light are absent, a sophisticated high-intensity laser is not required, making C2PE uncaging a practical probing technique for laboratories without specialized equipment. This is especially useful considering that lasers necessary for two-photon excitation can cost ~$100,000, whereas C2PE can be achieved with an argon laser at approximately a fifth of this cost (Denk et al., 1990 Science, 248, 73-76; Pettit et al., 1997 Neuron, 19, 465-471, which are incorporated by reference herein as if fully set forth).

These benefits make C2PE an important development in caged compound research. The synthetic routes used to make these compounds can often be more complicated, but their usefulness as efficient, light-activated probes with high spatial resolution makes them worth pursuing. The current project therefore focuses on synthesizing various forms of double-caged compounds, both with different substrates and different cages.

Example 11

Applications of C2PE

Chemical two-photon uncaging has been successfully applied to glutamate and $IP_3$ to generate the predicted square relationship of spatial resolution, thus illustrating its usefulness as a probing tool.

Double-Caged Glutamate

Referring to FIGS. 9A-9C, the improved spatial resolution conferred by double-caging was quantified by Pettit D. et al. (1997) Neuron, 19, 465-471, which is incorporated herein as if fully set forth. FIGS. 9A-9C illustrate experimental improvements in spatial resolution of chemical two-photon uncaging. FIG. 9A illustrates current traces evoked by single- and double-caged glutamate (5 ms flashes at 10 s intervals), obtained while varying the distance between the neuronal cell body and the focal plane of the UV light beam. FIG. 9B illustrates relationship between light energy and peak amplitude of currents evoked in individual pyramidal neurons by single-caged (closed circles) or double-caged (open circles) glutamate. Referring to FIG. 9B, Linear regression fits to the log-log plotted data (solid lines) give slopes of 1.09 for single-caged and 1.97 for double-caged glutamate. FIG. 9C illustrates relationship between axial position and the peak currents shown in top left. Referring to FIG. 9C, the half-widths of the Gaussian functions fit to single and double-caged glutamate responses are 40 mm and 15 mm, respectively. Referring to FIG. 8A, the glutamate was photolyzed and caged at both carboxylates with the α-carboxy-2-nitrobenzyl (CNB) cage group. Referring to FIGS. 8B-8D and FIG. 9C, bis-CNB-glutamate showed the predicted square relationship (FIGS. 8B-8D) between light exposure and glutamate release, first evidenced by the non-linear relationship between light energy and peak amplitude of current response (FIG. 9C). In addition, compared to the single caged compound with a half-maximal current response of 40 μm away from the focal point, bis-CNB-glu exhibited a 15 μm half-maximal response (FIG. 9A). Finally, a smaller current response to double-caged glutamate was observed compared to single-caged glutamate when photolyzed at the same concentrations. They found comparable response amplitudes only when using significantly different concentrations of each (25 μM single-caged glutamate and 100 μM double-caged glutamate). This suggests that there is a lowered probability of producing glutamate when it is double-caged, providing further confirmation that the absorption of two photons is required for complete photolysis of double-caged glutamate.

Finally, it is important to note the successful application of bis-CNB-glutamate at a range of concentrations. A possible concern of bis-protecting a substrate is the subsequent loss in aqueous solubility due to the hydrophobicity of the cage group. However, bis-CNB-glutamate remained sufficiently soluble at the concentrations necessary for in vitro stimulation, suggesting that any decrease in solubility was not enough to interfere with its application.

These results provide strong evidence for the predicted advantages of chemical two-photon uncaging. There is a direct comparison between resolution of single-caged and double-caged substrates, and the results highlight the clear improvements conferred by the addition of a second cage.

Double-Caged $IP_3$

Figure 10:
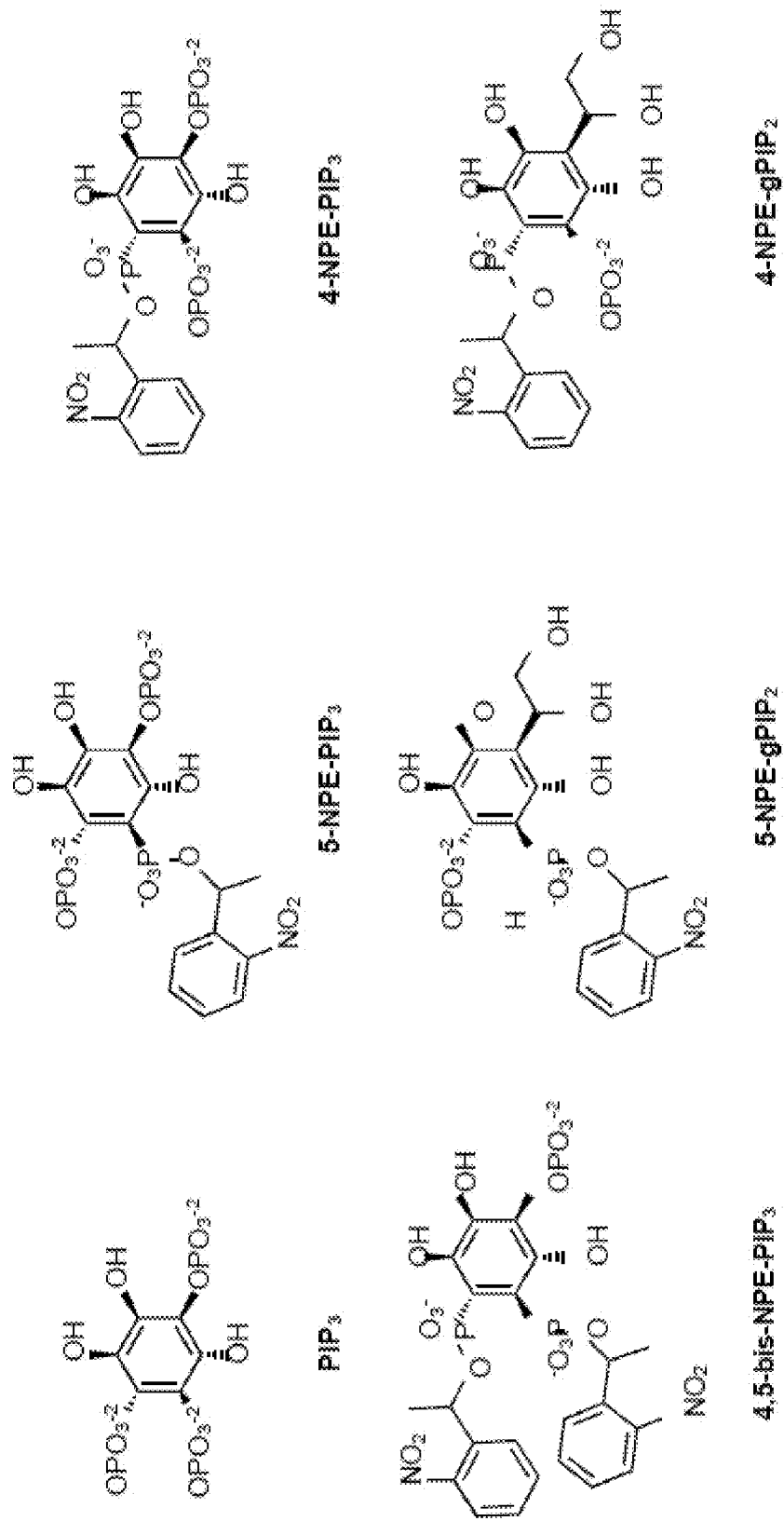
FIG. 10 illustrates structure of $PIP_3$, single-caged $PIP_3$, double-caged $PIP_2$, and single-caged gPIP.
Figure 11A:
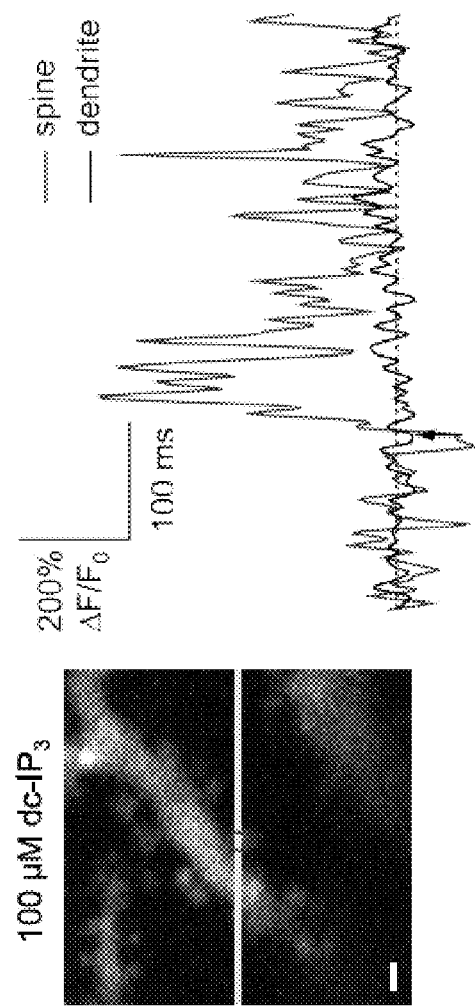
FIGS. 11A-11D illustrate calcium uncaging responses in dendritic spines.
Figure 11B:
Figure 11C:
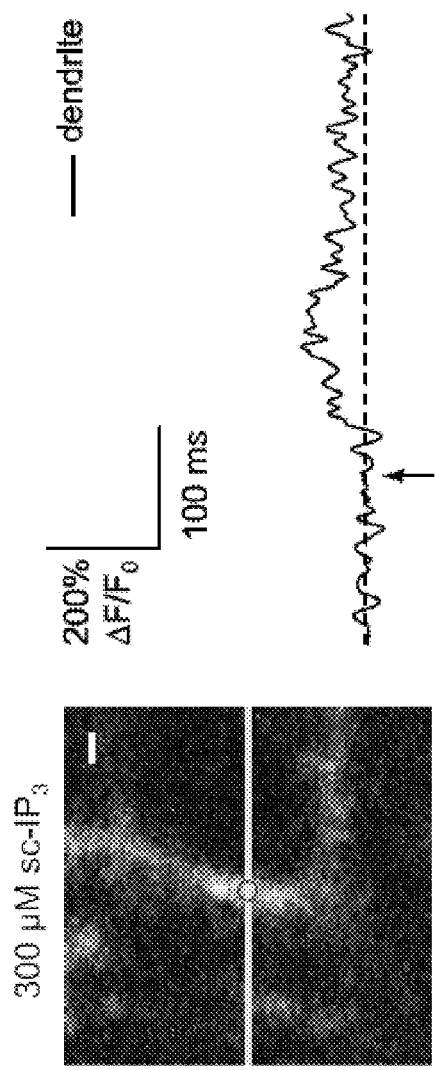
Figure 11D:
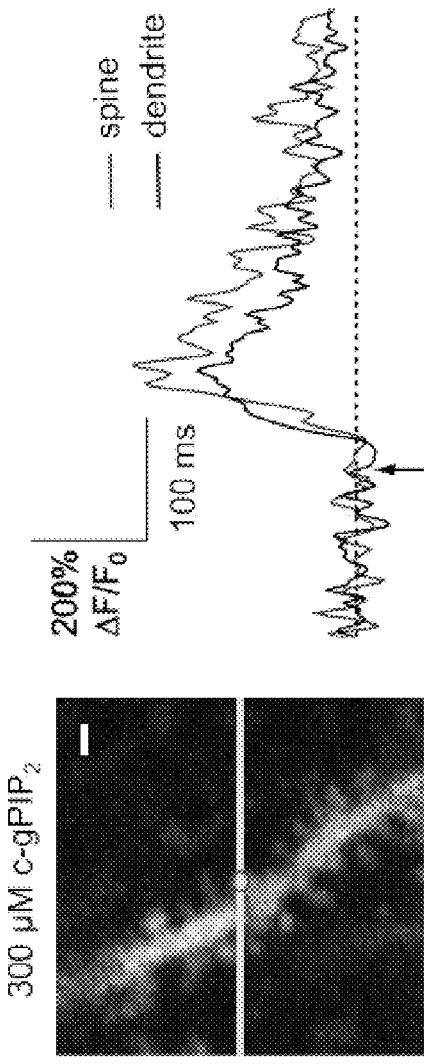

Chemical two-photon uncaging has been used not only with neurotransmitters, but with other biologically relevant compounds as well. One notable example is inositol 1,4,5-triphosphate ($IP_3$), a second messenger that triggers calcium release in neurons. Though single-caged forms of $IP_3$ have been successfully used, the evidence was provided for concentration dependent antagonist activity of single-caged $IP_3$ (caged with 1-(2-nitrophenyl)ethyl, NPE) (Finch and Augustine, 1998 Nature, 396, 753-756; Khodakhah and Armstrong, 1997 Proclamations from the National Academy of Sciences, 94, 14009-14014; Inoue et al., 1998 Journal of Neuroscience, 18, 5366-5373, all of which are incorporated by reference as if fully set forth). A notable difference was observed in the calcium response to photolysis of single and double-caged $IP_3$, quantified by fluorescent calcium imaging. FIG. 10 illustrates structure of $PIP_3$, single-caged $PIP_3$, double-caged $PIP_2$, and single-caged gPIP. Specifically, though uncaging of bis-NPE-$IP_3$ at 100 μM at the dendrites was effective in generating a calcium response (84% success rate), the same concentration of mono-NPE-$IP_3$ was much less successful (42%). FIGS. 11A-11D illustrate calcium uncaging responses in dendritic spines as reported by Sarkisov et al., 2009. FIG. 11A illustrates typical responses to uncaging in spiny dendrites of 100 mM double-caged (dc) $IP_3$. FIG. 11B illustrates 100 mM single-caged (sc) $IP_3$. FIG. 11C illustrates 300 mM single-caged $IP_3$. FIG. 11D illustrates 100 mM caged gPIP. In the images the circles indicate uncaging locations, and the lines indicate the orientation of the line scan. Referring to FIG. 11C, scale bars are 1 mm.

Referring to FIGS. 11A-11D, in addition, photolysis of mono-NPE-$IP_3$ showed a complete lack of calcium response in the spiny branchlets (0%) even when the concentration was increased. In contrast, bis-NPE-$IP_3$ was effective at generating a calcium response even at lower concentrations (100 μM, 83%). The authors hypothesize that this diminished calcium response from mono-NPE-$IP_3$ is due to antagonist activity of the single-caged compound itself. Single-caged $IP_3$—but not double-caged $IP_3$-contains two unmodified phosphate groups that can bind to the $IP_3$ receptors and act as an antagonist.

Referring to FIGS. 10 and 11A-11D, the authors provide further support for their claim by observing no antagonist effect in calcium release when photolyzing caged $gPIP_2$, a caged compound with only one exposed phosphate, similar to bis-NPE-$IP_3$.

These results highlight another distinct advantage of chemical two-photon uncaging. Double-caged $IP_3$ resulted in robust calcium release without exhibiting the antagonist effects observed with single-caged $IP_3$. This suggests a clear advantage of using multiple cage groups to ensure biological inertness. Additionally, bis-NPE-$IP_3$ exhibited tight spatial resolution of photolysis-induced calcium release, with an average half-maximal width of fluorescence of 0.59 μm following photolysis. Chemical two-photon uncaging therefore has been a highly useful tool for probing neurophysiology, and in these examples is a significant improvement over previously developed single-caged compounds.

Example 12

Useful Properties for Cage Groups

Whether a substrate undergoes two-photon excitation or chemical two-photon excitation, there are several necessary considerations when choosing a cage. Caged compounds and the cages themselves could satisfy several characteristics in order to be useful for neuroscientists. The quality and applicability of a caged compound may depend on a combination and optimization of numerous factors.

Temporal Efficiency.

Figure 12:
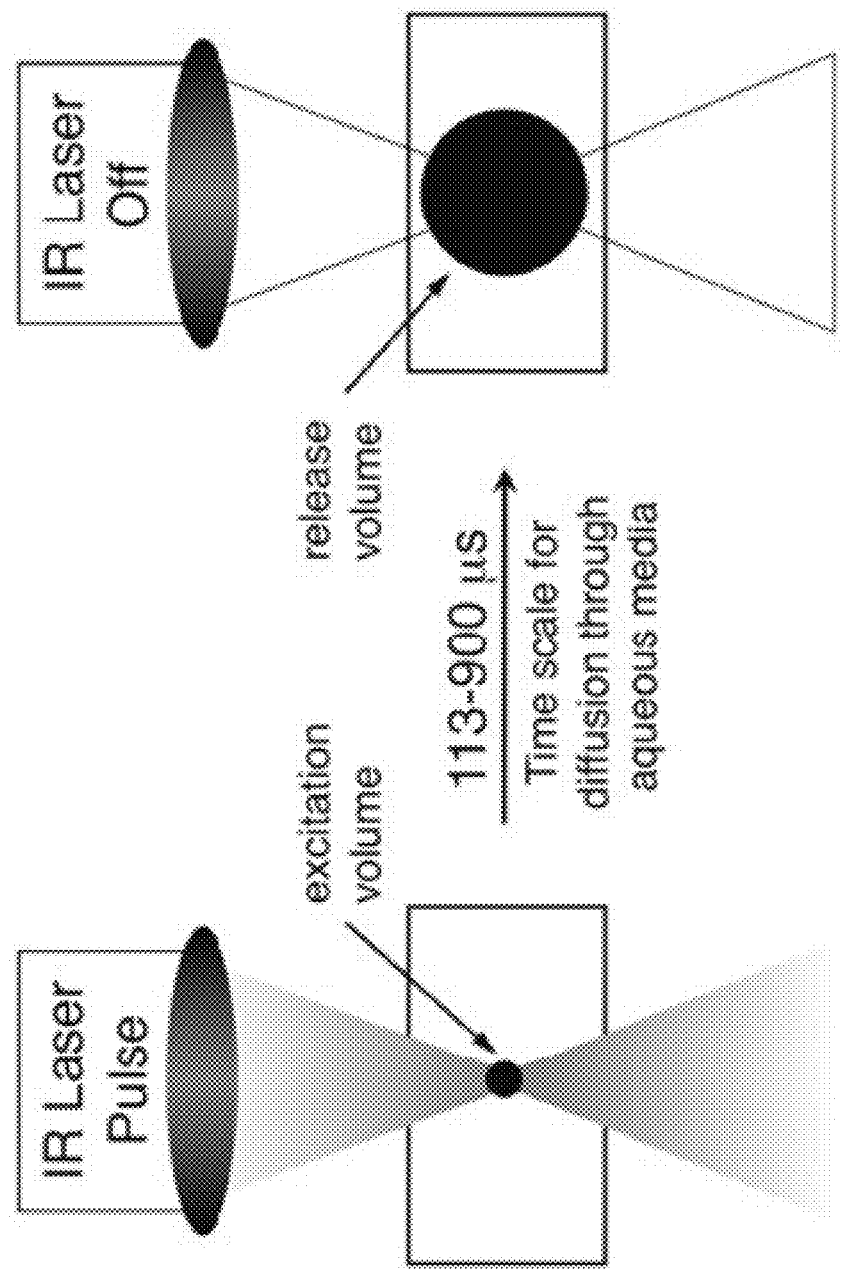
FIG. 12 illustrates effects of diffusion on spatial resolution of uncaging.

A preferred cage neutronsmitter would undergo rapid photolytic cleavage upon exposure to light. Typically, this range is between $10^4$ and $10^6$ substrates released per second (Ellis-Davies, 2007 *Nature Methods*, 4(8), 619-628, which is incorporated herein by reference as if fully set forth). The high spatial resolution unique to caged compounds is dependent on photolysis only at the area targeted by the laser. If the neural tissue is bathed in solution of caged compound, and light exposure results in a slow photolysis, the uncaged neurotransmitter can diffuse to surrounding areas of the tissue and cause a larger area of stimulation than originally intended. FIG. 12 illustrates effects of diffusion on spatial resolution of uncaging per Dore & Wilson, 2011. Referring to FIG. 12, slow uncaging results in larger volume of substrate release relative to area of light exposure (Dore & Wilson, 2011, which is incorporated herein by reference as if fully set forth). Still referring to FIG. 12, this means that any spatial resolution gained by uncaging is lost if photolysis is slow. Uncaging must therefore ideally occur fast enough so that diffusion does not significantly affect the area of substrate release.

Slow release of substrate can be due to several factors. In some cases, the photolysis mechanism occurs through a two-step process, with one step being rate-limiting. In other cases, the mechanistic steps that must occur are simply too slow to maintain localized release of substrate. Nonetheless, rapid photocleavage is critical for achieving the high spatial resolution that caged compounds are designed to achieve.

Synthetic Accessibility.

In order for a substrate to be caged, it should have a viable synthetic route. Elaborate schemes are sometimes necessary (Canepari et al., 2001 *Journal of Neuroscience Methods*, 112, 29-42; Ellis-Davies, 2007, *Nature Methods*, 4(8), 619-628; Zhu et al., 2006 *Journal of American Chemical Society*, 128, 4267-4276, all of which are incorporated by reference as if fully set forth). Synthetic accessibility may shape the design of cages. Carboxylates are perhaps the most versatile functional group, meaning that they are compatible with a large portion of the previously developed cages, making carboxylates a popular choice for caging.

FIGS. 13A-13B illustrate caged amines. FIG. 13A illustrates a scheme of caging via a carbamate linker (left) and structure of nitrobenzyl-caged amine with a carba-mate. FIG. 13B illustrates a scheme of direct caging on amine (left) and structure of nitrobenzylcaged amine via direct caging. Referring to FIGS. 13A-13B, amines can be caged either by directly attaching a cage group, or by using a carbamate linker. FIG. 14 illustrates photolysis of carbamate-caged amines. Referring to FIG. 14, the cage first photocleaves, followed by decarboxylation to release the substrate. Still referring to FIG. 14, the primary drawback is that uncaging occurs via a carbamate salt, which then must spontaneously decarboxylate in order to release the free amine substrate. Though this intermediate itself is not toxic or detrimental, decarboxylation is relatively slow (~7 ms), resulting in less temporal efficiency and diffusion of the caged compound before the substrate is released (Corrie, 2005 Photoremovable protecting groups used for the caging of biomolecules. In M. Goeldner & R. S. Givens (Eds.), *Dynamic studies in biology: phototriggers, photoswitches and caged biomolecules* (1-94). Wiley-VCH Verlag GmbH & Co., which is incorporated herein by reference as if fully set forth). As a result, spatial resolution suffers.

Solubility.

Preferred caged neurotransmitters would have high solubility in the solution used to bathe the brain slice, such as artificial cerebrospinal fluid (ACSF) or other aqueous solutions. Solubility in the μM range can be enough to achieve effective uncaging if using single-photon excitation. However, two-photon excitation requires higher concentrations typically in the mM range. Examples of functional groups that help increase solubility include the carboxylate groups on both nitrobenzyl derivatives as well as CDNI. FIG. 19 illustrates cage groups derived from nitroindoline. Structure of CDNI is illustrated on FIG. 19.

Inert Before Photolysis

Preferred caged compounds would only release substrate upon light exposure.

A strategy for designing a cage would be to use a large, bulky chromophore as the basis for a cage. The bulkier the cage, the more likely that it will render the compound biologically inert.

Figure 15:
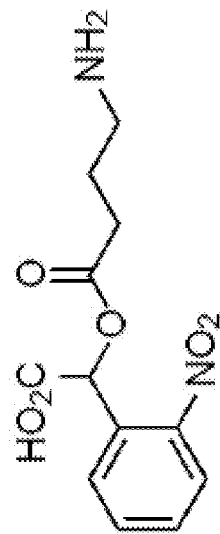
FIG. 15 illustrates structure of CNB-GABA.

FIG. 15 illustrates structure of CNB-GABA. Referring to FIG. 15, CNB-GABA is in theory a highly useful probing tool because GABA is the primary inhibitory neurotransmitter and the nitrobenzyl cages have efficient photorelease properties (Purves et al., 2008 *Neuroscience* (4th ed.). Sunderland, Mass.: Sinauer Associates, Inc.; Weiboldt et al., 1994 *Proceedings of the National Academy of Sciences*. 91, 8752-8756, both of which are incorporated herein by reference as if fully set forth). However, CNB-GABA has been found to antagonize GABA receptors before photolysis, which has largely limited the use of caged GABA as a probing tool Inert Photolysis Byproducts.

Photolysis may result in not only release of the desired substrate, but also the cage groups themselves. Preferred caged compounds would release byproducts that would not contribute to any unwanted side activity.

High Extinction Coefficient.

Because light activation initiates photolysis, preferred cage groups would absorb light efficiently. Extinction coefficient (c) quantifies how well a compound absorbs light at a specific wavelength and is derived from the Beer-Lambert Law:

$$A = c\epsilon l$$

where A represents absorbance, c is the concentration of the caged compounds, and l is the distance the light travels through the solution of compound. Extinction coefficient is therefore expressed in $M^{-1}$ $cm^{-1}$. An accepted minimum standard for extinction coefficient is roughly 1,000 $M^{-1}$ $cm^{-1}$. However, some of the most highly absorbing cages have extinction coefficients above 60,000 $M^{-1}$ $cm^{-1}$, while the most commonly used cages absorb in roughly the 2,000 $M^{-1}$ $cm^{-1}$ to 7,000 $M^{-1}$ $cm^{-1}$ range (Dore & Wilson, 2011, In J. J. Chambers & R. H. Kramer (Eds.), *Photosensitive*

*molecules for controlling biological function* (57-90). New York, N.Y.: Springer, which is incorporated herein by reference as if fully set forth).

The wavelength of maximal absorption ($\lambda_{max}$) could also be considered. Light with wavelengths shorter than the UV range may cause photodamage to neural tissue.

The lower limit of light absorption could be 250 nm in order to be useful, though cages could have $\lambda_{max}$ values upwards of 350 nm. Because extinction coefficient is reflective of the ability of the cage itself (as opposed to the substrate) to absorb light, its value does not vary significantly based on the substrate being caged. Cages could incorporate substituted aryl rings, which are effective chromophores.

High Quantum Yield.

Quantum yield ($\phi$) characterizes the ability for a caged compound to release its substrate upon successful absorption of a photon. It is equal to the proportion of molecules that undergo successful photolysis to release the substrate after photon absorption. Quantum yield is therefore unitless and theoretically ranges from 0 to 1, with 1 representing perfect efficiency of photolysis upon light absorption. Quantum yields of cages could range from as low as 0.005 (DMNB) to 0.7 (NDBF), or 0.05 to 0.3 range.

FIG. 16 illustrates quantum yields of release of p-hydroxyphenacyl (pHP) cages, highlighting the range of quantum yields depending on the substrate caged as measured by Pelliccioli et al., 2002. Referring to FIG. 16, Fdis refers to quantum yield as measured by disappearance of starting material. Referring to FIG. 16, Fapp refers to quantum yield as measured by appearance of substrate (Pelliccioli et al., 2002, *Photochemical & Photobiological Sciences*, 1, 441-458, which is incorporated herein by reference as if fully set forth). Quantum yield varies depending on compound. Ideally, the product of extinction coefficient and quantum yield should exceed 300 $M^{-1}$ $cm^{-1}$. It would be useful to balance extinction coefficient and quantum yield—both are useful for caged compounds, and optionally one should not be entirely sacrificed for the other.

Several factors are necessary to consider when designing and choosing a cage. Each factor contributes uniquely to the success of a cage and its subsequent applicability. Cage design could balance and optimize across numerous characteristics.

Example 13

Selection of Cages

Nitrobenzyl Cages.

The nitrobenzyl cages are versatile in that they could be used to cage a range of functional groups, including alcohols, phosphates, carboxylates, and amines. In addition, nitrobenzyl-caged compounds are adequately soluble for physiological use, even when double-caged with glutamate (Pettit et al., 1997). These cage groups additionally undergo rapid cleavage in the microsecond timescale when caging a carboxylate (Wieboldt, Gee, et al., 1994), making them suitable for a range of physiological usage.

Figure 18:
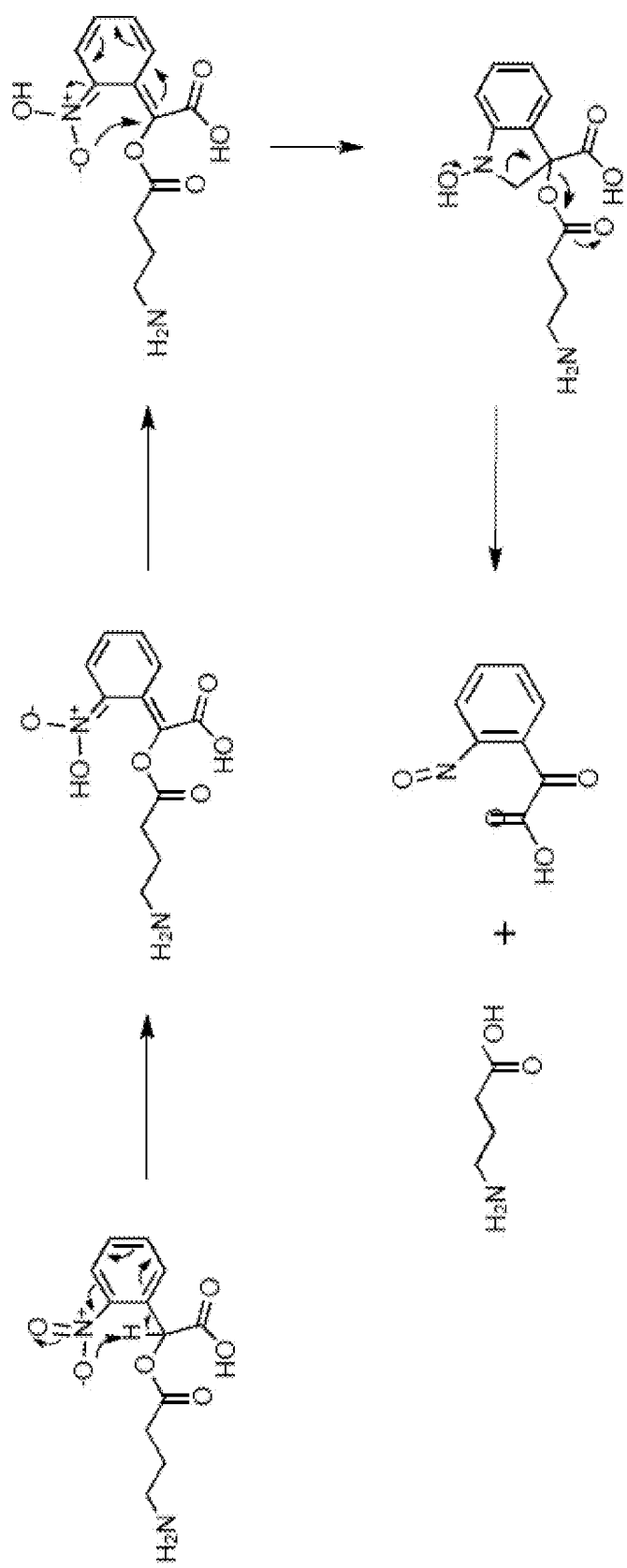
FIG. 18 illustrates an uncaging mechanism of the nitrobenzyl cages, illustrated with CNB-GABA.

FIG. 17 illustrates cages based on 2-nitrobenzyl. Referring to FIG. 17, the nitrobenzyl group has been derivatized to generate several different types of nitrobenzyl cages. FIG. 18 illustrates uncaging mechanism of the nitrobenzyl cages, illustrated with CNB-GABA. Referring to FIG. 18, the uncaging mechanism proceeds through a cyclized intermediate and is heavily dependent on solvent and pH. Aside from the parent 2-nitrobenzyl cage (NB), other popular cages such as 4,5-dimethoxy-2-nitrobenzyl (DMNB) and 1-(2-nitrophenyl)ethyl (NPE) have been developed. However, they are largely limited by either inefficient release of substrate as evidenced by low quantum yield or slow photolysis. DMNB in particular exhibits strong absorption at a relatively lower wavelength ($\epsilon$=6,100 $M^{-1}$ $cm^{-1}$ at 346 nm), but shows somewhat inefficient release of substrate when used to cage glutamate ($\phi$=0.006, $\phi\times\epsilon$=37 $M^{-1}$ $cm^{-1}$) (Furuta et al., 1999 *The Journal of Organic Chemistry*, 60(13), 3953-3956, which is incorporated herein by reference as if fully set forth). NPE also shows a 9 $s^{-1}$ rate constant of glutamate release at pH 7, making it impractical to probe neural activity on a physiologically relevant timescale (Wieboldt, Gee, et al., 1994 *Proceedings of the National Academy of Sciences*. 91, 8752-8756, which is incorporated herein by reference as if fully set forth). However, the α-carboxy-2-nitrobenzyl (CNB) cage largely circumvents these obstacles faced by other nitrobenzyl cages. CNB ($\epsilon$5,100 $M^{-1}$ $cm^{-1}$ at 262 nm).

Figure 26:
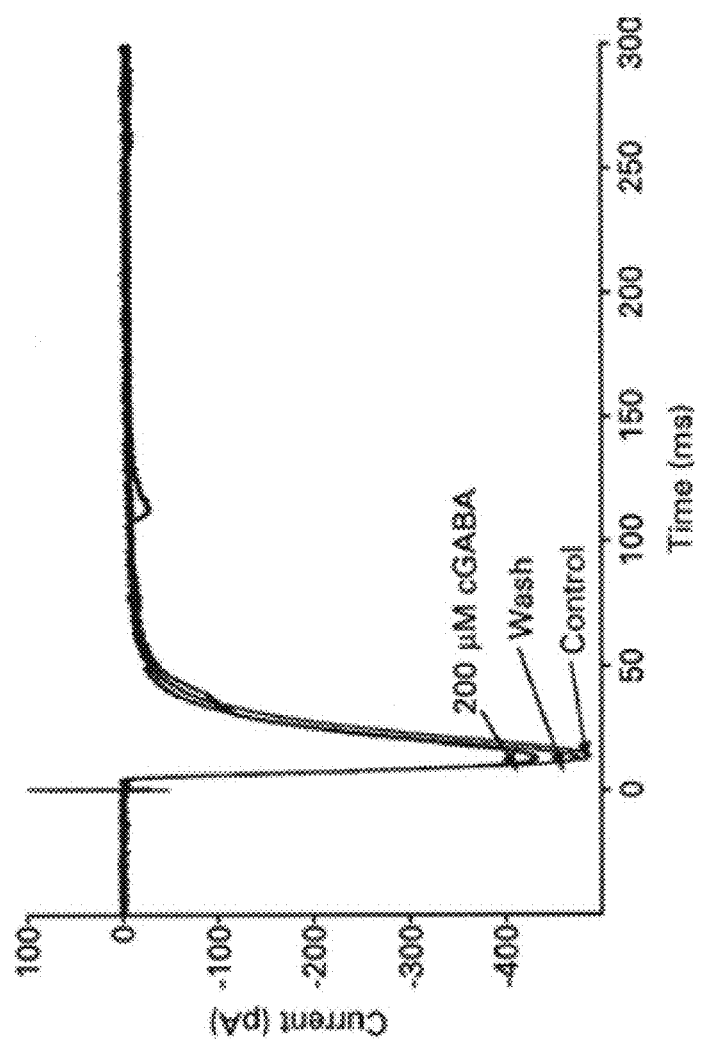
FIG. 26 illustrates whole-cell patch clamp recordings from dentate granule cells of rat hippocampal slices.

FIG. 26 illustrates whole-cell patch clamp recordings from dentate granule cells of rat hippocampal slices by Molnár & Nadler, 2000. Referring to FIG. 26, CNB-GABA itself is an antagonist of $GABA_A$ receptors, which has limited its further application.

It is important to note that while these nitrobenzyl cage groups have gained popularity for a variety of substrates, they are insensitive to two-photon excitation. As a result, non-linear spatial resolution that is achieved with two-photon excitation cannot be attained with a single CNB cage group. The primary advantage of CNB is its versatility caging a range of functional groups, as well as its aqueous stability and lack of toxic byproducts. Because it is one of the first-developed cages, its properties are well-known and reliable, making CNB a popular choice as a cage group.

Nitroindoline Cages.

As two-photon excitation emerged as a potentially valuable tool to achieve high-resolution photostimulation, it became necessary to design cages that could take advantage of this development. Cage groups derived from nitroindoline became highly useful because they exhibit this two-photon sensitivity. FIG. 19 illustrates cage groups derived from nitroindoline. Referring to FIG. 19, the first popularized nitroindoline cage was 4-methoxy-7-nitroindoline (MNI).

FIG. 20 illustrates mechanism of photolysis of nitroindoline cages, illustrated with CDNI-glutamate. Referring to FIG. 22, the nitroindoline cage releases its substrate through a five-membered ring intermediate. MNI has been used to cage glutamate, GABA, and glycine. MNI-glutamate releases its substrate rapidly with a quantum yield of $\phi$=0.085 and has been used successfully to map glutamate receptors (Matsuzaki et al., 2001 *Nature Neuroscience*, 4, 1086-1092, which is incorporated herein by reference as if fully set forth). However, like all two-photon sensitive cages, MNI-caged compounds must be used in high concentrations (in the millimolar range) in order to achieve a useful magnitude of response amplitude. Nevertheless, MNI-glutamate has become a standard choice for two-photon excitation, and MNI-glutamate is now made commercially available. However, MNI-GABA exhibits antagonistic effect on $GABA_A$ receptors, though less than CNB-GABA (Palma-Cerda et al., 2012 *Neuropharmacology*, 63, 624-634, which is incorporated herein by reference as if fully set forth).

Attempts to improve the quantum yield of MNI resulted in the subsequent development of a second prominent nitroindoline derivative, 4-carboxymethoxy-5,7-dinitroindolinyl (CDNI) by Ellis-Davies et al. CDNI significantly improves quantum yield ($\phi$=0.5 when caged on carboxylate of glutamate) and also undergoes successful two-photon uncaging (Ellis-Davies et al., 2007 *Nature Methods*, 4(8), 619-628, which is incorporated herein by reference as if fully set forth).

Nitroindoline cages have become known for their two-photon sensitivity, rapid kinetics, and aqueous solubility. However, nitroindolines can only be used to cage carboxylate functional groups, which limits their application. While groups such as CNB have been used to cage ATP peptides, and even $Ca^{2+}$, CDNI and MNI have much less versatility (Barth et al., 1997 *Journal of American Chemical Society*, 119(18), 4149-4159; Shigeri et al., 2001 *Pharmacology & Therapeutics*, 91(2), 85-92; Ellis-Davies, 2003 *Enzymology*, 360, 226-238, all of which are incorporated herein by reference as if fully set forth). However, when synthetically accessible, the nitroindoline cages exhibit sufficient two-photon sensitivity and could be used to achieve non-linear spatial resolution.

Coumarin Cages.

In addition to nitroindolines, coumarin cages represent another option for a cage group with two-photon sensitivity. FIG. 21 illustrates cage groups derived from coumarin. Referring to FIG. 21, the coumarin groups can be used to cage a range of functional groups, including carboxylates, diols, sulfates, ketones and aldehydes, alcohols, thiols, and amines. Coumarin-based cages were reported to be particularly successful with caged phosphate, such as caged cAMP, RNA, and DNA (Furuta et al., 1995 The *Journal of Organic Chemistry*, 60(13), 3953-3956; Ando et al., 2001 *Nature Genetics*, 28, 317-325, all of which are incorporated by reference as if fully set forth). However, for neuroscientists, the ability to cage on carboxylates and amines is particularly useful. 6-bromo-7-hydroxycoumarin-4-ylmethoxycarbonyl (Bhc) has been used to photoprotect glutamate at both the carboxylate and the amine through a carbamate linker. Bhc-glutamate exhibits very efficient absorption ($\epsilon$=19,550 $M^{-1}$ $cm^{-1}$ at 369 nm) but modest quantum yield ($\Phi$=0.019, $\epsilon \times \Phi$=371 $M^{-1}$ $cm^{-1}$). When caged on the amine, the photochemical properties remain quite similar ($\epsilon$=17,470 $M^{-1}$ $cm^{-1}$ at 368 nm, $\phi$=0.019, $\phi \times \epsilon$=331 $M^{-1}$ $cm^{-1}$) (Furuta et al., 1999 *Proc. Natl. Acad. Sci.*, 96, 1193-1200, which is incorporated herein by reference as if fully set forth). In addition, Bhc is stable to aqueous hydrolysis and also exhibits high two-photon cross sections, allowing 2PE to be applied for highly localized photolysis.

Though these values are sufficient for in vitro application of Bhc-protected neurotransmitters, a notable limitation is their slow kinetics of uncaging at the amine. Referring to FIG. 14, coumarin-caged amines photolyze via a carbamate intermediate that must subsequently decarboxylate to generate the free amine. This decarboxylation was estimated to occur at a rate of $2 \times 10^2$ $s^{-1}$ at pH 7.2 by Rossi et al., 1997 *The Journal of Biological Chemistry*, 272, 32933-32939, which is incorporated herein by reference as if fully set forth. Though using a carbamate linker to cage an amine is a common route seen in with caged compounds, rate-limiting decarboxylation may occur. In addition, Bhc is highly fluorescent, which allows photolysis of the compound to be easily measured.

Coumarin-based cages have the advantage of being both two-photon sensitive (a limitation of the nitrobenzyl groups) and accessible to a wide range of functional groups (a limitation of the nitroindoline groups).

Ruthenium Cages.

The final cage group discussed is a ligated inorganic cage based on ruthenium photochemistry. Because common methods of caging at the amine resulted in slow photolysis kinetics (such as Bhc), cages that could release amines on a rapid timescale became a target for synthetic chemists.

FIG. 22 illustrates uncaging scheme of RuBi-GABA. Referring to FIG. 22, ruthenium-bipyridine-triphenylphosphine (RuBi) was first used to cage GABA at the amine by Zapata et al. RuBi-GABA exhibits sufficient absorption and quantum yield comparable to other successful cage groups ($\epsilon$=6,400 $M^{-1}$ $cm^{-1}$ at 368 nm, $\phi$=0.2, $\epsilon \times \phi$=1,280 $M^{-1}$ $cm^{-1}$). In addition, RuBi can be photolyzed at visible light wavelengths. The mechanism of uncaging proceeds through a single photochemical step, which results in faster substrate release when compared to caged amines through carbamate intermediates (Zayat et al., 2006 *Inorg. Chem.* 45, 1728-1731, which is incorporated herein by reference as if fully set forth). When applied in vitro, rise times of photolysis-evoked GABA currents ranged from much slower than spontaneously evoked responses to comparable in speed depending on where the compound was photolyzed. RuBi offers an alternative to caged amines that can circumvent some of the slow kinetics associated with carbamates.

The cages discussed are only a fraction of those in use, each with their own unique benefits and limitations. When evaluating cages in relation to each other, it would therefore be difficult to establish a rank order of cages. A cage for a caged GABA herein may be selected from these described herein or others in use.

Example 14 bis-($\alpha$-carboxy-2-nitrobenzyl)-gamma-aminobutyric acid

FIG. 23 illustrates a scheme of bis-CNB-GABA. Referring to FIG. 23, the many considerations necessary for designing caged compounds were incorporated into a completed project: synthesis and characterization of bis-protected GABA, caged at both the amine and the carboxylic acid with $\alpha$-carboxy-2-nitrobenzyl (bis-CNB-GABA). Many previously developed forms of caged-GABA have had considerable side effects that have limited their application, most notably a strong antagonistic effect at $GABA_A$ receptors before photolysis (Molnár & Nadler, 2000 *European Journal of Pharmacology*, 391, 255-262, which is incorporated herein by reference as if fully set forth). As a result, caged GABA has seen less in vitro application compared to other caged neurotransmitters, such as glutamate. Caged GABA design could change the overall structure of the caged compound to be even less similar to the GABA substrate, resulting in less antagonistic activity at $GABA_A$ receptors. In addition, the use of chemical two-photon uncaging maintains the non-linear release of the GABA substrate, while using a cage that is synthetically accessible and compatible with many different functional groups. Following the synthesis and subsequent photolysis in vitro, it was found by applicants that bis-CNB-GABA significantly reduces antagonism at $GABA_A$ receptors and represents a widely applicable form of caged GABA.

Example 15

Improvement of Caged GABA

One of the first caged GABAs used $\alpha$-carboxy-2-nitrobenzyl (CNB). FIG. 15 illustrates structure of CNB-GABA. CNB-GABA exhibits relatively good quantum yield (0.14), is soluble up to over 50 mM and has an uncaging speed in the microsecond range as was reported by Gee et al., 1994 *Journal of the American Chemical Society*, 116, 8366-8367, which is incorporated herein by reference as if fully set forth. However, the CNB cage group is not two-photon sensitive, meaning that the relationship between light exposure and GABA release was linear, and spatial resolution could be improved with two-photon or chemical two-photon uncaging.

Subsequent work on caged GABA has incorporated 2PE techniques. Matsuzaki et al. reported that CDNI-GABA exhibits high extinction coefficient (6,400 $M^{-1}$ $cm^{-1}$ at 330 nm) as well as high quantum yield (0.6, $\epsilon \times \Phi$=3,840 $M^{-1}$ $cm^{-1}$) (Matsuzaki et al., 2010 *Nature Chemical Biology*, 6, 255-257, which is incorporated herein by reference herein as if fully set forth). FIG. 24 illustrates structure of CDNI-GABA. Though the use of 2PE to uncage GABA is beneficial for improved spatial resolution, CDNI-GABA still suffers from some of the drawbacks of 2PE, such as requiring a more powerful laser.

Inorganic-based caging groups been reported by Verde et al. as a new form of caging amines, particularly GABA. Ruthenium-bipyridine-triphenylphosphine-GABA (RuBi-GABA) exhibits a high quantum yield and extinction coefficient ($\epsilon$=6,400 $M^{-1}$ $cm^{-1}$ at 424 nm, $\Phi$=0.2, $\epsilon \times \Phi$=1,280 $M^{-1}$ $cm^{-1}$). FIG. 22 illustrates uncaging scheme of RuBi-GABA. In addition, it can undergo two-photon excitation and photolyzes at visible light wavelengths, resulting in less phototoxicity to brain slices (Verde et al., 2008 *Frontiers in Neural Circuits*, 2, 1-8, which is incorporated herein by reference as if fully set forth).

Figure 25B:
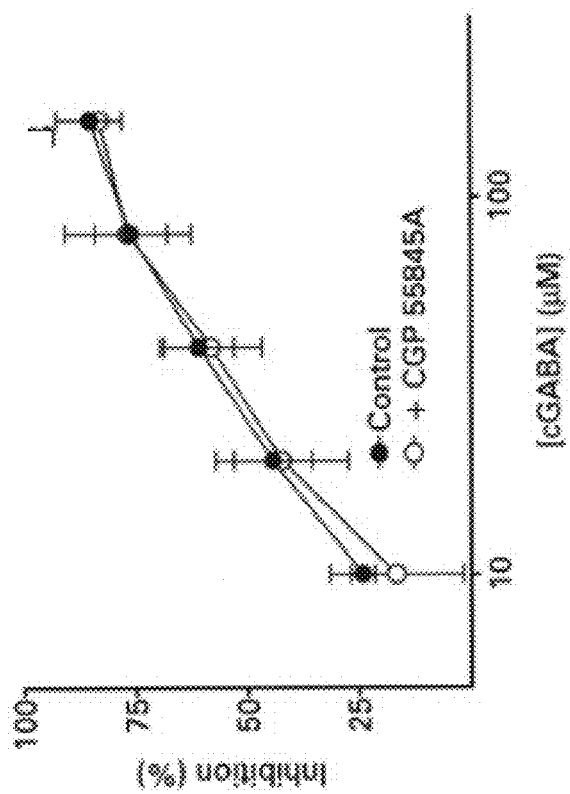
FIGS. 25A-25B illustrate CNB-GABA depressed, in a concentration-dependent manner, the monosynaptic IPSC evoked by stimulation of the molecular layer.
Figure 25A:
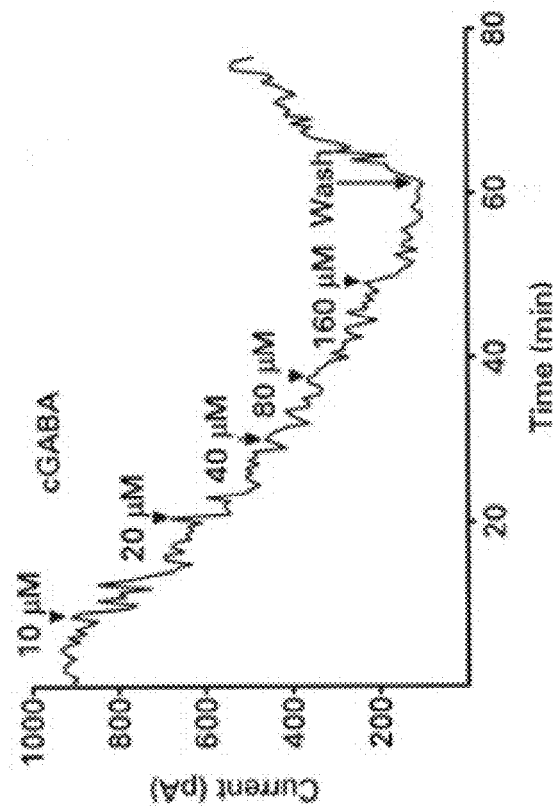

All forms of caged GABA developed thus far, including those discussed, have exhibited some extent of antagonistic activity for $GABA_A$ receptors. CNB-GABA has been shown to suppress GABA-evoked IPSC currents with an $IC_{50}$ of only 28 μM. FIGS. 25A-25B illustrate CNB-GABA depressed in a concentration-dependent manner the monosynaptic IPSC evoked by stimulation of the molecular layer as was observed by Molnár & Nadler, 2000. Referring to FIGS. 2A-25B, stimuli were delivered every 30 s. FIG. 25A illustrates that increasing the concentration of CNB-GABA progressively reduced the peak amplitude of the response recorded at a holding potential of 0 mV. FIG. 25B illustrates cumulative concentration-response curve. Referring to FIG. 25B, the IC for CNB-GABA was essentially the same in the absence (28±9 mM, mean±S.D., n=5) and presence (32±13 mM, mean±S.D., n=4) of the $GABA_B$ receptor antagonist CGP 55845A. (Molnár & Nadler, 2000 *European Journal of Pharmacology*, 391, 255-262, which is incorporated herein by reference as if fully set forth).

Figure 27:
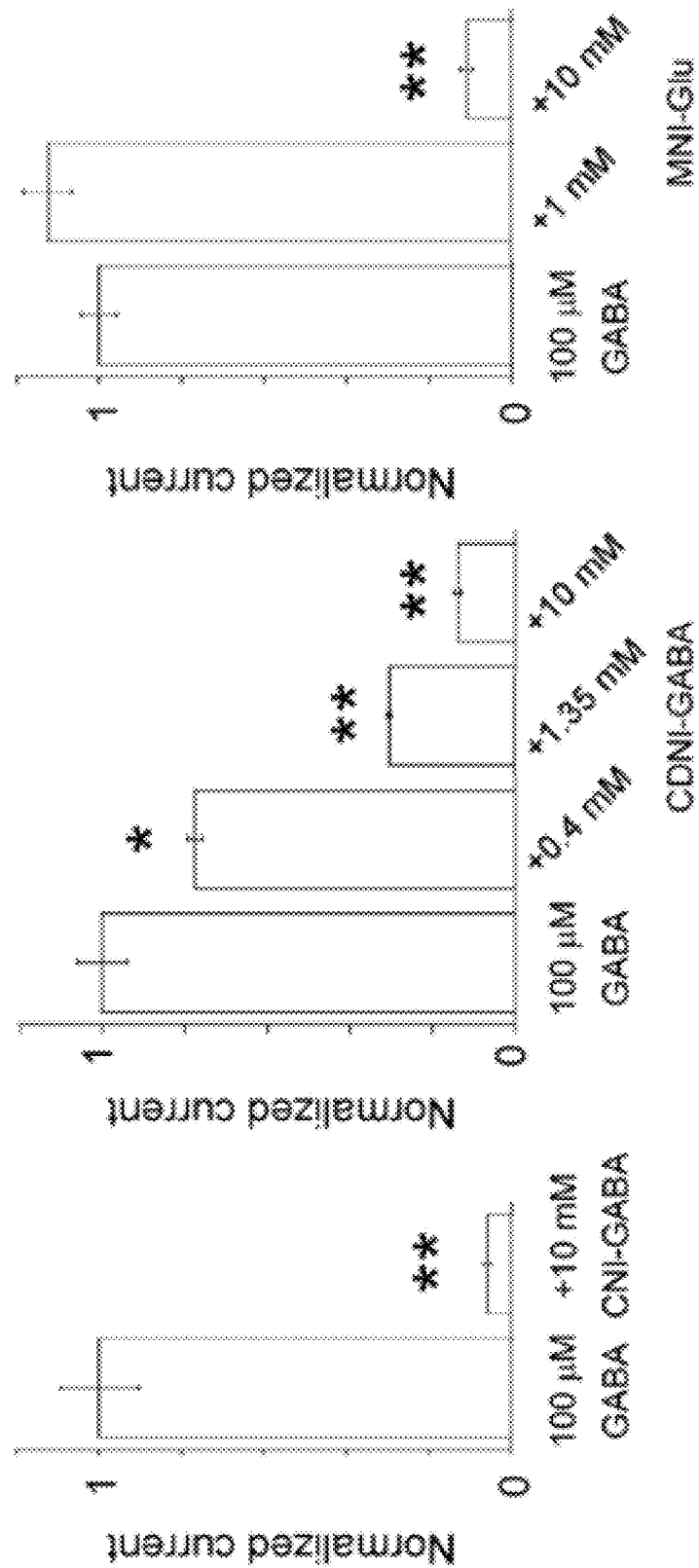
FIG. 27 illustrates a summary of the amplitudes of the current evoked by puff of 100 μM GABA and caged compounds around the soma.
Figure 28:
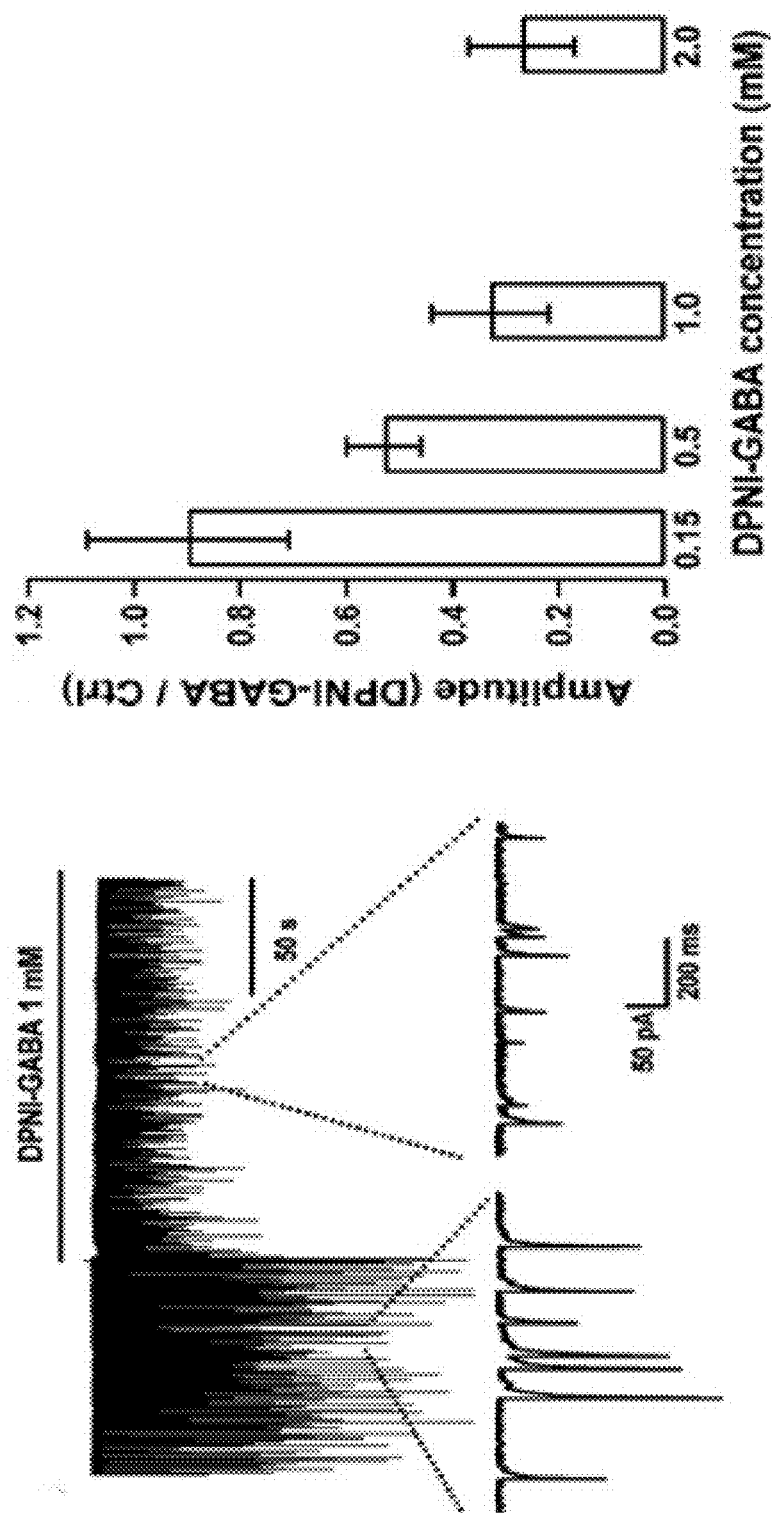
FIG. 28 illustrates the effects of NI-caged GABA and DPNI-GABA on amplitudes of miniature GABA synaptic currents.

GABA-evoked currents were reversibly eliminated at 200 μM, a very modest concentration for practical use of caged compounds. FIG. 26 illustrates whole-cell patch clamp recordings from dentate granule cells of rat hippocampal slices reported by Molnár & Nadler, 2000. Referring to FIG. 26, CNB-GABA at 200 mM did not significantly affect the EPSC evoked by stimulation of the perforant path. Holding potential of −80 mV. (Molnár & Nadler, 2000 *European Journal of Pharmacology*, 391, 255-262, which is incorporated herein by reference as if fully set forth, which is incorporated herein by reference as if fully set forth). Referring to FIG. 26, EPSC currents were unaffected by CNB-GABA but the antagonistic effect at the GABA receptors is significant enough to limit CNB-GABA usage for in vitro probing. Other forms of caged nitroindoline-caged GABA exhibit antagonism at varying concentrations as well. FIG. 27 illustrates summary of the amplitudes of the current evoked by puff of 100 μM GABA and caged compounds around the soma reported by Matsuzaki et al., 2010. The amplitude was normalized to the mean current that was induced by GABA application alone. Left panel illustrates control (n=7); +10 mM CNI-GABA (n=7). Central panel illustrates control (n=10); +0.4 mM CDNI-GABA (n=10), +1.35 mM CDNI-GABA (n=14); +10 mM CDNI-GABA (n=10). Right panel illustrates control (n=9); +1 mM MNI-Glu (n=4); +10 mM MNI-Glu (n=9). ** $p<0.0001$, * $p<0.01$ (Matsuzaki et al., 2010 *Nature Chemical Biology*, 6, 255-257, which is incorporated herein by reference as if fully set forth). Referring to FIG. 27, both CNI-GABA and CDNI-GABA exhibit >80% reduction in response at 10 mM. Though this is a much higher concentration compared to the $IC_{50}$ for CNB-GABA, CDNI requires a higher concentration when photolyzed in vitro because of its two-photon sensitivity. Because 10 mM is the concentration used for two-photon uncaging, this antagonism is still practically limiting. Other forms of nitroindoline-caged GABA have also exhibited detrimental antagonism (Matsuzaki et al., 2010 *Nature Chemical Biology*, 6, 255-257, which is incorporated herein by reference as if fully set forth). FIG. 28 illustrates the effects of NI-caged GABA and DPNI-GABA on amplitudes of miniature GABA synaptic currents as reported by Trigo et al., 2009. Referring to FIG. 28 (left), this panel illustrates recordings of miniature synaptic GABA currents in molecular layer interneurons before and during application of 1 mM DPNI-GABA. The initial inward current on diluting the cage into the bath was attributable to contaminating levels of GABA. Referring to FIG. 28 (right), the panel illustrates summary histogram from five cells of the block of spontaneous GABA currents by DPNI-GABA at different concentrations in the bath. (Trigo et al., 2009 *Journal of Neuroscience Methods*, 181, 159-169, which is incorporated herein by reference as if fully set forth).

Referring to FIG. 21 and FIG. 28, DPNI-GABA shows a >50% decrease in response at only 1 mM. Even RuBi-GABA (which has the largest and most hydrophobic cage group of those discussed) exhibits antagonistic $GABA_A$ receptor activity at concentrations above 20 μM, suspected to arise from the phosphine moiety that can bind to the receptor (Verde et al., 2008 *Frontiers in Neural Circuits*, 2, 1-8).

The antagonistic activity of these existing forms of caged GABA has largely inhibited its widespread use as a probing tool. Currently, there is no form of caged GABA that has overcome these obstacles to become realistically applicable in vitro.

For this reason, GABA would especially benefit from chemical two-photon caging because the additional cage is expected to make GABA less structurally similar to its substrate and therefore less likely to exhibit these antagonistic effects.

Example 16

Design and Synthesis of Double-Caged GABA

Because of the great potential advantages of double-caged GABA, choosing a cage and designing a synthesis route for it was the first necessary step. FIG. 23 illustrates a scheme of bis-CNB-GABA. Referring to FIG. 23, GABA itself has a notable synthetic limitation in that it only has two functional groups: an amine and a carboxylic acid. This means that it was necessary to choose a cage that could functionalize both. Amines are a less accessible functional group in the sense that fewer cages can successfully undergo photocleavable with amines, compared to carboxylates. This narrowed the selection of cages considerably. Currently, the most successful forms of caged GABA are CNB-GABA, CDNI-GABA, and RuBi-GABA. Though CDNI would be a desirable choice because of its two-photon sensitivity and efficient photocleavage, it is not synthetically accessible to amines. Furthermore, double-caging with RuBi is expected to render the compound too hydrophobic to be soluble in aqueous solutions. Given these limitations, CNB was the optimal choice for double-caging.

Several routes were attempted to synthesize bis-CNB-GABA. FIG. 31 illustrates the synthesis scheme for bis-(alpha-carboxy-2-nitrobenzyl)-GABA (bis-CNB-GABA) using one-step addition of both cage precursors. GABA backbone is shown in light gray.

Though esterification in the first step of each route proceeded with high yields and no purification, bromination proved somewhat inefficient. Attempts to brominate used varying amounts of radical initiator (AIBN) at varying time intervals. However, the reaction proceeded at best with an approximately 2:1 ratio of brominated product to starting material ester.

Figure 29:
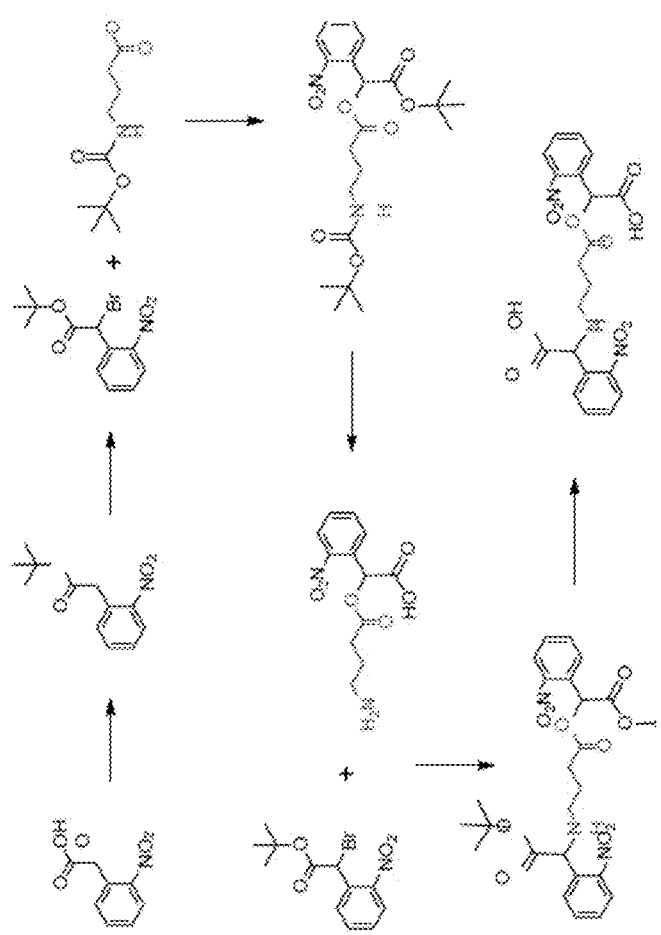
FIG. 29 illustrates a synthesis scheme for bis-(alpha-carboxy-2-nitrobenzyl)-GABA (bis-CNB-GABA) through a Boc protecting group. The GABA backbone is shown in light gray.
Figure 30:
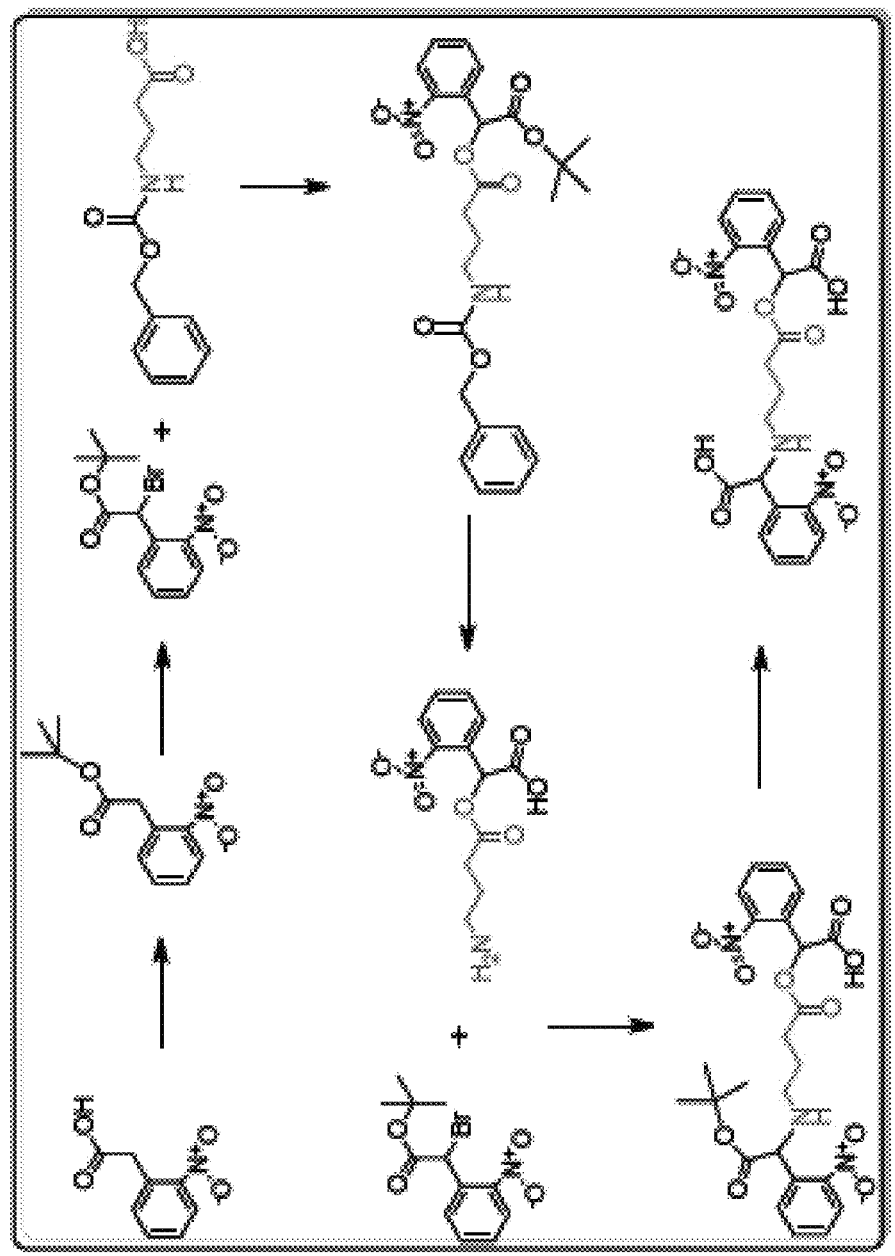
FIG. 30 illustrates a synthesis scheme for bis-(alpha-carboxy-2-nitrobenzyl)-GABA (bis-CNB-GABA) through a Cbz protecting group. The GABA backbone is shown in light gray.

Furthermore, several routes to append the GABA substrate were attempted. The first strategy entailed adding each cage separately in a stepwise manner. A Boc-protected GABA as well as a carboxybenzyl (Cbz) protected GABA were synthesized and reacted with the brominated intermediate to add the cage to the amine. However, addition of both Cbz-GABA and Boc-GABA to the brominated precursor was achieved sequentially. FIG. 29 illustrates synthesis scheme for bis-(alpha-carboxy-2-nitrobenzyl)-GABA (bis-CNB-GABA) through a Boc protecting group. GABA backbone is shown in light gray. FIG. 30 illustrates synthesis scheme for bis-(alpha-carboxy-2-nitrobenzyl)-GABA (bis-CNB-GABA) through a Cbz protecting group. GABA backbone is shown in light gray. Referring to FIG. 31, instead, both cages were added successfully at once, using GABA with no protecting groups and two equivalents of brominated intermediate. This afforded the precursor to the final product in good yields. Deprotection with trifluoroacetic acid produced bis-CNB-GABA as a TFA salt. The final product was shown to be 95% pure by HPLC analysis.

Example 17

Characterizing bis-CNB-GABA

Figure 32:
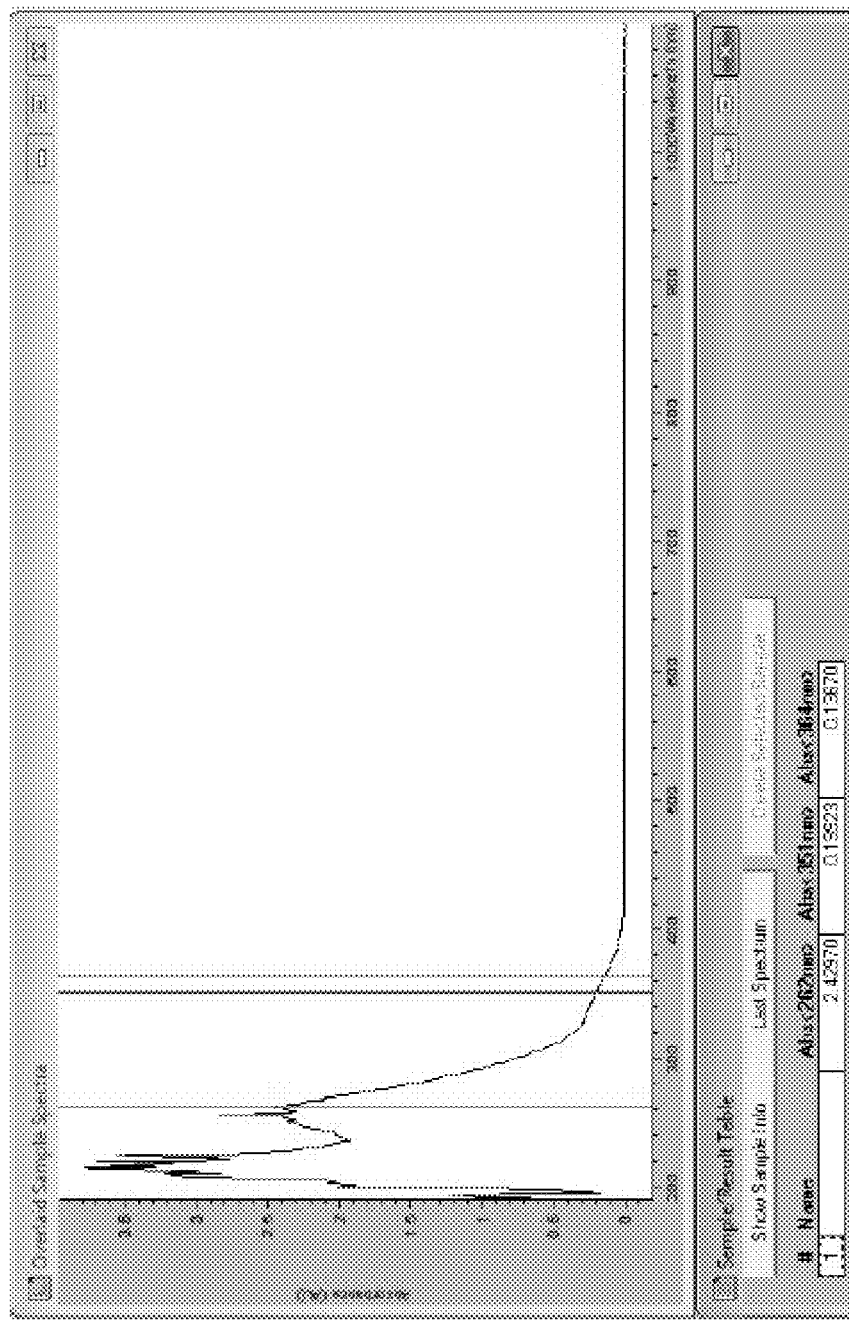
FIG. 32 illustrates an absorbance spectrum of bis-CNB-GABA at 322 mM.

Following successful synthesis of bis-CNB-GABA, it was necessary to quantify extinction coefficient and quantum yield. FIG. 32 illustrates absorbance spectrum of bis-CNB-GABA at 322 mM. Referring to FIG. 32, the first was accomplished simply by taking an absorbance spectrum of the compound. Extinction coefficient was then calculated from Beer's law. Bis-CNB GABA was found to have an extinction coefficient of 7,550 $M^{-1}$ $cm^{-1}$ at 262 nm.

Quantum yield was a more difficult characteristic to determine. Most published routes of determining quantum yield rely on exposing the compound to a known amount of light and calculating the percent conversion of caged compound to substrate. However, this often requires laser sources and equipment beyond the scope of available facilities. Therefore, it was necessary to develop a way to assess quantum yield with a more practical method. As an alternative, quantum yield was determined by exposing a compound to light alongside a caged compound of known quantum yield. The percent conversion to product of both can be determined, and quantum yield of the unknown caged compound can be calculated using the known quantum yield of the standard.

Figure 33:
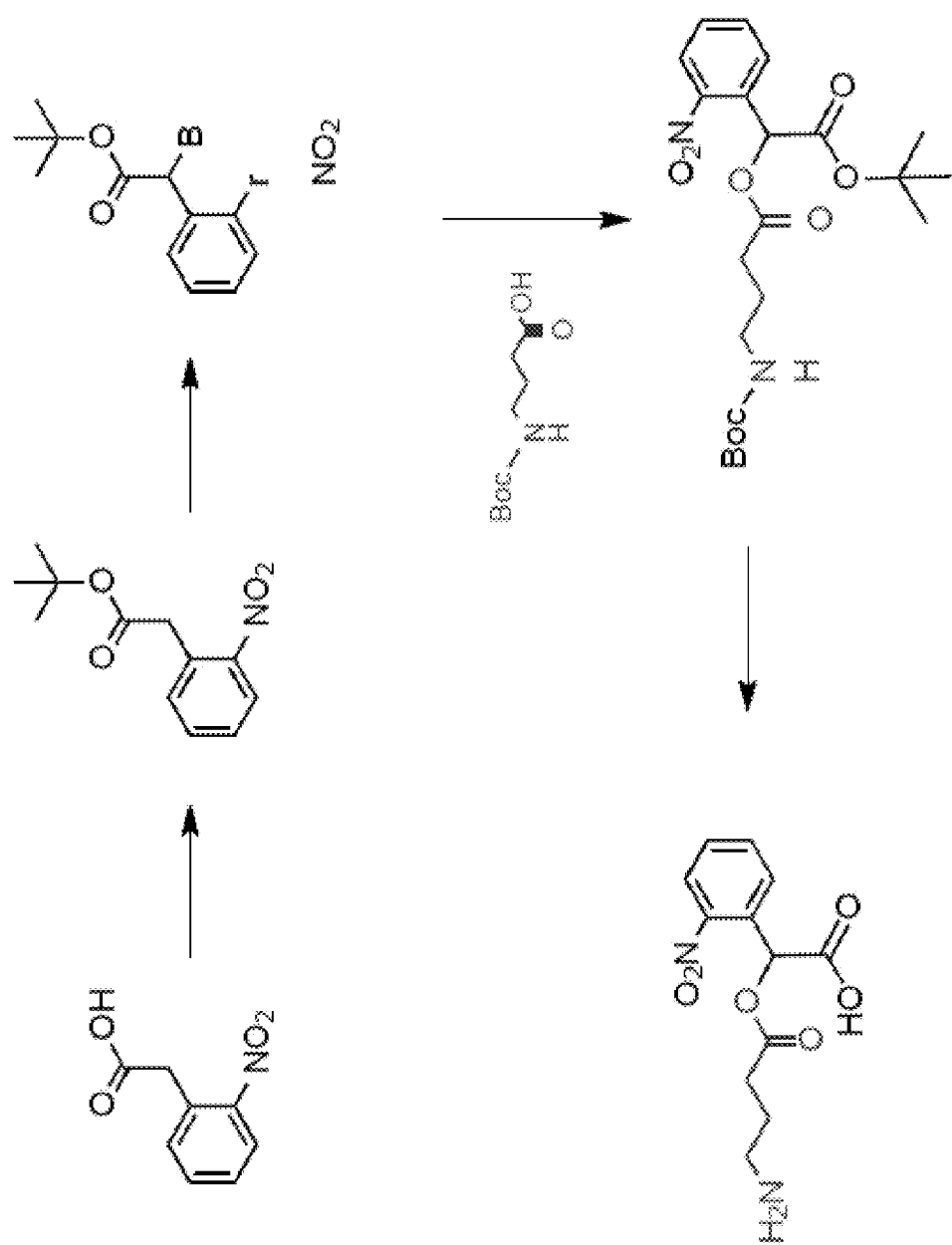
FIG. 33 illustrates a synthesis scheme for mono-CNB-GABA.

This method was employed using single-caged CNB-GABA, with a quantum yield of 0.14 (Matsuzaki et al., 2010 *Nature Chemical Biology*, 6, 255-257, which is incorporated herein by reference as if fully set forth). Mono-CNB-GABA was synthesized according to the route shown in FIG. 33. Referring to this figure, GABA backbone is shown in light gray.

Figure 34:
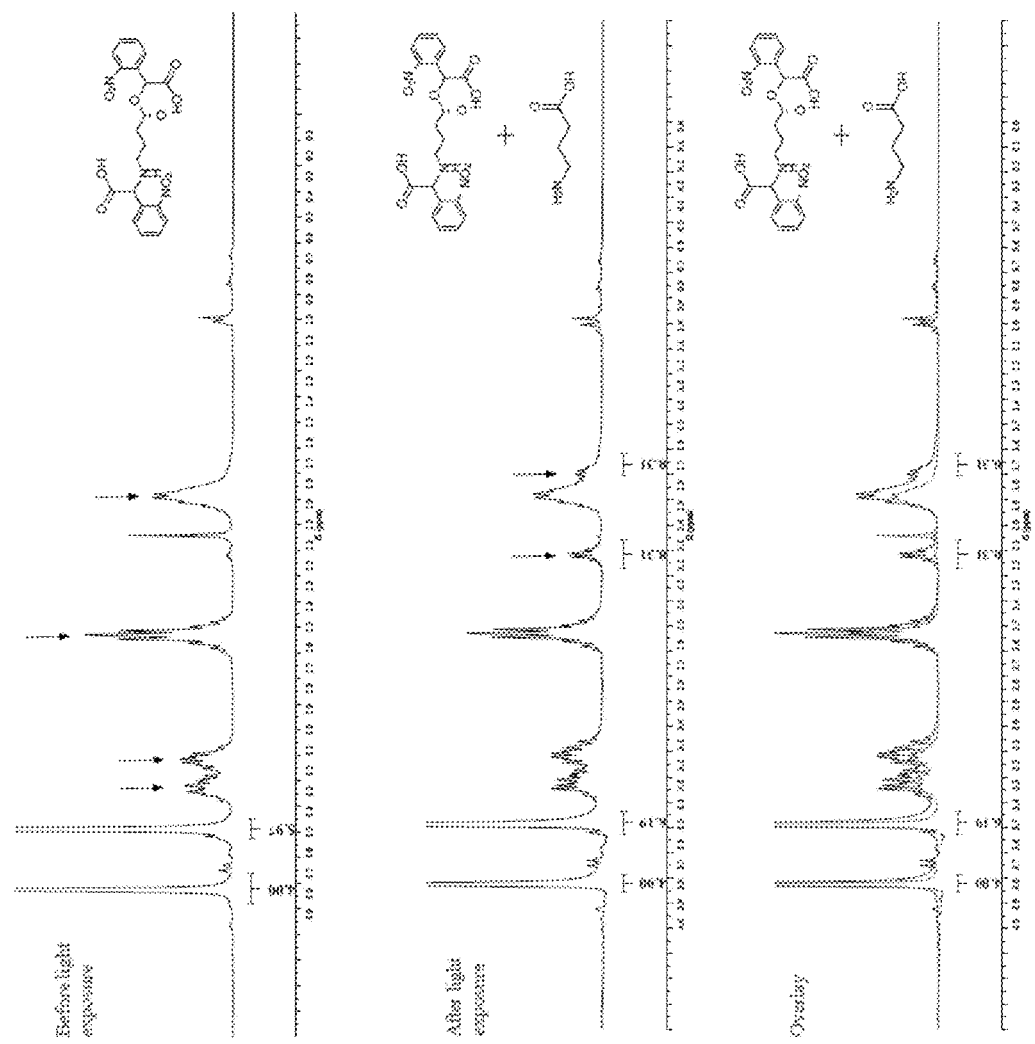
FIG. 34 illustrates NMR data used to determine quantum yield.

Equimolar amounts of single-caged GABA and bis-CNB-GABA were stirred in separate cuvettes in pH 7.0 phosphate buffer solution and exposed to 254 nm light for 16.5 minutes. An internal standard (1,2-dimethoxyethane) of known amount was then added to each solution, and the moles of GABA released from each compound was determined by $^1$HNMR. The peaks corresponding to GABA as well as those from the internal standard were then identified and integrated. From this, moles of GABA and percent conversion were calculated for both bis-CNB-GABA and mono-CNB-GABA. FIG. 34 illustrates NMR data used to determine quantum yield. Referring to FIG. 34, the histogram on the top illustrates bis-CNB-GABA before light exposure. Arrows denote methylene peaks of bis-CNB-GABA. Integrated peaks in each spectrum correspond to di-methoxyethane, used as an internal standard. The histogram in the middle illustrates bis-CNB-GABA after 16.5 minutes of exposure in photobox at 254 nm. Arrows denote peaks that correspond to GABA. The histogram on the bottom illustrates overlay of top and middle spectra. The lack of extraneous peaks in the 0-4 ppm range was notable after light exposure. Still referring to FIG. 34, the $^1$HNMR spectrum showed clear production of GABA peaks and importantly, no new peaks other than CNB byproduct after UV exposure. Using this method, the quantum yield of bis-CNB-GABA was found to be 0.07.

Solubility data was important to obtain before attempting to use the compound in neural tissue. This was accomplished by dissolving a known amount of bis-CNB-GABA in pH 7.0 phosphate buffer solution. Bis-CNB-GABA was soluble up to 17 mM in the buffer solution.

Example 18

In Vitro Results

Figure 35:
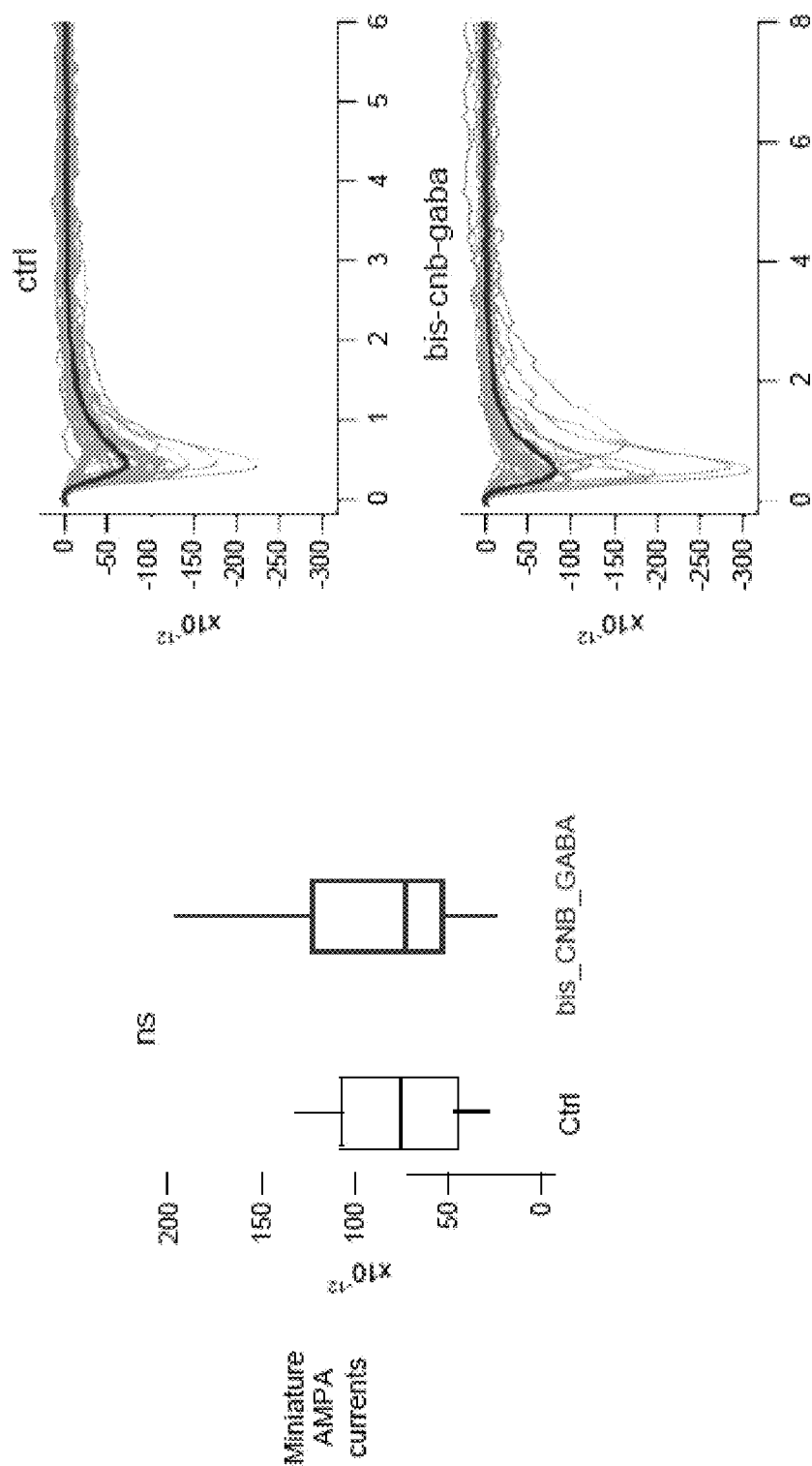
FIG. 35 illustrates that bis-CNB-GABA has no significant effect on amplitude of miniature AMPA currents at 1.223 mM.
Figure 36:
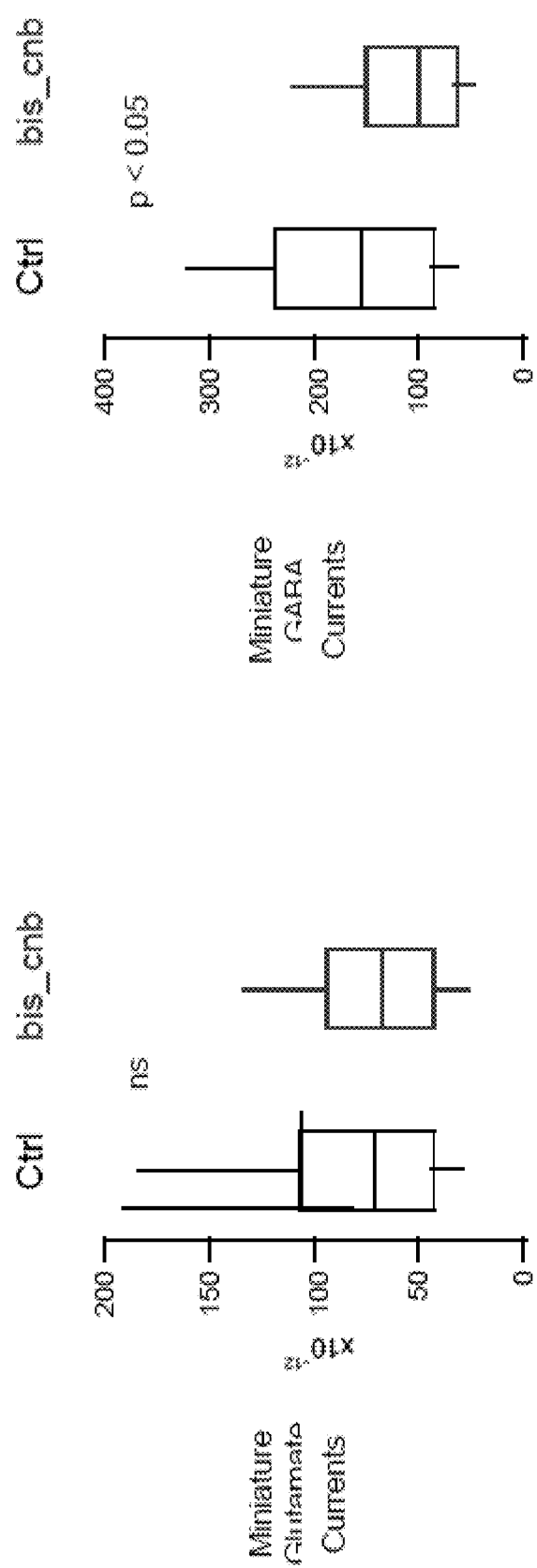
FIG. 36 illustrates effects of 1 mM bis-CNB-GABA on spontaneously evoked miniature glutamate and miniature GABA currents in cerebellar interneuron

Bis-CNB-GABA was applied in vitro. Currents were recorded from cerebellar interneurons. FIG. 35 illustrates that bis-CNB-GABA has no significant effect on amplitude of miniature AMPA currents at 1.223 mM. FIG. 35 (right) illustrates response traces before and after application of bis-CNB-GABA. FIG. 35 (left) illustrates summary of data. FIG. 36 illustrates effects of 1 mM bis-CNB-GABA on spontaneously evoked miniature glutamate and miniature GABA currents in cerebellar interneuron. FIG. 36 (left) illustrates that bis-CNB-GABA has no significant effect on spontaneously-evoked AMPA currents. FIG. 36 (right) illustrates that bis-CNB-GABA shows a ~33% decrease in miniature GABA response amplitude. FIG. 39 illustrates that bis-CNB-GABA has no significant effect on spontaneously-evoked AMPA currents (raw traces: top right, summary: top left) and exhibits ~33% reduction of GABA currents (raw traces: bottom right, summary: bottom left).

Figure 37:
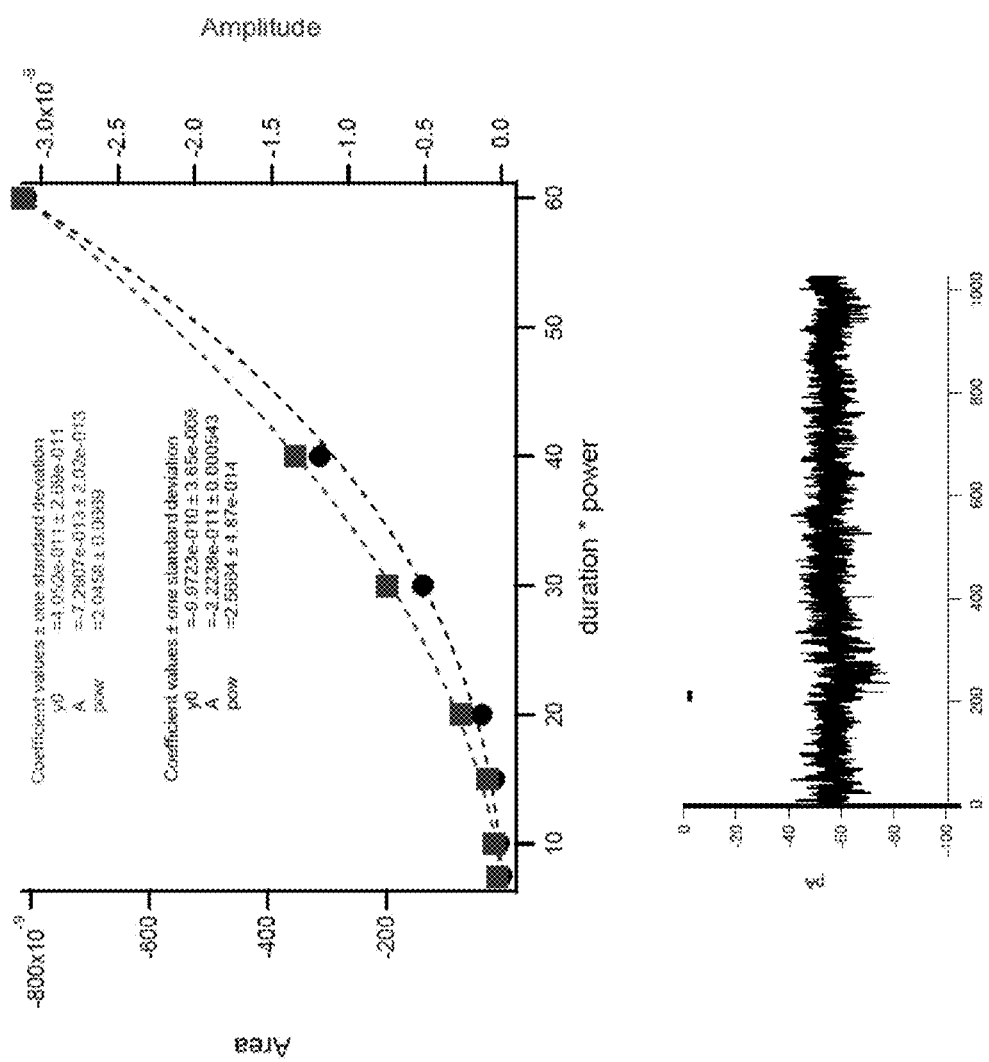
FIG. 37 illustrates effects of uncaging.

Referring to FIG. 35, FIG. 36 and FIG. 39, Bis-CNB-GABA had no significant effect on miniature AMPA currents at 1.233 mM and 1.0 mM concentrations, providing strong evidence that bis-CNB-GABA does not interfere with excitatory responses. FIG. 37 illustrates effects of uncaging. Referring to FIG. 37 (top), this graph illustrates square relationship between current response amplitude (light gray) and laser power. Square relationship is also observed between area of observed response and laser power (black). Both are suggestive of a two-photon level of non-linear spatial resolution. Referring to FIG. 37 (bottom), the graph illustrates uncaging at 365 nm with LED in the presence of 3 mM gabazine.

Referring to FIG. 37 (top), in addition, photolysis of the compound revealed a square relationship between laser power and current amplitude as well as area of GABA release. This supports the predicted non-linear release of bis-CNB-GABA, suggesting improved localization and spatial resolution compared to the single-caged analog.

Figure 38C:
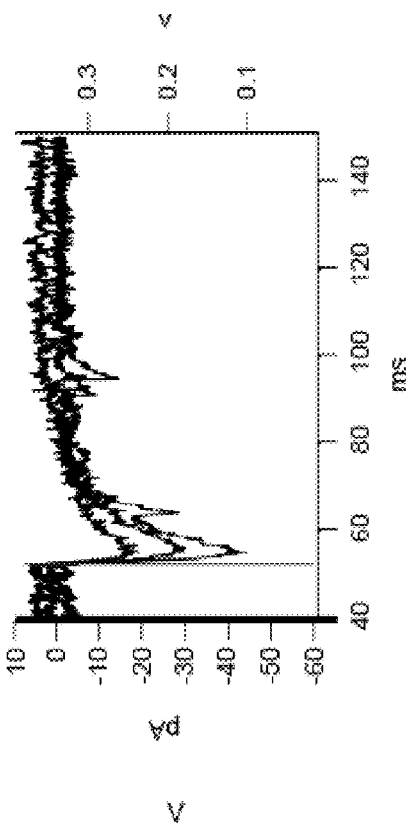
FIGS. 38A-38D illustrate kinetics of photolysis-evoked cellular responses.
Figure 38D:
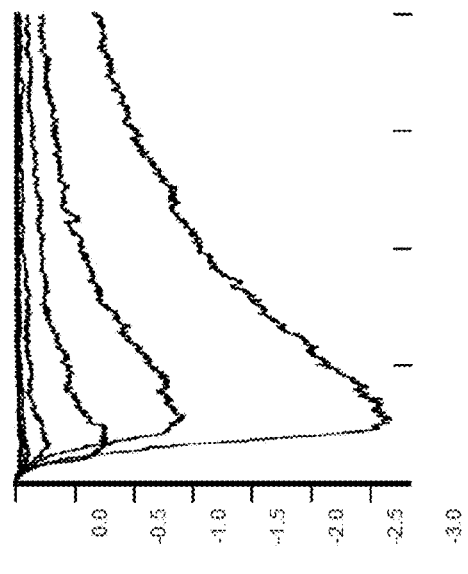
Figure 38A:
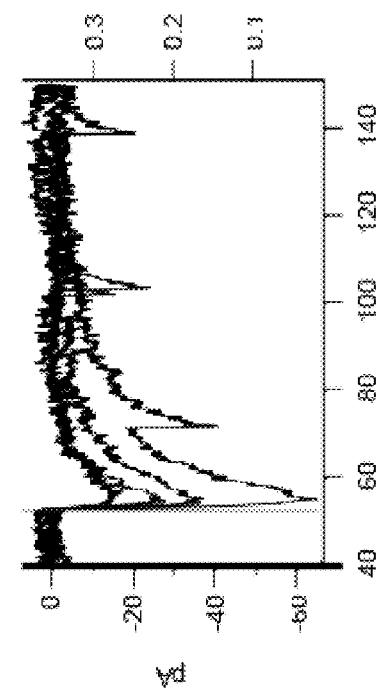
Figure 38B:
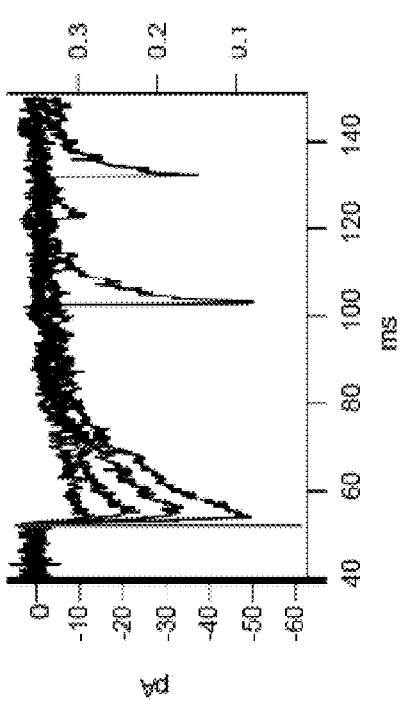

FIGS. 38A-38D illustrate kinetics of photolysis-evoked cellular responses. FIGS. 38A-38C illustrate uncaging with 405 nm laser at three different locations. Referring to these figures, light gray lines symbolize time point of uncaging. Each trace shows both photolysis-evoked responses as well as spontaneous firing. FIG. 38D illustrates uncaging with 365 nm LED laser.

Referring to FIGS. 38A-38D, photolysis of bis-CNB-GABA generated a rapid release of GABA, evidenced by the fast rise time of GABA-induced currents upon photolysis. Referring to FIG. 37 (bottom), photolysis in the presence of 3 M gabazine eliminated these responses. The currents evoked by bis-CNB-GABA photolysis mirrored the kinetics of spontaneously evoked GABA currents, shown at later time points in FIGS. 38A-38C. This rise time of approximately 2 ms therefore is a significant improvement in uncaging speed, particularly for a compound caged at the amine. Previous forms of caged amines have frequently operated through a carbamate linker, which uncages via an intermediate that undergoes slow decarboxylation in the 7 ms time range, long enough to reduce spatial resolution. Therefore, bis-CNB-GABA resolves an important kinetic limitation that has plagued some forms of amine-caged GABA compounds as well.

Referring to FIG. 37 and FIG. 39, despite being double-caged, bis-CNB-GABA was shown to have a residual antagonistic effect on $GABA_A$ receptors. At 1 mM, bis-CNB-GABA showed ~33% decrease in GABA current response. However, this is a significant improvement over mono-CNB-GABA, which has an $IC_{50}$ of 28 µM as shown in FIGS. 27A-27B. This implies that only 14 µM of mono-CNB-GABA would be required to generate this 33% reduction in response, compared to 1 mM of bis-CNB-GABA. Bis-CNB-GABA therefore exhibits 70-fold less affinity than its mono-caged analog. Referring to FIG. 27 and FIG. 28, furthermore, bis-CNB-GABA shows 4-fold less antagonistic binding compared to CDNI-GABA ($IC_{50}$=450 µM), which would show a 33% reduced response at only 220 µM (FIG. 27), and 4-fold less antagonism compared to DPNI-GABA ($IC_{50}$=470 µM), which shows a 33% reduction at 230 µM (FIG. 28). (Matsuzaki et al., 2010 Nature Chemical Biology, 6, 255-257, which is incorporated herein by reference as if fully set forth). Data is summarized in Table 1.

TABLE 1

$IC_{50}$ and $IC_{33}$ of several caged compounds.

| Caged | $IC_{50}$ (mM) | $IC_{33}$ |
|---|---|---|
| mono-CNB- | 0.0 | 0.014 |
| CDNI-GABA[b] | 0.4 | 0.22 |
| DPNI-GABA[c] | 0.4 | 0.23 |
| MNI-glu[b] | 1.1 | 0.37 |
| bis-CNB-GABA | 2.0 | 1.0 |

Values are calculated from $q=[j]/[j]+IC_{50}$, where q=proportional decrease in response amplitude (ex. $IC_{33}$ corresponds to q=033); and [j]=concentration of caged compound based on data reported by a: Molnár and Nadler, 2000 European Journal of Pharmacology, 391, 255-262; b: Matsuzaki et al. 2010 Nature Chemical Biology, 6, 255-257; and c: Trigo et al, 2009 Journal of Neuroscience Methods, 181, 159-169, all of which are incorporated herein by reference as if fully set forth.

It should be noted that the appropriate comparison of antagonism is between mono-CNB-GABA and bis-CNB-GABA, rather than DPNI-GABA or CDNI-GABA. The data show that the addition of a second cage to mono-CNB-GABA directly reduces antagonism by a factor of 70. It is predicted that bis-DPNI-GABA and bis-CDNI-GABA would exhibit even greater reduction of antagonism compared to their single-caged analogs, given that DPNI and CDNI are bulkier cage groups than CNB, though this cannot be concluded unless the compounds are synthesized and assayed for $GABA_A$ antagonism.

Bis-CNB-GABA therefore represents a significant reduction in GABA receptor antagonism that has plagued all previous forms of caged GABA. However, it is important to note that this antagonistic effect could be due to either the bis-caged compound itself or residual amounts of mono-caged GABA, possibly generated by spontaneous photolysis of only one of the two cages during storage or handling. Given the functionalization of both the amine and the carboxylate, it seems unlikely that the antagonistic effect is due to bis-CNB-GABA itself due to its two bulky cage groups. Rather, the more likely candidate is mono-CNB-GABA, especially given that even 1% decomposition of 1 mM bis-CNB-GABA to mono-CNB-GABA during storage or exposure to visible light would generate 10 µM of mono-CNB-GABA, enough to cause this 25% antagonistic effect.

If observed antagonism is in fact due to small amounts of mono-CNB-GABA, then any antagonism reported will not be truly reflective of bis-CNB-GABA itself. It will instead be the effective antagonism of bis-CNB-GABA used in practice, which can be due to double-caged GABA and small amounts of spontaneously generated single-caged GABA due to storage or premature light exposure.

Nevertheless, the data thus far has provided compelling evidence for two significant advantages of bis-CNB-GABA. First, it is far less antagonistic for $GABA_A$ receptors compared to the single-caged analog. Second, it exhibits highly rapid kinetics, mimicking the rise time of spontaneously evoked currents. These two results therefore represent a significant contribution of bis-CNB-GABA to the caged neurotransmitter literature. Bis-CNB-GABA is there a novel optical probing tool that is practically useful for in vitro stimulation.

Example 19

Bis-CNB-GABA Synthesis and Physical Properties

The synthesis of bis-CNB-GABA is outlined in Scheme 1. Nitrophenylacetic acid (1) was converted to its t-butyl ester, then brominated with NBS and AIBN to generate benzyl bromide 2. The latter was used to alkylate GABA simultaneously at both the amine and the acid positions (3); a final deprotection generated bis-CNB-GABA (4) as a tan powder. This material was shown by $^1$H NMR analysis to be >99% pure, and to contain <0.2% residual GABA. A portion of the product was further purified by preparative HPLC. Notably, this synthetic route is comparable in ease to that of a single-caged GABA. Thus, bis-CNB-GABA is readily accessible from commercially available materials.

Bis-CNB-GABA exhibits maximal absorbance at 262 nm (e=7550 $M^{-1}$ $cm^{-1}$). Relative to mono-O-CNB-GABA as a reference standard to quantify conversion, the quantum yield (using 254 nm light) was 0.15 at the O-position and 0.032 at the N-position; these findings are similar to the quantum yields determined at 308 nm excitation for the corresponding mono-CNB-GABA compounds (Gee, K. R.; Wieboldt, R.; Hess, G. P. J. Am. Chem. Soc. 1994, 116, 8366-8367; Wieboldt, R.; Ramesh, D.; Carpenter, B. K; Hess, G. P. Biochemistry, 1994, 33, 1526-1533, which are incorporated herein by reference as if fully set forth).

Finally, bis-CNB-GABA is soluble in pH 7.0 phosphate buffer solution up to 17 mM, at levels comparable to bis-CNB-glutamate (Pettit, D. L.; Wang, S. S-H.; Gee, K. R.; Augustine, G. J. Neuron. 1997, 19, 465-471, which is incorporated herein by reference as if fully set forth).

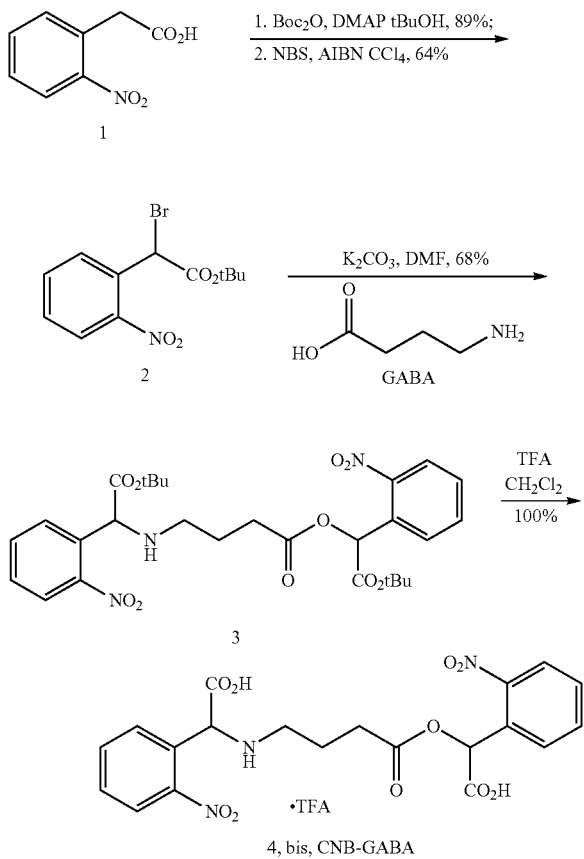

Scheme 1. Synthesis of bis-CNB-GABA.

Example 20

Effects of Uncaging to Evoke Currents in Molecular Layer Interneurons

The biological properties of our synthetic bis-CNB-GABA were evaluated using whole-cell patch recording from cerebellar molecular layer interneurons.

FIGS. 42A-42E illustrate physiological responses to photolysis of bis-CNB-GABA. FIG. 42A illustrates a cerebellar molecular layer interneuron visualized using Alexa 488 in the patch recording electrode solution. Referring to FIG. 42A, bis-CNB-GABA (0.6 mM) was photolyzed with a 405 nm laser spot in 3 different locations (indicated by 1, 2 and 3). Still referring to FIG. 42A, laser-evoked GABAergic currents are shown on the right panel. Still referring to FIG. 42A, gray traces show individual sweeps and black traces are averages. Still referring to FIG. 42A, the gray sweep at bottom indicates the laser flash (1 ms duration, intensity 5 mW) as recorded using a photodiode. FIG. 42B illustrates bis-CNB-GABA (1.4 mM) was photolyzed with a 3650 nm LED at progressively higher flash energies (0.25-1.1 mW, 5-50 ms, 1.25-55 µJ). FIG. 42C illustrates the same experiment as shown in FIG. 42B with Responses to mono-CNB-GABA (50 µM). FIG. 42D illustrates normalized current as a function of relative LED flash energies plotted on a log-log scale. FIG. 42E illustrates laser-evoked whole-cell current recorded in the absence and presence of 3 µM gabazine, a GABA receptor antagonist. Referring to FIG. 42E, a larger flash energy was used in the presence of gabazine.

Referring to FIG. 42A, molecular layer interneurons receive excitatory glutamatergic synapses, as well as inhibitory GABAergic synapses that show a pronounced level of spontaneous activity (gray traces). The effects of bis-CNB-GABA on these synaptic currents were tested. Referring to FIGS. 44A-44E, in the presence of bis-CNB-GABA, photolysis—using either a UV high intensity LED focused to the back focal plane of the objective or a minimized 405 nm laser spot—produced currents (FIGS. 44B-44D) that were reversibly eliminated in the presence of 3 µM of the GABAA receptor antagonist, gabazine (FIG. 42E).

Referring to FIG. 42D, the current amplitude evoked by photolysis of bis-CNB-GABA was related to laser flash energy by a square relationship (log–log slope=2.2±0.1, n=3 cell bodies). By contrast, the relationship for mono-O-CNB-GABA was close to linear (log-log slope=1.3±0.1, n=3). For these measurements, evoked currents were normalized to the maximum current observed in the same neuron. Moreover, the integrated evoked current over time showed a second power relationship with respect to laser energy. These power laws are consistent with a process in which each molecule of bis-CNB-GABA must cumulatively undergo two uncaging reactions in order to release an active $GABA_A$ agonist. This result is predicted by localized, non-linear release of GABA at the laser's focus spot, and is in line with the localized release and spatial resolution seen in previous applications of chemical two-photon uncaging (Pettit, D. L.; Wang, S. S-H.; Gee, K. R.; Augustine, G. J. Neuron. 1997, 19, 465-471; Sarkisov., D. V.; Gelber, S. E.; Walker, J. W.; Wang, S. S.-H. J. Biol. Chem. 2007, 282, 25517-25526, both of which are incorporated by reference as if fully set forth).

Example 21

Laser-Evoked GABA Responses

To test whether bis-CNB-GABA-evoked responses resemble physiological events in their kinetics, we measured the kinetic properties of flash responses. For responses comparable in size with spontaneous inhibitory postsynaptic currents (IPSCs), the 10-90% rise time was 2.2±0.6 ms (n=10)—somewhat longer than the flash duration of 1.0 ms. This rise time is consistent with the dark reaction time (1.5 ms) for the slower cage, N-mono-CNB-GABA (Wieboldt, R.; Ramesh, D.; Carpenter, B. K; Hess, G. P. Biochemistry, 1994, 33, 1526-1533, which is incorporated herein by reference as if fully set forth). The falling $t_{1/2}$ was 24.2±8.2 ms (n=10). These rates approach those of spontaneous events and are among the fastest described for other GABA cages. In some recordings (for example FIG. 43A, responses at sites 1 and 3), the kinetics of laser-evoked events were nearly indistinguishable from those of spontaneous IPSCs, perhaps because of short electronic distances between the uncaging site and the recording electrode. In summary, photo-uncaging of bis-CNB-GABA was sufficiently rapid to mimic synaptic events.

Example 22

Effects of Bis-CNB-GABA on Endogenous Synaptic Communication

In order to evaluate the viability of bis-CNB-GABA as a probe compound, three measures of the potential undesirable effects of both mono- and bis-caged GABA analogs were made.

FIGS. 43A-43E illustrate quantification of unwanted effects of caged GABA. Referring to FIGS. 43A-43E, first, changes in whole-cell holding current under voltage clamp were monitored while caged GABA compounds were applied by bath application or by local perfusion as per Civillico, E. F.; Shoham, S.; O'Connor, D. H.; Sarkisov, D. V.; Wang, S. S.-H. Cold Spring Harb. Protoc. 2012, which is incorporated herein by reference as if fully set forth). FIG. 43A illustrates voltage-clamp recordings from cerebellar interneurons exposed to caged GABA. Referring to this figure, upper trace corresponds to 1 mM bis-CNB-GABA; middle trace corresponds to 0.1 mM mono-O-CNB-GABA; bottom trace corresponds to 1 mM DPNI-GABA. Referring to FIG. 43A, (right) expanded traces illustrating the detailed effects on steady-state holding current and fluctuations in holding current were observed. FIG. 43B illustrates effects of caged GABA on spontaneous IPSCs and excitatory postsynaptic currents (EPSCs). Referring to FIG. 43B, IPSCs and EPSCs were identified and separated based on kinetic criteria. FIG. 43B (left) illustrates box plots of spontaneous postsynaptic current amplitudes in control conditions and in the presence of 1 mM bis-CNB-GABA. Referring to FIG. 43B (left), boxes show interquartile range and whiskers show full range of values. FIG. 43B (right) illustrates individual traces (gray) and average (block) of detected spontaneous IPSCs and EPSCs. FIG. 43C illustrates dependence of spontaneous IPSC amplitude on bis-CNB-GABA concentration. Referring to FIG. 43C, the curve indicates a fit with KD=2.5±0.2 mM, nH=0.93±0.09. FIG. 43D illustrates comparison of effects of mono-O-CNB-GABA (0.1 mM) and bis-CNB-GABA (1.0 mM, except for 0.4 mM for IPSCs) on spontaneous IPSC amplitude, standard deviation of holding current (noise), and holding current (Ihold). FIG. 43E illustrates spontaneous EPSC size was unaffected by bis-CNB-GABA at all concentrations tested. Referring to FIGS. 43A and 43D, under these conditions, mono-O-CNB-GABA (0.1 mM) led to increases of 66±47 pA (mean±SD, n=6) in inward holding current at −60 mV ($I_{hold}$). This inward current presumably arises either via indirectly evoked increases in excitation or from direct activation of $GABA_A$ receptors (by residual free GABA in the caged compound solution or by mono-O-CNB-GABA, which may itself have partial agonist activity). See Dellal., S. S.; Luo, R.; Otis, T. S. J. Neurophysiol., 2012, 107, 2958-2970, which is incorporated herein by reference as if fully set forth.

Still referring to FIG. 43A, similar, though less pronounced, results have been observed with DPNI-GABA (see Trigo, F. F.; Papageorgiou, G.; Corrie, J. E. T.; Ogden, D. J. Neurosci. Meth., 2009, 181, 159-169, which is incorporated herein as if fully set forth). Referring to FIG. 43D, in contrast, application of bis-CNB-GABA (raw product, 0.4 to 2.0 mM) evoked no detectable change in the holding current (ratio of holding current drug/control=1.0±0.3, n=14, p=0.7, Mann-Whitney test) or in its standard deviation, which is a measure of steady-state channel noise (from 3.0±0.5 to 3.2±0.8 pA, n=14, p=0.3) measured during periods of no spontaneous currents. No difference in induced holding current was seen between raw product and HPLC-purified product.

Referring to FIG. 43B, the effects of bis-CNB-GABA on spontaneous IPSCs was next measured. At 1 mM, mono-O-CNB-GABA ($IC_{50}$=28 µM) triggered a dramatic decrease in the rate of spontaneous IPSCs, presumably due to inhibition of connected MLIs (Molnár, P.; Nadler, J. V. Eur. J. Pharmacol. 2000, 391, 255-262, which is incorporated herein by reference as if fully set forth). Referring to FIG. 43B, in contrast, addition of bis-CNB-GABA served to reduce GABA current amplitudes by approximately one-third (FIG. 43B, top; 0.4 to 2.0 mM; ratio of amplitudes during drug/control: 0.68±0.17, n=14). Referring to FIG. 43C, the concentration-dependence of the reduction yielded an estimated $IC_{50}$ of 2.5 mM. This $IC_{50}$ is, in fact, a lower bound; the material tested was crude product, which may contain minute amounts of mono-CNB-GABA. Bis-CNB-GABA therefore exhibits at least 100-fold lower affinity compared to its mono-caged analog. Moreover, the 10-90% rise time of IPSCs was unaffected by bis-CNB-GABA application (control, 0.44±0.13 ms vs. bis-CNB-GABA, 0.44±0.11 ms), in contrast with DPNI-GABA, which prolongs rise times (Trigo, F. F.; Papageorgiou, G.; Corrie, J. E. T.; Ogden, D. J. Neurosci. Meth., 2009, 181, 159-169, which is incorporated herein by reference as if fully set forth). Taken together, these findings are consistent with the hypothesis that bis-CNB-GABA shows virtually no antagonist activity at submillimolar concentrations.

As a third and final test of the synaptic effects of bis-CNB-GABA, we measured its impact on spontaneous glutamatergic postsynaptic currents (EPSCs) recorded from MLIs. Referring to FIGS. 43B and 43E, with this configuration, no change in the amplitude of the EPSCs was observed (FIG. 43B, bottom) even with concentrations of bis-CNB-GABA up to 2 mM (FIG. 43E, p=0.4, Spearman rank order correlation test).

At concentrations of 1 mM, doubly-caged bis-CNB-GABA was found to have minimal or no effects on holding current, IPSCs, or EPSCs.

Example 23

Spontaneous Rate of Hydrolysis of Bis-CNB-GABA Vs. Mono-O-CNB-GABA

The hydrolytic stability of bis-CNB-GABA under normal handling conditions was examined. Accordingly, we prepared samples of bis-CNB-GABA and mono-O-CNB- GABA were prepared in aqueous buffer (23° C., 12 mM, pH=7.4), stored the samples under fluorescent room lights, and determined accumulation of deprotected GABA at 1-day intervals.

The mechanism of photo-decaging of the CNB group is an active area of study; several pathways are available to caged amines and caged carboxylate derivatives (Corrie, J. E. T.; Munasinghe, V. R. N.; Trentham, D. R.; Barth, A. Photochem. Photobiol. Sci. 2008, 7, 84-97, which is incorporated herein by reference as if fully set forth).

Figures 44A, 44B:
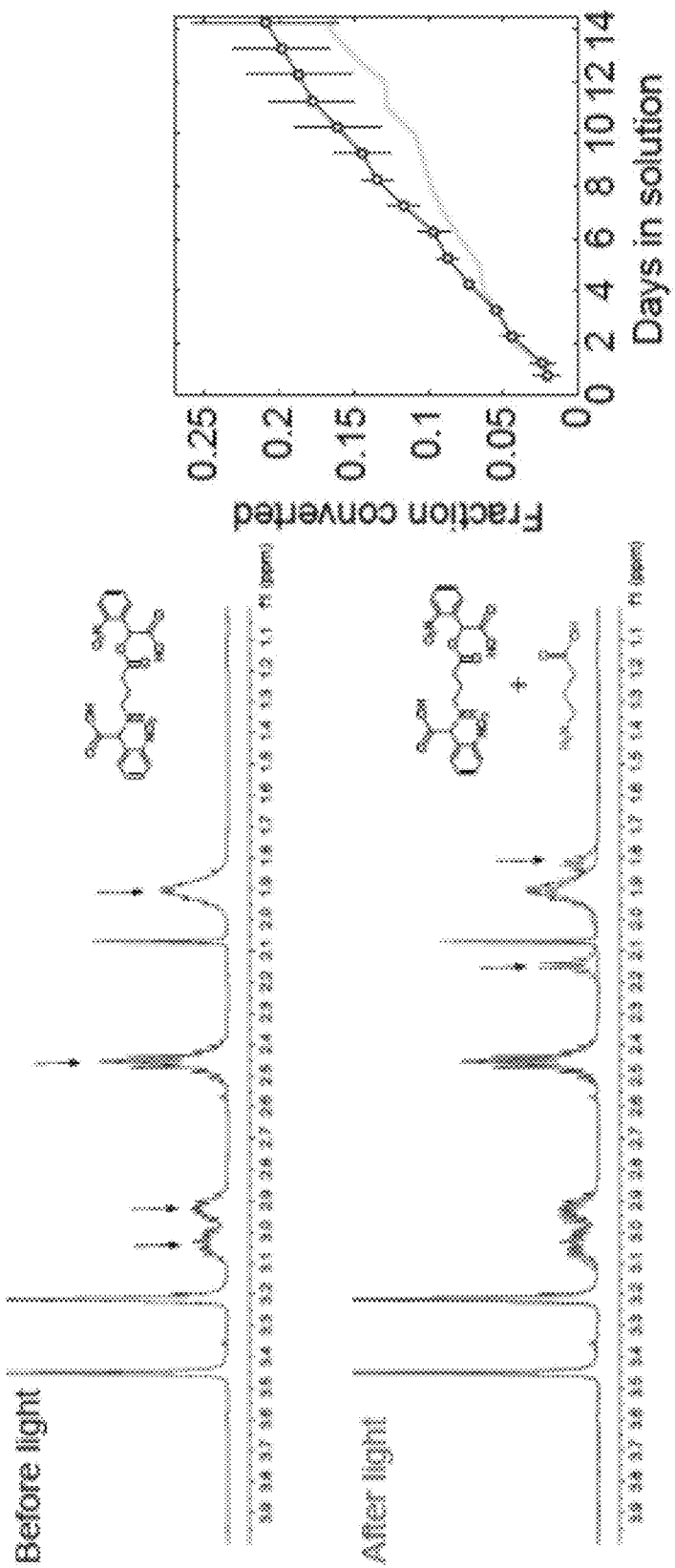
FIGS. 44A-44B illustrate accumulation of GABA in ambient room light.

FIGS. 44A-44B illustrate accumulation of GABA in ambient room light. FIG. 44A illustrates 1H NMR data used to quantify GABA accumulation. Top, bis-CNB-GABA before light exposure. Arrows denote methylene peaks of bis-CNB-GABA. Peaks at ~3.45 ppm and ~3.2 ppm in each spectrum correspond to dimethoxyethane, used as an internal standard. Bottom, The teal overlay indicates the post-photolysis spectrum of bis-CNB-GABA after 17 days of exposure to ambient fluorescent light. Arrows denote the two visible peaks corresponding to a combination of GABA and mono-N-CNB-GABA photoproducts. Note the lack of extraneous peaks in the 0-4 ppm range after light exposure. The dominant final photoproduct of bis-CNB-GABA was GABA, as identified using $^1$H NMR. FIG. 44A illustrates 1H NMR data used to quantify GABA accumulation. Referring to this figure (top), bis-CNB-GABA before light exposure. Arrows denote methylene peaks of bis-CNB-GABA. Still referring to FIG. 44A, peaks at ~3.45 ppm and ~3.2 ppm in each spectrum correspond to dimethoxyethane, used as an internal standard. Still referring to FIG. 44A (bottom), the teal overlay indicates the post-photolysis spectrum of bis-CNB-GABA after 17 days of exposure to ambient fluorescent light. Arrows denote the two visible peaks corresponding to a combination of GABA and mono-N-CNB-GABA photoproducts. The lack of extraneous peaks in the 0-4 ppm range was observed after light exposure. The combined amount of mono-decaging (N-CNB-GABA) and double-decaging (GABA) photoproduct was quantified using the integrated multiplet at 2.15 ppm, with dimethoxyethane (singlet peaks at 3.20 and 3.45 ppm) as a standard.

FIG. 44B illustrates that in aqueous solutions in the light, accumulation of photoproducts from bis-CNB-GABA (black) and GABA from mono-CNB-GABA (gray). Error bars indicate SD. Referring to FIG. 44B, over the first 8 days, it was found that bis-CNB-GABA produced photoproduct spontaneously at an approximately linear rate, 1.5±0.1%/day (n=4 runs), for an extrapolated half-life of $t_{1/2}$=98 days (95% CI, 92 to 105 days). Mono-O-CNB-GABA produced GABA at a similar rate of 1.0±0.2%/day (n=2 runs) or $t_{1/2}$=138 days (95% CI, 116 to 169 days), which is consistent with a prior report of <1% conversion in the dark at 24 hr, but not consistent with another published statement (Matsuzaki, M.; Hayama, T.; Kasai, H.; Ellis-Davies, G. C. R. Nat. Chem. Biol. 2010, 6, 255-257; Gee, K. R.; Wieboldt, R.; Hess, G. P. J. Am. Chem. Soc. 1994, 116, 8366-8367, which are incorporated herein by reference as if fully set forth).

As described above, a double-caged bis-CNB-GABA has been identified that is highly resistant to pre-uncaging interactions with $GABA_A$ receptors. Table 2 describes comparative properties of caged GABA and glutamate compounds in blocking synaptic $GABA_A$ currents. Importantly, of a wide range of structurally diverse caged GABA analogs, bis-CNB-GABA exhibits the highest half-maximal concentration ($IC_{50}$) of $GABA_A$ antagonistic activity.

TABLE 2

Comparative properties of caged GABA and glutamate compounds in blocking synaptic $GABA_A$ currents.

| Caged compound | $IC_{50}$ | Stability |
|---|---|---|
| Mono-CNB-GABA[1] | 28 µM | $t_{1/2}$ = 138 days |
| RuBi-glutamate, GABA[2] | 0.1-0.3 mM | Stable |
| DPNI-GABA[3] | 0.5 mM | Stable |
| CDNI-GABA[4] | 0.6 mM | Stable |
| Bis-CNB-GABA[5] | ≥2.5 mM | $t_{1/2}$ = 98 days |

[1]O-CNB-GABA in hippocampal dentate neurons (Molnár, P.; Nadler, J. V. Eur. J. Pharmacol. 2000, 391, 255-262).
[2]0.3 mM for RuBi-glutamate (Fino, E.; Araya, R.; Peterka, D. S.; Salierno, M.; Etchenique, R.; Yuste, R. Front. Neural Circuits, 2009, 3, 1-9). Assumes possible RuBi-GABA effect, which has only been tested at 20 µM (Rial Verde, E. M.; Zayat, L.; Etchenique, R.; Yuste, R. Front. Neural Circuits. 2008, 2, 1-8).
[3]Cerebellar interneurons (Trigo, F. F.; Papageorgiou, G.; Corrie, J. E. T.; Ogden, D. J. Neurosci. Meth., 2009, 181, 159-169).
[4](Matsuzaki, M.; Hayama, T.; Kasai, H.; Ellis-Davies, G. C. R.. Nat. Chem. Biol. 2010, 6, 255-257).
[5]The data herein.

It has been hypothesized that some cage groups may themselves antagonize $GABA_A$ receptors; if this were the case, then a double-caged-GABA analog might be expected to show an increased ability to block $GABA_A$ receptors (Rial Verde, E. M.; Zayat, L.; Etchenique, R.; Yuste, R. Front. Neural Circuits. 2008, 2, 1-8, which is incorporated herein by reference as if fully set forth).

The findings herein demonstrate the opposite, and support the view that when CNB is used as the cage group, an exposed carboxyl or amine is a key factor in residual receptor interaction.

Although it is useful to compare the relative inertness of bis-CNB-GABA as a receptor antagonist with caged compounds already in use—such as DPNI-GABA or CDNI-GABA—a more appropriate comparison from a structure-function standpoint is with the mono-O-CNB-GABA analog. Such a comparison clearly reveals the advantages of adding a second cage of similar structure to the first. In this context, it has been shown herein that adding a second cage to mono-CNB-GABA dramatically reduces receptor antagonism, by a factor of 100. Other forms of N,O-bis-caged GABA compounds would exhibit comparable reduction of antagonism compared to their O-caged analogs. Because DPNI-GABA and CDNI-GABA incorporate carboxyl-modifying groups, preparation of bis-caged analogs of these compounds would require modification of the N-position with CNB or another cage. Such a "hybrid" caged GABA should similarly exhibit minimal receptor activity. As described above, modification of GABA at the amino position by direct attachment of CNB affords uncaging responses consistent with a dark reaction time of 1.5 ms (Wieboldt, R.; Ramesh, D.; Carpenter, B. K; Hess, G. P. Biochemistry, 1994, 33, 1526-1533, which is incorporated herein by reference as if fully set forth). A previous approach had made use of a carbamate linker—which generates neurotransmitter in ~7 ms via a carbamate intermediate—out of concern that direct attachment would yield unwanted non-GABA side products (Corrie, J. E. T.; DeSantis, A.; Katayama, Y; Khodakhah, K; Messenger, J. B.; Ogden, D. C.; Trentham, D. R. J. Physiol. 1993, 465, 1-8, which is incorporated herein by reference as if fully set forth). The results herein demonstrate that, in fact, direct attachment can lead to efficient GABA production, as measured by NMR, and rapid photolysis, as measured by the time course of photolyzed currents. The high speed of uncaging obtained with bis-CNB-GABA allows for a more highly-focused chemical two-photon effect and, accordingly, micron-to-submicron localization in biological experiments. For a dark reaction of longer than ~0.2 ms, spatial resolution of uncaging for a diffraction-focused beam is limited by the distance that a caged compound diffuses before it produces agonist. For bis-CNB-GABA, an N-position dark reaction time of 1.5 ms and a diffusion constant of D=0.3 µm²/ms would predict a root-mean-square spread of $<x>^{1/2}=\sqrt{(6 \cdot D \cdot t)}=1.6$ µm. As a beam passes through brain tissue and becomes less focused due to scattering, this diffusion-based limit might not be reached. Caged compounds in solution are usually handled in room light, during which both spontaneous degradation and photolysis can occur. Under these conditions the rate of O-position degradation was similar for mono-O-CNB-GABA and bis-CNB-GABA. These findings are consistent with good stability at the carboxylate position, as previously reported, and with higher stability at the amino position. However, these results are not consistent with a claim of $t_{1/2}$=17 hours for mono-CNB-GABA in a study that did not report methods (Matsuzaki, M.; Hayama, T.; Kasai, H.; Ellis-Davies, G. C. R. Nat. Chem. Biol. 2010, 6, 255-257; Gee, K. R.; Wieboldt, R.; Hess, G. P. J. Am. Chem. Soc. 1994, 116, 8366-8367, which are incorporated herein by reference as if fully set forth). During a week in the light the production of N-CNB-GABA is estimated to be 10%; the accumulation of GABA during that period should therefore be less than 1%. Due to the possibility of accumulation of mono-CNB-GABA isomers in solution, bis-CNB-GABA should be kept dry before use, for instance through aliquoting of solutions in distilled water followed by lyophilization. It is of note that purification steps involving aqueous solution, such as preparative HPLC, might require a tradeoff in the form of accumulated mono-CNB-GABA or GABA. The use of crude product was found, without HPLC purification, to be effective in biological experiments; accordingly, crude-product level purity may be acceptable for many biological experiments.

The synthesis and evaluation of bis-CNB-GABA is described herein, and is the first caged GABA that takes advantage of chemical two-photon uncaging, achieving non-linear localized release of GABA and a significant decrease in $GABA_A$ receptor antagonism prior to photolysis. Bis-CNB-GABA is a powerful advanced optical probe that may be used to study GABAergic inhibitory effects with a degree of resolution that permits the probing of single-synapse communication and neuronal integration.

Example 24

Synthesis of bis-CNB-GABA tert-Butyl 2-(2-nitrophenyl)acetate (2)

Under nitrogen, tert-butanol (100 mL) was added to commercially available nitrophenylacetic acid (4.0 g, 22.1 mmol) and the mixture was stirred until clear. Di-tert-butyl dicarbonate (9.64 g, 44.2 mmol) was added and the mixture was stirred until dissolved. DMAP (0.8 g, 6.5 mmol) was then added, and the reaction mixture was stirred for one h at room temperature. The solvent was evaporated to generate a dark brown oil. The oil was purified by filtration through a plug of silica gel on a fritted glass funnel [$SiO_2$, EtOAc/hexane (1:9)] to generate the product, a yellow oil (4.672 g, 89%). $^1$H NMR (500 MHz, $CDCl_3$) δ 8.26-8.00 (dd, J=8.2, 1.4 Hz, 1H), 7.70-7.54 (td, J=7.6, 1.4 Hz, 1H), 7.54-7.43 (m, 1H), 7.41-7.31 (dd, J=7.6, 1.4 Hz, 1H), 4.05-3.89 (s, 2H), 1.50-1.40 (s, 9H). $^{13}$C NMR (126 MHz, $CDCl_3$) δ 169.3, 149.0, 133.6, 133.4, 130.5, 128.5, 125.3, 81.9, 41.2, 28.1. HRMS (ESI-TOF) m/z: $[M+Na]^+$ Calcd for $C_{28}H_{36}N_3O_{10}Na$, 237.10011. Found 237.10005.

tert-Butyl 2-bromo-2-(2-nitrophenyl)acetate (3)

tert-Butyl 2-(2-nitrophenyl)acetate (2) (5.08 g, 21.4 mmol), NBS (4.00 g, 22.5 mmol), and AIBN (0.528 g, 3.21 mmol) were combined under nitrogen with carbon tetrachloride (35 mL) and heated at reflux overnight. The reaction mixture was then cooled, filtered, and concentrated. The residue was purified by column chromatography [$SiO_2$, hexane/toluene (1:4)] to give the desired product (3.91 g, 64%). $^1$H NMR (500 MHz, $CDCl_3$) δ 8.06-7.90 (ddd, J=7.9, 5.0, 1.4 Hz, 1H), 7.76-7.62 (td, J=7.7, 1.4 Hz, 1H), 7.60-7.44 (ddd, J=8.6, 7.5, 1.4 Hz, 1H), 6.01-5.90 (s, 1H), 1.49-1.36 (s, 9H). $^{13}$C NMR (126 MHz, $CDCl_3$) δ 166.7, 147.8, 133.9, 133.3, 131.1, 129.9, 124.9, 83.9, 44.5, 27.8 (3). HRMS (ESI-TOF) m/z: $[M+Na]^+$ Calcd for $C_{28}H_{36}N_3O_{10}Na$, 315.01062. Found 315.01083.

2-(tert-Butoxy)-1-(2-nitrophenyl)-2-oxoethyl 4-((2-(tert-butoxy)-1-(2-nitrophenyl)-2-oxoethyl)amino) butanoate (4)

tert-Butyl 2-bromo-2-(2-nitrophenyl)acetate (3) (1.48 g, 4.68 mmol) was combined with γ-aminobutyric acid (226.4 mg, 2.20 mmol) in DMF (16 mL) under nitrogen. Potassium carbonate (481.9 mg, 3.487 mmol) was then added, and the reaction mixture was stirred at 65° C. for 36 h. Water was added and the product was extracted with EtOAc, dried with $NaSO_4$, and concentrated. The resulting material was purified by column chromatography [$SiO_2$, hexane/EtOAc (5:1 to 1:4)](850 mg, 68%). $^1$H NMR (500 MHz, $CDCl_3$) δ 8.04-7.97 (m, 1H), 7.89-7.81 (dd, J=8.1, 3.3 Hz, 1H), 7.69-7.48 (m, 5H), 7.46-7.35 (td, J=7.7, 1.8 Hz, 1H), 6.76-6.70 (d, J=1.6 Hz, 1H), 5.03-4.77 (d, J=3.0 Hz, 1H), 2.86-2.68 (dt, J=12.4, 6.4 Hz, 1H), 2.65-2.43 (m, 3H), 1.95-1.74 (p, J=7.0 Hz, 2H), 1.39-1.37 (d, J=1.6 Hz, 9H), 1.37-1.30 (s, 9H). The $^{13}$C NMR spectrum indicated the presence of diastereomers arising from the two benzylic stereocenters in the bis-CNB-GABA precursor. These apparent doublets are noted as such. $^{13}$C NMR (126 MHz, $CDCl_3$) δ 172.0 (d), 170.5, 166.5 (d), 149.4 (d), 148.2 (d), 134.1, 133.5, 133.0 (d), 129.90 (d), 129.7, 129.5 (d), 129.2, 128.5 (d), 125.1, 124.8, 83.6, 82.7, 70.2 (d), 62.0 (d), 47.6 (d), 31.7 (d), 27.9, 27.8, 25.3. HRMS (ESI-TOF) m/z: $[M+H]^+$ Calcd for $C_{28}H_{36}N_3O_{10}H$, 573.23224. Found 573.23247.

2-((4-(Carboxy(2-nitrophenyl)methoxy)-4-oxobutyl) amino)-2-(2-nitrophenyl)acetic acid, bis-CNB-GABA (5)

2-(tert-Butoxy)-1-(2-nitrophenyl)-2-oxoethyl 4-((2-(tert-butoxy)-1-(2-nitrophenyl)-2-oxoethyl)amino)butanoate (4) (436 mg, 0.76 mmol) was combined with TFA (2.94 mL, 38.4 mmol) in DCM (10 mL) under nitrogen. The reaction mixture was stirred for 5 h, and a second portion of TFA was added (2.94 mL, 38.4 mmol). A final portion of TFA (29.4 mL, 38.4 mmol) was added after 22 additional hours of stirring. The reaction mixture was concentrated, and the residue was purified by HPLC. $^1$H NMR (300 MHz, MeOD) δ 8.18-8.03 (dd, J=8.1, 1.5 Hz, 1H), 7.94-7.80 (dd, J=8.1, 1.3 Hz, 1H), 7.78-7.36 (m, 6H), 6.71-6.51 (s, 1H), 5.54-5.36 (d, J=1.4 Hz, 1H), 3.27-3.16 (s, 1H), 3.11-2.99 (m, 1H), 2.63-2.30 (q, J=6.9 Hz, 2H), 2.06-1.81 (m, 2H). The $^{13}$C NMR indicated the presence of diastereomers arising from the two benzylic stereocenters in the bis-CNB-GABA. These apparent doublets are noted as such. Certain broad peaks could be observed only with long relaxation times (d1>27 s) and these are also appropriately noted. $^{13}$C NMR (126 MHz, MeOD) δ 172.5, 170.5, 169.1, 162.3 (br), 150.1, 149.8, 135.9, 134.7, 133.2, 132.9, 131.4, 131.0, 130.4, 128.0, 127.1, 126.1, 116.0 (br), 71.3, 62.1 (br), 48.4 (d), 31.5 (d), 22.3 (d). HRMS (ESI-TOF) m/z: [M+H]$^+$ Calcd for $C_{20}H_{20}N_3O_{10}H$, 461.10704. Found 461.10735.

Quantum Yield Determination.

Quantum yield was determined by uncaging bis-CNB-GABA alongside a caged compound of known quantum yield (mono-CNB-GABA, QY=0.16, from Invitrogen). Mono-O-CNB-GABA was synthesized according to a previously published route and purified by HPLC (20% ACN in water, 0.1% TFA).

A known amount of each compound was stirred in pH 7.0 phosphate buffer in the presence of 254 nm light alongside a sample of O-CNB-GABA of equal concentration. $^1$H NMR was then used to determine the molar fractional conversion of mono-caged compound to GABA, and bis-caged compound to N-CNB-GABA+GABA (~2.1 ppm) and O-CNB-GABA (~6.4 ppm)(Gee, K. R.; Wieboldt, R.; Hess, G. P. J. Am. Chem. Soc. 1994, 116, 8366-8367, which is incorporated herein by reference as if fully set forth). The 2.1 ppm peak was integrated to give fractional uncaging at the 0-position ($\gamma_O$). For bis-CNB-GABA, the 6.4 ppm peak was divided by (1-$\gamma_O$) to obtain fractional uncaging at the N-position, $\gamma_N$. Values were then normalized to the known quantum yield of O-mono-CNB-GABA and multiplied by 2 to account for the fact that due to extinction, uncaging occurred in a layer half as thick as the mono-CNB-GABA solution (Gee, K. R.; Wieboldt, R.; Hess, G. P. J. Am. Chem. Soc. 1994, 116, 8366-8367, which is incorporated herein by reference as if fully set forth).

Example 25

Application of Double-Caged GABA

The results discussed present a promising direction for optical probing of neural activity. Though GABA has been synthesized and photolyzed with a range of cages, neurotransmitters such as dopamine and serotonin have seen less development. FIGS. 40A-40B illustrate caged dopamine and serotonin. FIG. 40A illustrates dopamine (left) caged with NPE (right). FIG. 40B illustrates serotonin (left) caged with NPE (right). Referring to these figures, dopamine and serotonin have both previously been caged with NPE on the amine through a carbamate linker. However, NPE lacks two-photon sensitivity, and the slow kinetics of uncaging through this carbamate can certainly be improved upon. Caging at the amine directly with a two-photon sensitive cage could address these limitations. In addition, the phenolic functionality is another potential caging site that can be caged. Both dopamine and serotonin therefore can benefit from both 2PE and C2PE, and future work should pursue these routes.

Figure 41:
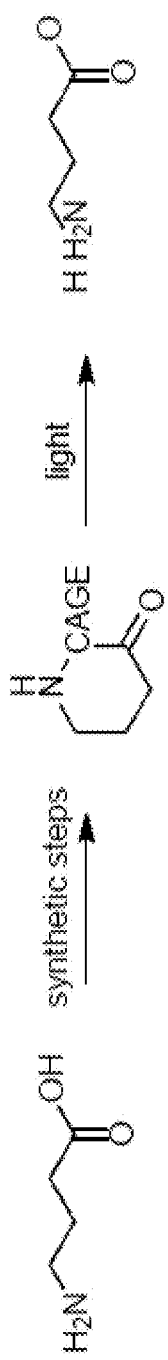
FIG. 41 illustrates a scheme of cyclic caging.

Although bis-CNB-GABA exhibits considerably less $GABA_A$ antagonism compared to its single-caged counterparts, one can imagine alternative ways to completely eliminate this effect if it is in fact due to bis-CNB-GABA itself, as opposed to residual amounts of mono-CNB-GABA. It could be advantageous to use a single cage to photoprotect GABA in a cyclic fashion, with each functional group bound to the same cage. FIG. 41 illustrates the scheme of cyclic caging. Referring to FIG. 41, both the amine and carboxylate of GABA are photo-protected with a single, two-photon sensitive cage that releases GABA upon light exposure. Under photolysis, the cage would release both the carboxylate and the amine, generating the GABA substrate and the cage byproducts. The cyclized caged GABA would be conformationally less similar to its active substrate and perhaps be less antagonistic for its native receptor. However, in order to accomplish this, the cage chosen must be able to liberate both functional groups rapidly and in the same quantities. One can imagine cleavage of only one end resulting in a single-caged GABA, which has known antagonistic properties. In addition, if this cyclic caging were to preserve the non-linear spatial resolution seen with two-photon and chemical two-photon excitation, the chosen cage should also be two-photon sensitive. These chemical and synthetic limitations make this route difficult, but not impossible. It is also important to note that cyclic caging of GABA would only reduce antagonism if the antagonism of bis-CNB-GABA is in fact due to bis-CNB-GABA itself. If it is instead a result of small amounts of decomposition that generates mono-CNB-GABA, then cyclic caging would likely be subject to the same mono-photolysis byproducts as a result of storage and handling and exhibit similar amounts of antagonism.

Finally, though bis-CNB-GABA is alone a useful probe for achieving precise photostimulation, it can be combined with other photostimulation techniques, such as optogenetics and small molecule photoswitches. A neural population of interest can be genetically engineered to incorporate ChR2 or another ion channel with a photoisomerizable photoswitch. The tissue can then be bathed in a solution of caged compound, and two distinct wavelengths of light can be used to trigger uncaging, ChR2 activation, photoisomerization, or perhaps any combination of these, thereby conferring multiple dimensions of chemical control. This is especially useful given that ChR2 and NpHR are photosensitive in the visible range (480 nm and 570 nm respectively), while caged compounds typically utilize higher energy light. Each could then be photoactived completely independently of each other using different light sources. One could use two different caged neurotransmitters together in solution, each photoprotected with a cage group that absorbs distinct wavelengths. As a result, controlled release of different neurotransmitters can be achieved in an easily executable fashion. These optical techniques are therefore both competing in the sense that they also achieve a localized neural response via photostimulation, though it is perhaps more accurate to view them as complimentary. Caged compounds used in conjunction with these other optical modes of stimulation could be especially powerful tools for achieving multidimensional photochemical control.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A composition comprising a double-caged GABA compound comprising gamma-amino butyric acid covalently linked to a first photosensitive protecting group linked to a carboxyl of the gamma-amino butyric acid and a second photosensitive protecting group linked to an amine of the gamma-amino butyric acid, wherein
the first and second photosensitive protecting groups are independently selected from the group consisting of: nitrobenzyl (NB), nitrophenyl ethyl (NPE), α-carboxy-2-nitrobenzyl (CNB), 4,5-dimethoxy-2-nitrobenzyl (DMNB), (4,5-dimethoxy-2-nitrophenyl)ethyl (DM-NPE), 4-methoxy-7-nitroindoline (MNI), 4-carboxymethoxy-5,7-dinitroindolinyl (CDNI), 6-bromo-7-hydroxycoumarin-4-ylmethoxycarbonyl (Bhc), ruthenium-bipyridine-triphenylphosphine (RuBi), and carboxynitrobenzyl, and
the double-caged GABA compound is biologically inert before exposure to light, and the first photosensitive protecting group and the second photosensitive protecting group cleave from the gamma-amino butyric acid by photolysis upon exposure of the double-caged GABA compound to light.

2. The composition of claim 1, wherein the group selected as the first photosensitive protecting group is the same group as selected the second photosensitive protecting group.

3. The composition of claim 1, wherein the first photosensitive protecting group or any byproduct thereof and the second photosensitive protecting group or any byproduct thereof is biologically inert after exposure to light and cleavage from the double-caged GABA compound.

4. The composition of claim 1, wherein the double-caged GABA compound has the structure of Formula I:

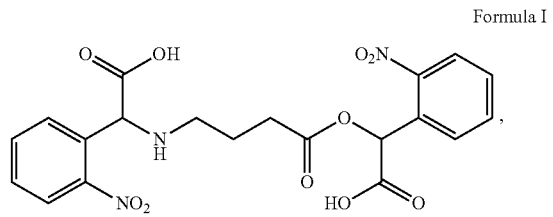 [SMILES: O=C(CCCNC(C(=O)O)c1ccccc1[N+](=O)[O-])OC(C(=O)O)c1ccccc1[N+](=O)[O-]]

Formula I or a salt thereof.

5. The composition of claim 1, wherein the double-caged GABA compound is soluble in an aqueous solution.

6. The composition of claim 1, wherein light has a wavelength in a range from 250 nm to 500 nm.

7. A method of synthesizing a double-caged GABA compound according to claim 1 comprising conjugating the first photosensitive protecting group and the second photosensitive protecting group to a gamma-amino butyric acid.

8. The method of claim 7, wherein the first photosensitive protecting group is conjugated to the carboxyl of the gamma-amino butyric acid.

9. The method of claim 7, wherein the second photosensitive protecting group is conjugated to the amine of the gamma-amino butyric acid.

10. The method of claim 7, wherein the first photosensitive protecting group and the second photosensitive protecting groups are simultaneously conjugated to the gamma-amino butyric acid at the carboxy position and the amine position, respectively.

11. The method of claim 7, wherein prior to conjugating the first photosensitive protecting group and the second photosensitive protecting groups are included in an intermediate compound.

12. The method of claim 11, wherein conjugating includes combining the intermediate compound and the gamma-amino butyric acid in a solvent to form a mixture and providing an inert gas over the mixture.

13. The method of claim 12 further comprising allowing the mixture to react for 1 hour to 25 hours.

14. The method of claim 11, wherein the intermediate compound is benzyl bromide.

15. A method of chemical stimulation of a biological sample comprising: adding a double-caged GABA compound according to claim 1 to the biological sample and exposing the double-caged GABA compound in the biological sample to light.

16. The method of claim 15, wherein the biological sample is selected from the group consisting of: cells, neurons, a tissue, and a slice of brain tissue.

17. The method of claim 16, wherein the biological sample is the slice of brain tissue.

18. The method of claim 15, wherein the double-caged GABA compound has the structure of Formula I:

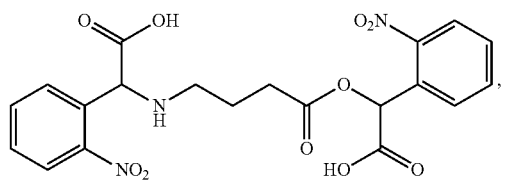

Formula I or a salt thereof.

19. The method of claim 15, wherein the double-caged GABA compound is exposed to light selected from the group consisting of: UV light, pulsed infrared light, and visible light.

20. The method of claim 15, wherein the double-caged GABA compound is exposed to light in a range from 250 nm to 500 nm wavelength.

21. The method of claim 15, wherein the double-caged GABA compound is exposed to light for a period from 0.001 ms to 1000 ms.

22. The method of claim 15 further comprising measuring the effect of chemical stimulation in a biological sample.

23. The method of claim 21, wherein measuring the effect of chemical is stimulation includes at least one parameter selected from the group consisting of: whole-cell ionic current, AMPA or GABA receptor density, correlation between AMPA or GABA receptor density and spine location, neuron connectivity, synaptic input and neuronal output.

24. The method of claim 21, wherein measuring includes at least one procedure selected from the group consisting of: measuring an extinction coefficient, determining quantum yield, whole-cell patch clamp recording, imaging intracellular second messengers, and measuring intensity of illumination.

25. The composition of claim 1, wherein the first photosensitive protecting group is nitrobenzyl (NB) and second photosensitive protecting groups is nitrobenzyl (NB).

26. The composition of claim 1, wherein the first photosensitive protecting group is nitrophenyl ethyl (NPE) and second photosensitive protecting groups is nitrophenyl ethyl (NPE).

27. The composition of claim 1, wherein the first photosensitive protecting group is α-carboxy-2-nitrobenyzl (CNB) and second photosensitive protecting groups is α-carboxy-2-nitrobenyzl (CNB).

28. The composition of claim 1, wherein the first photosensitive protecting group is 4,5-dimethoxy-2-nitrobenzyl (DMNB) and second photosensitive protecting groups is 4,5-dimethoxy-2-nitrobenzyl (DMNB).

29. The composition of claim 1, wherein the first photosensitive protecting group is (4,5-dimethoxy-2-nitrophenyl) ethyl (DMNPE) and second photosensitive protecting groups is (4,5-dimethoxy-2-nitrophenylethyl (DMNPE).

30. The composition of claim 1, wherein the first photosensitive protecting group is 4-methoxy-7-nitroindoline (MNI) and second photosensitive protecting groups is 4-methoxy-7-nitroindoline (MNI).

31. The composition of claim 1, wherein the first photosensitive protecting group is 4-carboxymethoxy-5,7-dinitroindolinyl (CDNI) and second photosensitive protecting groups is 4-carboxymethoxy-5,7-dinitroindolinyl (CDNI).

32. The composition of claim 1, wherein the first photosensitive protecting group is 6-bromo-7-hydroxycoumarin-4-ylmethoxycarbonyl (Bhc) and second photosensitive protecting groups is 6-bromo-7-hydroxycoumarin-4-ylmethoxycarbonyl (Bhc).

33. The composition of claim 1, wherein the first photosensitive protecting group is ruthenium-bipyridine-triphenylphosphine (RuBi) and second photosensitive protecting groups is ruthenium-bipyridine-triphenylphosphine (RuBi).

34. The composition of claim 1, wherein the first photosensitive protecting group is carboxynitrobenzyl and second photosensitive protecting groups is carboxynitrobenzyl.

* * * * *

UNITED STATES PATENT AND TRADEMARK OFFICE
CERTIFICATE OF CORRECTION

PATENT NO. : 9,625,448 B2
APPLICATION NO. : 14/664445
DATED : April 18, 2017
INVENTOR(S) : Shi et al.

Page 1 of 1

It is certified that error appears in the above-identified patent and that said Letters Patent is hereby corrected as shown below:

In the Specification

In Column 1, Line 10, change Grant No. "N5045193" to --NS045193--

Signed and Sealed this
Twenty-third Day of January, 2018

Joseph Matal
*Performing the Functions and Duties of the
Under Secretary of Commerce for Intellectual Property and
Director of the United States Patent and Trademark Office*